United States Patent
Pichuantes et al.

(10) Patent No.: US 6,942,965 B2
(45) Date of Patent: Sep. 13, 2005

(54) HEPATITIS A VIRUS NUCLEOTIDE SEQUENCES, RECOMBINANT PROTEINS AND USES THEREOF

(75) Inventors: Sergio Pichuantes, El Cerrito, CA (US); Steve H. Nguyen, Hercules, CA (US)

(73) Assignee: Chiron Corporation, Emeryville, CA (US)

( * ) Notice: Subject to any disclaimer, the term of this patent is extended or adjusted under 35 U.S.C. 154(b) by 130 days.

(21) Appl. No.: 10/272,459

(22) Filed: Oct. 15, 2002

(65) Prior Publication Data

US 2003/0124517 A1 Jul. 3, 2003

Related U.S. Application Data

(60) Provisional application No. 60/328,933, filed on Oct. 12, 2001.

(51) Int. Cl.[7] .................................................. C12Q 1/70
(52) U.S. Cl. .............................. 435/5; 435/6; 536/23.1; 536/23.72
(58) Field of Search .............................. 536/23.1, 23.72; 424/226.1; 435/5, 6

(56) References Cited

U.S. PATENT DOCUMENTS

5,516,630 A * 5/1996 Ticehurst et al. ............... 435/5

OTHER PUBLICATIONS

Cohen et al., "Complete Nucleotide Sequence of Wild–Type Hepatitis A Virus: Comparison with Different Strains of Hepatitis A Virus and Other Picomaviruses," *J. Virology* 61(1):50–59, 1987.

Locarnini et al., "Restricted replication of human hepatitis A virus in cell Culture: intracellular biochemical studies," *J. Virol.* 37:216–225, 1981.

Siegl et al., "The physicochemical properties of infectious hepatitis A virions," *J. Gen. Virol.* 57:331–341, 1981.

* cited by examiner

*Primary Examiner*—Laurie Scheiner
(74) *Attorney, Agent, or Firm*—Robert P. Blackburn; Roberta L. Robins; Marcella Lillis

(57) ABSTRACT

Hepatitis A virus primers and probes derived from the capsid proteins and junction between the capsid precursor P1 and 2A of the HAV genome are disclosed. Also disclosed are nucleic acid-based assays using the primers and probes, antigen detection of HAV, and immunoassay for detecting the antibodies that bind to HAV.

6 Claims, 30 Drawing Sheets

FIGURE 1

IND-1-2
TGCTCCTCTTTATCATGCTATGGATGTCACCACACAGGTTGGAGATGATTCCGGAGGTTTTTCAACGACAGT
TTCTACAGAGCAGAATGTTCCAGATCCCCAAGTTGGTATAACAACTATGAAGGATTTAAAAGGAAAAGCCAA
TAGAGGGAAAATGGATGTTTCAGGAGTACAAGCACCTGTGGGAGCTATTACAACAATTGAGGATCCAGTTTT
AGCAAAGAAAGTACCTGAGACATTTCCTG

IND-2-2
GCTCCTCTTTATCATGCTATGGATGTCACCACACAGGTTGGAGATGATTCCGGAGGTTTTTCAACGACAGTT
TCTACAGAGCAGAATGTTCCTGATCCCCAAGTTGGCATAACAACCATGAGGGACTTAAAAGGGAAAGCCAAT
AGGGGGAAGATGGATGTTTCAGGAGTGCAAGCACCTGTGGGAGCTATTACAACAATTGAGGATCCAGTTTTA
GCAAAGAAAGTACCTGAGACATTTCCTGA

IND-2-4
TGCTCCTCTTTATCATGCTATGGATGTCACCACACAGGTTGGAGATGATTCCGGAGGTTTTTCAACGACAGT
TTCTACAGAGCAGAATGTTCCAGATCCCCAAGTTGGTATAACAACCATGAGGGATTTAAAAGGAAAAGCCAA
TAGAGGGAAAATGGATGTTTCAGGAGTACAAGCACCTGTGGGAGCTATTACAACAATTGAGGATCCAGTTTT
AGCAAAGAAAGTACCTGAGACATTTCCTG

IND-3-2
TGCTCCTCTTTATCATGCTATGGATGTCACCACACAGGTTGGAGATGATTCCGGAGGTTTTTCAACAACAGT
TTCTACAGAGCAGAATGTTCCTGATCCCCAAGTTGGCATAACAACCATGAGGGATTTAAAAGGGAAAGCTAA
TAGGGGAAAGATGGATGTGTCAGGAGTGCAAGCACCTGTGGGAGCCATCACAACAATTGAGGATCCAGTTTT
AGCAAAGAAAGTACCTGAGACATTTCCTG

IND-4-5
GCTCCTCTTTATCATGCTATGGATGTCACCACACAGGTTGGAGATGATTCCGGAGGTTTTTCAACGACAGTT
TCTACAGAGCAGAATGTTCCAGATCCCCAAGTTGGTATAACAACTATGAAGGATTTAAAAGGAAAAGCCAAT
AGAGGGAAAATGGATGTTTCAGGAGTACAAGCACCTGTGGGAGCTATCACAACAATTGAGGATCCAGTTTTA
GCAAAGAAAGTACCTGAGACATTTCCTGA

IND-6-4
TGCTCCTCTTTATCATGCTATGGATGTCACCACACAGGTTGGAGATGATTCCGGAGGTTTTTCAACGACAGT
TTCTACAGAGCAGAATGTTCCAGATCCCCAAGTTGGTATAACAACTATGAAGGATTTAAAAGGAAAAGCCAA
TAGAGGGAAAATGGATGTTTCAGGAGTACAAGCACCTGTGGGAGCTATTACAACAGTTGAGGATCCAGTTTT
AGCAAAGAAAGTACCTGAGACATTTCCTG

IND-7-1
GCTCCTCTTTATCATGCTATGGATGTCACCACACAGGTTGGAGATGATTCCGGAGGTTTTTCAACGACAGTT
TCTACAGAGCAGAATGTTCCAGATCCCCAAGTTGGTATAACAACTATGAAGGATTTAAAAGGAAAAGCCAAT
AGAGGGAAAATGGATGTTTCAGGAGTACAAGCACCTGTGGGAGCTATTACAACAGTTGAGGATCCAGTTTTA
GCAAAGAAAGTACCTGAGACATTTCCTGA

IND-8-2
GCTCCTCTTTATCATGCTATGGATGTCACCACACAGGTTGGAGATGATTCCGGAGGTTTTTCAACGACAGTT
TCTACAGAGCAGAATGTTCCAGATCCCCAAGTTGGTATAACAACTATGAAGGATTAAAAGGAAAAGCCAAT
AGAGGGAAAATGGATGTTTCAGGAGTACAAGCACCTGTGGGAGCTATTACAACAGTTGAGGATCCAGTTTTA
GCAAAGAAAGTACCTGAGACATTTCCTGA

IND-9-1
TGCTCCTCTTTATCATGCTATGGATGTCACCACACAGGTTGGAGATGATTCCGGAGGTTTTTCAACGACAGT
TTCTACAGAGCAGAATGTTCCAGATCCCCAAGTTGGTATAACAACTATGAAGGATTTAAAAGGAAAAGCCAA
TAGAGGGAAAATGGATGTTTCAGGAGTACAAGCACCTGTGGGAGCTATTACAACAGTTGAGGATCCAGTTTT
AGCAAAGAAAGTACCTGAGACATTTCCTG

IND-10-5
TGCTCCTCTTTATCATGCTATGGATGTCACCACACAGGTTGGAGATGATTCCGGAGGTTTTTCAACGACAGT
TTCTACAGAGCAGAATGTTCCTGGTCCCCAAGTTGGCATAACAACCATGAGGGACTTAAAAGGGAAAGCCAA
TAGGGGGAAGATGGATGTTTCAGGAGTGCAAGCACCTGTGGGAGCTATTACAACAATTGAGGATCCAGTTTT
AGCAAAGAAAGTACCTGAGACATTTCCTG

IND-11-5
TGCTCCTCTTTATCATGCTATGGATGTCACCACACAGGTTGGAGATGATTCCGGAGGTTTTTCAACGACAGT
TTCTACAGAGCAGAATGTTCCAGATCCCCAAGTTGGTATAACAACTATGAAGGATTTAAAAGGAAAAGCCAA
TAGAGGGAAAATGGATGTTTCAGGAGTACAAGCACCTGTGGGAGCTATTACAACAATTGAGGATCCAGTTTT
AGCAAAGAAAGTACCTGAGACATTTCCTG

IND-12-1
GCTCCTCTTTATCATGCTATGGATGTTACTACACAGGTTGGAGATGATTCAGGAGGTTTCTCAACAACAGTT
TCCACAGAGCAGAATGTTCCTGATCCCCAAGTTGGGATAACAACCATGAGGGATTTAAAAGGGGAAGCCAAT
AGGGGAAAGATGGATGTTTCAGGAGTGCAAGCACCTGTGGGAGCTATCACAACAATTGAGGATCCAGTTTTA
GCAAAGAAAGTACCTGAGACATTTCCTGA

IND-12-2
CTCCTCTTTATCATGCTATGGATGTTACCACACAGGTTGGAGATGATTCAGGAGGTTTTTCAACAACAGTTT
CTACAGAGCAGAATGTTCCTGATCCCCAAGTTGGCATAACAACCATGAGGGACTTAAAAGGGAAAGCCAATA
GGGGGAAGATGGATGTTTCAGGAGTGCAAGCACCTGTGGGAGCTATTACAACAATTGAGGATCCAGTTTTAG
CAAAGAAAGTACCTGAGACATTTCCTGA

SCL2-10
TGCTCCTCTTTATCATGCTATGGATGTCACCACACAGGTTGGAGATGATTCCGGGGGTTTTTCAACGACAGT
TTCTACAGAGCAGAATGTTCCAGATCCCCAAGTTGGTATAACAACTATGAAGGATTTAAAAGGAAAAGCCAA
TAGAGGGAAAATGGATGTTTCAGGAGTACAAGCACCTGTGGGAGCTATTACAACAGTTGAGGATCCAGTTTT
AGCAAAGAAAGTACCTGAGACATTTCCTG

SCL3-10
GCTCCTCTTTATCATGCTATGGATGTCACCACACAGGTTGGAGATGATTCCGGAGGTTTTTCAACGACAGTT
TCTACAGAGCAGAATGTTCCAGATCCCCAAGTTGGTATAACAACTATGAAGGATTTAAAAGGAAAAGCCAAT
AGAGGGAAAATGGATGTTTCAGGAGTACAAGCACCTGTGGGAGCTATTACAACAGTTGAGGATCCAGTTTTA
GCAAAGAAAGTACCTGAGACATTTCCTGA

SCL4-3
GCTCCTCTTTATCATGCTATGGATGTTACCACACAGGTTGGAGACGATTCAGGAGGTTTTTCAACAACAGTT
TCTACTGAGCAGAATGTTCCTGATCCCCAAGTTGGTATAACAACCATGAGGGACCTAAAAGGGAAAGCCAAT
AGAGGGAAGATGGATGTTTCAGGAGTACAAGCACCTGTGGGAGCTATTACAACAATTGAGGATCCAGTCTTG
GCAAAGAAAGTACCTGAGACATTTCCTGA

SCL7-6
GCTCCTCTTTATCATGCTATGGATGTCACCACACAGGTTGGAGATGATTCCGGAGGTTTTTCAACGACAGTT
TCTACAGAGCAGAATGTTCCAGATCCCCAAGTTGGTATAACAACTATGAAGGATTTAAAAGGAAAAGCCAAT
AGAGGGAAAATGGATGTTTCAGGAGTACAAGCACCTGTGGGAGCTATTACAACAGTTGAGGATCCAGTTTTA
GCAAAGAAAGTACCTGAGACATTTCCTGA

SCL8-2
GCTCCTCTTTATCATGCTATGGATGTCACCACACAGGTTGGAGATGATTCAGGAGGTTTTTCAACAACAGTT
TCTACAGAACAGAATGTTCCTGATCCCCAGGTTGGCATAACAACTATGAGGGATCTAAAAGGGAAGGCCAAT
AGTGGAAAGATGGATGTTTCAGGAGTGCAAGCACCTGTGGGGGCTATTACAACAATTGAGGATCCAGTTTTA
GCAAAGAAAGTACCTGAGACATTTCCTGA

SCL8-5
GCTCCTCTTTATCATGCTATGGATGTCACCACACAGGTTGGAGATGATTCAGGAGGTTTTTCAACAACAGTT
TCTACAGAGCAGAATGTTCCTGATCCCCAGGTTGGCATAACAACTATGAGGGATCTAAAAGGGAAGGCCAAT
AGTGGAAAGATGGATGTTTCAGGAGTGCAAGCACCTGTGGGGGCTATTACAACAATTGAGGATCCAGTTTTA
GCAAAGAAAGTACCTGAGACATTTCCTGA

SCL9-4
GCTCCTCTTTATCATGCTATGGATGTTACCACACAGGTTGGAGATGATTCAGGAGGTTTTTCAACAACAGTT
TCTACAGAACAGAATGTTCCTGATCCCCAGGTTGGCATAACAACTATGAGGGATCTAAAAGGGAAGGCCAAT
AGTGGAAAGATGGATGTTTCAGGAGTGCAAGCACCTGTGGGGGCTATTACAACAATTGAGGATCCAGTTTTA
GCAAAGAAAGTACCTGAGACATTTCCTGA

SCL10-1
GCTCCTCTTTATCATGCTATGGATGTTACCACACAGGTTGGAGATGATTCAGGAGGTTTTTCAACAACAGTT
TCTACAGAACAGAATGTTCCTGATCCCCAGGTTGGCATAACAACTATGAGGGATCTAAAAGGGAAGGCCAAT

AGTGGAAAGATGGATGTTTCAGGAGTGCAAGCACCTGTGGGGGCTATTACAACAATTGAGGATCCAGTTTTA
GCAAAGAAAGTACCTGAGACATTTCCTGA

SCL11-5
GCTCCTCTTTATCATGCTATGGATGTTACCACACAGGTTGGAGATGATTCAGGAGGTTTTTCAACAACAGTT
TCTACAGAACAGAATGTTCCTGATCCCCAGGTTGGCATAACAACTATGAGGGATCTAAAAGGGAAGGCCAAT
AGTGGAAAGATGGATGTTTCAGGAGTGCAAGCACCTGTGGGGGCTATTACAACAATTGAGGATCCAGTTTTA
GCAAAGAAAGTACCTGAGACATTTCCTGA

SCL12-6
GCTCCTCTTTATCATGCTATGGATGTCACCACACAGGTTGGAGATGATTCCGGAGGTTTTTCAACGACAGTT
TCTACAGAGCAGAATGTTCCAGATCCCCAAGTTGGTATAACAACTATGAAGGATTTAAAAGGAAAAGCCAAT
AGAGGGAAAATGGATGTTTCAGGAGTACAAGCACCTGTGGGAGCTATTACAACAGTTGAGGATCCAGTTTTA
GCAAAGAAAGTACCTGAGACATTTCCTGA

SCL14-3
GCTCCTCTTTATCATGCTATGGATGTTACCACACAGGTTGGAGACGATTCAGGAGGTTTTTCAACAACAGTT
TCTACAGAGCAGAATGTTCCTGATCCCCAAGTTGGTATAACAACCATGAGGGACCTAAAAGGGAAAGCCAAT
AGAGGGAAGATGGATGTTTCAGGAGTACAAGCACCTGTGGGAGCTATTACAACAATTGAGGATCCAGTCTTG
GCAAAGAAAGTACCTGAGACATTTCCTGA

SCL15-1
GCTCCTCTTTATCATGCTATGGATGTTACCACACAGGTTGGAGACGATTCAGGAGGTTTTTCAACAACAGTT
TCTACAGAGCAGAATGTTCCTGATCCCCAAGTTGGTATAACAACCATGAGGGACCTAAAAGGGAAAGCCAAT
AGAGGGAAGATGGATGTTTCAGGAGTACAAGCACCTGTGGGAGCTATTACAACAATTGAGGATCCAGTTTTG
GCAAAGAAAGTACCTGAGACATTTCCTGA

SCL15-2
GCTCCTCTTTATCATGCTATGGATGTTACCACACAGGTTGGAGACGATTCAGGAGGTTTTTCAACAACAGTT
TCTACAGAGCAGAATGTTCCTGATCCCCAAGTTGGTATAACAACCATGAGGGACCTAAAAGGGAAAGCCAAT
AGAGGGAAGATGGATGTTTCAGGAGTACAAGCACCTGTGGGAGCTATTACAACAATTGAGGATCCAGTCTTG
GCAAAGAAAGTACCTGAGACATTTCCTGA

SCL16-8
GCTCCTCTTTATCATGCTATGGATGTTACCACACAGGTTGGAGATGATTCAGGAGGTTTTTCAACAACAGTT
TCTACAGAACAGAATGTTCCTGATCCCCAGGTTGGCATAACAACTATGAGGGATCTAAAAGGGAAGGCCAAT
AGTGGAAAGATGGATGTTTCAGGAGTGCAAGCACCTGTGGGGGCTATTACAACAATTGAGGATCCAGTTTTA
GCAAAGAAAGTACCTGAGACATTTCCTGA

FIGURE 2

```
   1 ggtaccatga atatgtccaa acaaggaatt ttccagactg ttgggagtgg ccttgaccac
  61 atcctgtctt tggcagatat tgaggaagag caaatgattc agtccgttga taggactgca
 121 gtgactggag cttcttactt cacttctgtg gaccaatctt cagttcatac tgctgaggtt
 181 ggctcacatc aaattgaacc tttgaaaacc tctgttgata aacctggttc taagaaaact
 241 caggggggaaa agttttttcct gattcattct gctgattggc tcactacaca tgctctcttt
 301 catgaagttg caaaattgga tgtggtgaaa ctactgtata atgagcagtt tgccgtccaa
 361 ggtttgttga gataccatac atatgcaaga tttggcattg agattcaagt tcagataaat
 421 cccacaccct ttcagcaagg aggactaatt tgtgccatgg ttcctggtga ccaaagttat
 481 ggttcaatag catccttgac tgtttatcct catggtctgt taaattgcaa tatcaacaat
 541 gtagttagaa taaaggttcc atttatttat actagaggtg cttatcattt taaagatcca
 601 cagtacccag tttgggaatt gacaatcaga gtttggtcag agttgaatat tggaacagga
 661 acttcagctt acacttcact caatgtttta gctaggttta cagatttgga gttgcatgga
 721 ttaactcctc tttctacaca gatgatgaga atgaattta gggtcagtac tactgaaaat
 781 gttgtaaatt tgtcaaatta tgaagatgca agggcaaaaa tgtcttttgc tttggatcag
 841 gaagattgga agtctgatcc ttcccaaggt ggtggaatta aaattactca ttttactacc
 901 tggacatcca ttccaacctt agctgctcag tttccattta atgcttcaga ttcagttgga
 961 caacaaatta aagttattcc agtggaccca tacttttcc aaatgacaaa cactaatcct
1021 gatcaaaaat gtataactgc cttggcctct atttgtcaga tgttctgctt tggaggggga
1081 gatcttgttt ttgatttca ggttttcca accaaatatc attcaggtag actgttgttt
1141 tgttttgttc ctgggaatga gttaatagat gttactggaa ttacattaaa acaggcaact
1201 actgctcctt gtgcagtgat ggacattaca ggagtgcagt caaccttgag atttcgtgtt
1261 ccttggattt ctgatacacc ttatcgagtg aataggtaca cgaagtcagc acatcaaaaa
1321 ggtgagtaca ctgccattgg gaagcttatt gtgtattgtt ataacagact gacttctcct
1381 tctaatgttg cttctcatgt tagagttaat gtttatctt cagcaattaa tttggaatgt
1441 tttgctcctc tttaccatgc tatggatgtt actacacagg ttggagatga ttcaggaggt
1501 ttctcaacaa cagtttctac agagcagaat gttcctgatc cccaagttgg gataacaacc
1561 atgagggatt taaaggaaa agccaatagg ggaaagatgg atgtttcagg agtgcaagca
1621 cctgtgggag ctatcacaac aattgaagat ccagtttag caagaaagt acctgagaca
1681 tttcctgaat tgaagcctgg agagtccaga catacatcag atcacatgtc tatttataaa
1741 ttcatgggaa ggtctcattt tttgtgcact tttactttca attcaaataa taaagagtac
1801 acatttccaa taaccctgtc ttcgacttct aatcctccte atggtttacc atcaacatta
1861 aggtggttct tcaatttgtt tcagttgtat agaggaccat tggatttaac aattataatc
1921 acaggagcca ctgatgtgga tggtatggcc tggtttactc cagtgggcct tgctgtcgac
1981 accccttggg tggaaaagga gtcagctttg tctattgatt ataaaactgc ccttggagct
2041 gttagattta atacaagaag aacaggaaac attcaaatta gattgccgtg gtattcttat
2101 ttgtatgccg tgtctggagc actggatggc ttgggggata agacagattc tacatttgga
2161 ttggtttcta ttcagattgc aaattacaat cattctgatg aatatttgtc cttcagttgt
2221 tatttgtctg tcacagagca atcagagttc tatttttccta gagctccatt aaattcaaat
2281 gctatgttgt ccactgaatc catgatgagt agaattgcag ctggagactt ggagtcatca
2341 gtggatgatc ccagatcaga ggaggataga agatttgaga gtcatataga atgtaggaaa
2401 ccatacaaag aattgagact ggaggttggg aaacaaagac tcaaatatgc tcaggaagag
2461 ttatcaaatg aagtgcttcc acctcctagg aaaatgaagg ggttatttc acaagctaaa
2521 atttctctt tttatactga ggagcatgaa ataatgaagt tttcttggag aggagtgact
2581 gctgatacta gggctttgag aagatttgga ttctctctgg ctgctggtag aagtgtgtgg
2641 actcttgaaa tggatgctgg agttcttact ggaagattga tcagattgaa tgatgagaaa
2701 tggacagaaa tgaaggatga taagattgtt tcattaattg aaaagttcac aagcaataaa
2761 tattggtcta aagtgaattc tccacatgga atgttggatc ttgaagaaat gctgccaatt
2821 ctaagatttt ccaaatatgt ctgagacaga tttgtgtttc ctgttacatt ggctaaatcc
2881 aaagaaaatc aatttagcag atagaatgct tggattgtct ggagtgcagg aaattaagga
2941 acaggcatgc
```

FIGURE 3

```
   1 ggtaccatga atatgtccaa acaaggaatt ttccagactg ttgggagtgg ccttgaccac
  61 atcctgtctt tggcagatat tgaggaagag caaatgattc agtccgttga taggactgca
 121 gtgactggag cttcttactt cacttctgtg gaccaatctt cagttcatac tgctgaggtt
 181 ggctcacatc aaattgaacc tttgaaaacc tctgttgata aacctggttc taagaaaact
 241 caggggaaa agttttttcct gattcattct gctgattggc tcactacaca tgctctcttt
 301 catgaagttg caaaattgga tgtggtgaaa ctactgtata atgagcagtt tgccgtccaa
 361 ggtttgttga gataccatac atatgcaaga tttggcattg agattcaagt tcagataaat
 421 cccacaccct tcagcaagg aggactaatt tgtgccatgg ttcctggtga ccaaagttat
 481 ggttcaatag catccttgac tgtttatcct catggtctgt taaattgcaa tatcaacaat
 541 gtagttagaa taaaggttcc atttatttat actagaggtg cttatcattt taaagatcca
 601 cagtacccag tttgggaatt gacaatcaga gtttggtcag agttgaatat tggaacagga
 661 acttcagctt acacttcact caatgtttta gctaggttta cagatttgga gttgcatgga
 721 ttaactcctc tttctacaca gatgatgaga atgaattta gggtcagtac tactgaaaat
 781 gttgtaaatt tgtcaaatta tgaagatgca agggcaaaaa tgtctttgc tttggatcag
 841 gaagattgga agtctgatcc ttcccaaggt ggtggaatta aaattactca ttttactacc
 901 tggacatcca ttccaacctt agctgctcag tttccattta atgcttcaga ttcagttgga
 961 caacaaatta agttattcc agtggaccca tactttttcc aaatgacaaa cactaatcct
1021 gatcaaaaat gtataactgc cttggcctct atttgtcaga tgttctgctt ttggagggga
1081 gatcttgttt ttgattttca ggttttttcca accaaatatc attcaggtag actgttgttt
1141 tgttttgttc ctgggaatga gttaatagat gttactggaa ttacattaaa acaggcaact
1201 actgctcctt gtgcagtgat ggacattaca ggagtgcagt caaccttgag atttcgtgtt
1261 ccttggattt ctgatacacc ttatcgagtg aataggtaca cgaagtcagc acatcaaaaa
1321 ggtgagtaca ctgccattgg gaagcttatt gtgtattgtt ataacagact gacttctcct
1381 tctaatgttg cctctcatgt tagagttaat gtttatcttt cagcaattaa tttggaatgt
1441 tttgctcctc tttaccatgc tatggatgtt actacacagg ttggagatga ttcaggaggt
1501 ttctcaacaa cagtttctac agagcagaat gttcctgatc cccaagttgg gataacaacc
1561 atgagggatt taaaaggaaa agccaatagg ggaaagatgg atgtttcagg agtgcaagca
1621 cctcgtggga gctatcagca acaattgaac gatccagttt tagcaaagaa agtacctgag
1681 acatttcctg aattgaagcc tggagagtcc agacatacat cagatcacat gtctatttat
1741 aaattcatgg gaaggtctca ttttttgtgc acttttactt tcaattcaaa taataaagag
1801 tacacatttc caataaccct gtcttcgact tctaatcctc ctcatggttt accatcaaca
1861 ttaaggtggt tcttcaattt gtttcagttg tatagaggac cattggattt aacaattata
1921 atcacaggag ccactgatgt ggatggtatg gcctggttta ctccagtggg ccttgctgtc
1981 gacccttggg tggaaaagga gtcagcttg tctattgatt ataaaactgc ccttggagct
2041 gttagattta atacaagaag aacaggaaac attcaaatta gattgccgtg gtattcttat
2101 ttgtatgccg tgtctggagc actggatggc ttgggggata agacagattc tacatttgga
2161 ttgtttctat tcgagattgc aaattacaat cattctgatg aatatttgtc cttcagttgt
2221 tatttgtctg tcacagagca atcagagttc tatttttccta gagctccatt aaattcaaat
2281 gctatgttgt ccactgaatc catgatgagt agaattgcag ctggagactt ggagtcatca
2341 gtggatgatc ccagatcaga ggaggataga agatttgaga gtcatataga atgtaggaaa
2401 ccatacaaag aattgagact ggaggttggg aaacaaagac tcaaatatgc tcaggaagag
2461 ttatcaaatg aagtgcttcc acctcctagg aaaatgaagg ggttattttc acaagctaaa
2521 atttctcttt tttatactga ggagcatgaa ataatgaagt tttcttggag aggagtgact
2581 gctgatacta gggctttgag aagatttgga ttctctctgg ctgctggtag aagtgtgtgg
2641 actcttgaaa tggatgctgg agttcttact ggaagattga tcagattgaa tgatgagaaa
2701 tggacagaaa tgaaggatga taagattgtt tcattaattg aaaagttcac aagcaataaa
2761 tattggtcta aagtgaattt tccacatgga atgttggatc ttgaagaaat tgctgccaat
2821 tctaaggatt ttccaaatat gtctgagaca gatttgtgtt tcctgttaca ttggctaaat
2881 ccaaagaaaa tcaatttagc agatagaatg cttggattgt ctggagtgca ggaaattaag
2941 gaacagggtg ttggactgat agcagagtgt agaactttct tggattctat tgctgggact
3001 ttgaaatcta tgatgtttgg gtttcatcat tctgtgactg ttgaaattat aaatactgtg
3061 ctttgttttg ttaagagtgg aatcctgctt tatgtcatac aacaattgaa ccaagatgaa
```

FIGURE 3 (Continued)

```
3121 cactctcaca taattggttt gttgagagtt atgaattatg cagatattgg ctgttcagtt
3181 atttcatgtg gtaaagtttt ttccaaaatg ttagaaacag tttttaattg gcaaatggat
3241 tctagaatga tggagctgag gactcagagc ttctctaatt ggttaagaga tatttgttca
3301 ggaattacta tttttaaaag ttttaaggat gccatatatt ggttatatac aaaattgaag
3361 gatttttatg aagtaaatta tggcaagaaa aaggatattc ttaatattct caaagataat
3421 cagcaaaaaa tagaaaaagc cattgaagaa gcagacaatt tttgcatttt gcaaattcaa
3481 gatgtagaga aatttgatca gtatcagaaa ggggttgatt taatacaaaa gctgagaact
3541 gtccattcaa tggcgcaagt tgacccaat ttggggttc atttgtcacc tctcagagat
3601 tgcatagcaa gagtccacca aaagctcaag aatcttggat ctataaatca ggccatggta
3661 acaagatgtg agccagttgt ttgctatttg tatggcaaaa gagggggagg gaaaagcttg
3721 acttcaattg cattggcaac caaaatttgt aaacactatg gtgttgaacc tgagaaaaat
3781 atttacacca aacctgtggc ctcagattat tgggatggat atagtggaca attagtttgc
3841 attattgatg atattggcca aaacacaaca gatgaagatt ggtcagattt ttgtcaatta
3901 gtgtcaggat gcccaatgag attgaatatg gcttctctag aggagaaggg cagacatttt
3961 tcctctcctt ttataatagc aacttcaaat tggtcaaatc caagtccaaa aacagtttat
4021 gttaaggaag caattgatcg taggcttcat tttaaggttg aagttaaacc tgcttcattt
4081 tttaaaaatc ctcacaatga tatgttgaat gttaatttgg ccaaaacaaa tgatgcaatt
4141 aaggacatgt cttgtgttga tttaataatg gatggacaca atatttcatt gatggattta
4201 cttagttcct tagtgatgac agttgaaatt aggaaacaga atatgagtga attcatggag
4261 ttgtggtctc agggaatttc agatgatgac aatgatagtg cagtggctga gttttccag
4321 tcttttccat ctggtgaacc atcaaattgg aagttatcta gttttttcca atctgtcact
4381 aatcacaagt gggttgctgt gggagctgca gttggcattc ttggagtgct tgtgggagga
4441 tggtttgtgt ataagcattt tcccgcaaa gaggaagaac caattccagc tgaaggggtt
4501 tatcatggcg tgactaagcc caaacaagtg attaaattgg atgcagatcc agtagagtcc
4561 cagtcaactc tagaaatagc aggattagtt aggaaaaatc tggttcagtt tggagttggt
4621 gagaaaaatg gatgtgtgag atgggtcatg aatgccttag gagtgaagga tgattggttg
4681 ttagtacctt ctcatgctta taaatttgaa aaggattatg aaatgatgga gttttacttc
4741 aatagaggtg gaacttacta ttcaattca gctggtaatg ttgttattca atctttagat
4801 gtgggatttc aagatgttgt tttaatgaag gtttctacaa ttcccaagtt tagagatatt
4861 actcaacact ttattaagaa aggagatgtg cctagagcct taaatcgctt ggcaacatta
4921 gtgacaaccg ttaatggaac tcctatgtta atttctgagg gaccattaaa gatggaagaa
4981 aaagccactt atgttcataa gaagaatgat ggtactacag ttgatttgac tgtagatcag
5041 gcatggagag gaaaaggtga aggtcttcct ggaatgtgtg gtggggccct agtgtcatca
5101 aatcagtcca tacagaatgc aatttttggt attcatgttg ctggaggaaa ttcaattctt
5161 gtggcaaagc tggttactca agaaatgttt caaacattg ataagaaaat tgaaagtcag
5221 agaataatga aagtggaatt tactcaatgt tcaatgaatg tagtctccaa aacgcttttt
5281 agaaagagtc ccattcatca ccacattgat agaaccatga ttaattttcc tgcagctatg
5341 cctttctcta aagctgaaat tgatccaatg gctatgatgt tgtccaaata ttcattacct
5401 attgtggagg aaccagagga ttacaaggaa gcttcagttt tttatcaaaa caaaatagta
5461 ggcaagactc agctagttga tgactttta gatcttgata tggctattac aggggctcca
5521 ggcattgatg ctatcaatat ggattcatct cctgggtttc cttatgttca agaaaaattg
5581 accaaaagag atttaatttg gttggatgaa aatggtttgc tgttaggagt tcacccaaga
5641 ttggcccaga gaattttatt taatactgtc atgatggaaa attgttctga cttagatgtt
5701 gttttttacaa cttgtccaaa agatgaattg agaccattag aaaaagtttt ggaatcaaaa
5761 acaagagcca ttgatgcttg tcctttggat tatacaattc tatgtcgaat gtattgggt
5821 ccagctatca gttatttcca tttgaatcca gggtttcaca caggtgttgc tattggcata
5881 gatcctgata gacagtggga tgaattattt aaaacaatga taagatttgg agatgttggt
5941 cttgatttag attttctctgc ttttgatgcc agtcttagtc catttatgat tagggaagca
6001 ggtagaatca tgagtgaatt atctggaaca ccatctcatt ttggaacagc tcttatcaat
6061 actatcattt attctaaaca tctgctgtac aactgttgtt atcatgtttg tggttcaatg
6121 ccttctgggt ctccttgcac agctttgttg aattcaatta ttaataatat taatctgtat
```

Page 2

FIGURE 3 (Continued)

```
6181 tatgtgtttt ctaaaatatt tggaaagtct ccagttttct tttgtcaagc tttgaggatc
6241 ctttgttacg gagatgatgt tttgatagtt ttttccagag atgttcaaat tgacaatctt
6301 gacttgattg gacagaaaat tgtagatgag ttcaaaaaac ttggcatgac agccacctca
6361 gctgataaaa atgtgcctca actgaagcca gtttcagaat tgacttttct caaaagatct
6421 ttcaatttgg tggaggatag aattagacct gcaatttcag aaaagacaat ttggtctttg
6481 atggcttggc agagaagtaa cgctgagttt gagcggaatt tagaaaatgc tcagtggttt
6541 gcttttatgc atggctatga gttctatcag aaatttatt attttgttca gtcctgtttg
6601 gagaaagaga tgatagaata tagacttaaa tcttatgatt ggtggagaat gagattttat
6661 gaccagtgtt tcatttgtga cctttcatga gcatgc
```

FIGURE 4

```
   1 ggtaccatga atatgtccaa acaaggaatt ttccagactg ttgggagtgg ccttgaccac
  61 atcctgtctt tggcagatat tgaggaagag caaatgattc agtccgttga taggactgca
 121 gtgactggag cttcttactt cacttctgtg gaccaatctt cagttcatac tgctgaggtt
 181 ggctcacatc aaattgaacc tttgaaaacc tctgttgata aacctggttc taagaaaact
 241 caggggaaa  agttttcct  gattcattct gctgattggc tcactacaca tgctctcttt
 301 catgaagttg caaaattgga tgtggtgaaa ctactgtata atgagcagtt gccgtccaa
 361 ggtttgttga gataccatac atatgcaaga tttggcattg agattcaagt tcagataaat
 421 cccacaccct ttcagcaagg aggactaatt tgtgccatgg ttcctggtga ccaaagttat
 481 ggttcaatag catccttgac tgtttatcct catggtctgt taaattgcaa tatcaacaat
 541 gtagttagaa taaggttcc  atttatttat actagaggtg cttatcattt taaagatcca
 601 cagtacccag tttgggaatt gacaatcaga gttggtcag  agttgaatat tggaacagga
 661 acttcagctt acacttcact caatgtttta gctaggttta cagatttgga gttgcatgga
 721 ttaactcctc tttctacaca gatgatgaga aatgaattta gggtcagtac tactgaaaat
 781 gttgtaaatt tgtcaaatta tgaagatgca agggcaaaaa tgtcttttgc tttggatcag
 841 gaagattgga agtctgatcc ttcccaaggt ggtggaatta aaattactca ttttactacc
 901 tggacatcca ttccaacctt agctgctcag tttccattta atgcttcaga ttcagttgga
 961 caacaaatta aagttattcc agtggaccca tactttttcc aaatgacaaa cactaatcct
1021 gatcaaaaat gtataactgc cttggcctct atttgtcaga tgttctgctt tggaggggga
1081 gatcttgttt ttgattttca ggttttcca  accaaatatc attcaggtag actgttgttt
1141 tgttttgttc ctgggaatga gttaatagat gttactggaa ttacattaaa acaggcaact
1201 actgctcctt gtgcagtgat ggacattaca ggagtgcagt caaccttgag atttcgtgtt
1261 ccttggattt ctgatacacc ttatcgagtg aataggtaca cgaagtcagc acatcaaaaa
1321 ggtgagtaca ctgccattgg gaagcttatt gtgtattgtt ataacagact gacttctcct
1381 tctaatgttg cctctcatgt tagagttaat gtttatcttt cagcaattaa tttggaatgt
1441 tttgctcctc tttaccatgc tatggatgtt actacacagg ttggagatga ttcaggaggt
1501 ttctcaacaa cagtttctac agagcagaat gttcctgatc cccaagttgg gataacaacc
1561 atgagggatt taaaaggaaa agccaatagg ggaaagatgg atgtttcagg agtgcaagca
1621 cctcgtggga gctatcagca acaattgaac gatccagttt tagcaaagaa agtacctgag
1681 acatttcctg aattgaagcc tggagagtcc agacatacat cagatcacat gtctatttat
1741 aaattcatgg gaaggtctca tttttgtgc  acttttactt tcaattcaaa taataaagag
1801 tacacatttc caataaccct gtcttcgact tctaatcctc ctcatggttt accatcaaca
1861 ttaaggtggt tcttcaattt gtttcagttg tatagaggac cattggattt aacaattata
1921 atcacaggag ccactgatgt ggatggtatg gcctggttta ctccagtggg ccttgctgtc
1981 gacccttggg tggaaaagga gtcagctttg tctattgatt ataaaactgc ccttggagct
2041 gttagattta atacaagaag aacaggaaac attcaaatta gattgccgtg gtattcttat
2101 ttgtatgccg tgtctggagc actggatggc tggggggata agacagattc tacatttgga
2161 ttgtttctat tcgagattgc aaaattacaat cattctgatg aatatttgtc cttcagttgt
2221 tatttgtctg tcacagagca atcagagttc tatttttccta gagctccatt aaattcaaat
2281 gctatgttgt ccactgaatc catgatgagt agaattgcag ctggagactt ggagtcatca
2341 gtggatgatc ccagatcaga ggaggataga agatttgaga gtcatataga atgtaggaaa
2401 ccatacaaag aattgagact ggaggttggg aaacaaagac tcaaatatgc tcaggaagag
2461 ttatcaaatg aagtgcttcc acctcctagg aaaatgaagg ggttattttc acaagctaaa
2521 atttctcttt tttatactga ggagcatgaa ataatgaagt tttcttggag aggagtgact
2581 gctgatacta gggctttgag aagatttgga ttctctctgg ctgctggtag aagtgtgtgg
2641 actcttgaaa tggatgctgg agttcttact ggaagattga tcagattgaa tgatgagaaa
2701 tggacagaaa tgaaggatga taagattgtt tcattaattg aaaagttcac aagcaataaa
2761 tattggtcta aagtgaattt tccacatgga atgttggatc ttgaagaaat tgctgccaat
2821 tctaaggatt ttccaaatat gtctgagaca gatttgtgtt tcctgttaca ttggctaaat
2881 ccaaagaaaa tcaatttagc agatagaatg cttggattgt ctggagtgca ggaaattaag
2941 gaacagggtg ttggactgat agcagagtgt agaactttct tggattctat tgctgggact
3001 ttgaaatcta tgatgtttgg gtttcatcat tctgtgactg ttgaaattat aaatactgtg
3061 ctttgttttg ttaagagtgg aatcctgctt tatgtcatac aacaattgaa ccaagatgaa
```

FIGURE 4 (Continued)

```
3121 cactctcaca taattggttt gttgagagtt atgaattatg cagatattgg ctgttcagtt
3181 atttcatgtg gtaaagtttt ttccaaaatg ttagaaacag tttttaattg gcaaatggat
3241 tctagaatga tggagctgag gactcagagc ttctctaatt ggttaagaga tatttgttca
3301 ggaattacta tttttaaaag ttttaaggat gccatatatt ggttatatac aaaattgaag
3361 gatttttatg aagtaaatta tggcaagaaa aaggatattc ttaatattct caaagataat
3421 cagcaaaaaa tagaaaaagc cattgaagaa gcagacaatt tttgcatttt gcaaattcaa
3481 gatgtagaga atttgatca gtatcagaaa ggggttgatt taatacaaaa gctgagaact
3541 gtccattcaa tggcgcaagt tgacccaat ttgggggttc atttgtcacc tctcagagat
3601 tgcatagcaa gagtccacca aaagctcaag aatcttggat ctataaatca ggccatggta
3661 acaagatgtg agccagttgt ttgctatttg tatggcaaaa gaggggagg gaaaagcttg
3721 acttcaattg cattggcaac caaaatttgt aaacactatg gtgttgaacc tgagaaaaat
3781 atttacacca aacctgtggc ctcagattat tgggatggat atagtggaca attagtttgc
3841 attattgatg atattggcca aaacacaaca gatgaagatt ggtcagattt ttgtcaatta
3901 gtgtcaggat gcccaatgag attgaatatg gcttctctag aggagaaggg cagacatttt
3961 tcctctcctt ttataatagc aacttcaaat tggtcaaatc caagtccaaa aacagtttat
4021 gttaaggaag caattgatcg taggcttcat tttaaggttg aagttaaacc tgcttcattt
4081 tttaaaaatc ctcacaatga tatgttgaat gttaatttgg ccaaaacaaa tgatgcaatt
4141 aaggacatgt cttgtgttga tttaataatg gatggacaca atatttcatt gatggattta
4201 cttagttcct tagtgatgac agttgaaatt aggaaacaga atatgagtga attcatggag
4261 ttgtggtctc agggaatttc agatgatgac aatgatagtg cagtggctga gtttttccag
4321 tcttttccat ctggtgaacc atcaaattgg aagttatcta gttttttcca atctgtcact
4381 aatcacaagt gggttgctgt gggagctgca gttggcattc ttggagtgct tgtgggagga
4441 tggtttgtgt ataagcattt tcccgcaaa gaggaagaac caattccagc tgaagggtt
4501 tatcatggcg tgactaagcc caaacaagtg attaaattgg atgcagatcc agtagagtcc
4561 cagtcaactc tagaaatagc aggattagtt aggaaaaatc tggttcagtt tggagttggt
4621 gagaaaaatg gatgtgtgag atgggtcatg aatgccttag gagtgaagga tgattggttg
4681 ttagtacctt ctcatgctta taaatttgaa aaggattatg aaatgatgga gttttacttc
4741 aatagaggtg gaacttacta ttcaatttca gctggtaatg ttgttattca atctttagat
4801 gtgggatttc aagatgttgt tttaatgaag gtttctacaa ttcccaagtt tagagatatt
4861 actcaacact ttattaagaa aggagatgtg cctagagcct taaatcgctt ggcaacatta
4921 gtgacaaccg ttaatggaac tcctatgtta atttctgagg gaccattaaa gatggaagaa
4981 aaagccactt atgttcataa gaagaatgat ggtactacag ttgatttgac tgtagatcag
5041 gcatggagag gaaaaggtga aggtcttcct ggaatgtgtg gtggggccct agtgtcatca
5101 aatcagtcca tacagaatgc aatttgggt attcatgttg ctggaggaaa ttcaattctt
5161 gtggcaaagc tggttactca agaaatgttt caaaacattg ataagaaaat tgaaagtcag
5221 agaataatga agtggaatt tactcaatgt tcaatgaatg tagtctccaa aacgcttttt
5281 agaaagagtc ccattcatca ccacattgat agaaccatga ttaattttcc tgcagctatg
5341 cctttctcta aagctgaaat tgatccaatg gctatgatgt tgtccaaata ttcattacct
5401 attgtggagg aaccagagga ttacaaggaa gcttcagttt tttatcaaaa caaaatagta
5461 ggcaagactc agctagttga tgacttttta gatcttgata tggctattac aggggctcca
5521 ggcattgatg ctatcaatat ggattcatct cctgggtttc cttatgttca agaaaaattg
5581 accaaaagag atttaatttg gttggatgaa aatggtttgc tgttaggagt tcacccaaga
5641 ttgcccagga gaattttatt taatactgtc atgatggaaa attgttctga cttagatgtt
5701 gttttttacaa cttgtccaaa agatgaattg agaccattag aaaaagtttt ggaatcaaaa
5761 acaagagcca ttgatgcttg tcctttggat tatacaattc tatgtcgaat gtattgggt
5821 ccagctatca gttatttcca tttgaatcca gggtttcaca caggtgttgc tattggcata
5881 gatcctgata gacagtggga tgaattattt aaaacaatga taagatttgg agatgttggt
5941 cttgatttag atttctctgc ttttgatgcc agtcttagtc catttatgat tagggaagca
6001 ggtagaatca tgagtgaatt atctggaaca ccatctcatt ttggaacagc tcttataat
6061 actatcattt attctaaaca tctgctgtac aactgttgtt atcatgtttg tggttcaatg
6121 ccttctgggt ctccttgcac agctttgtt aattcaatta ttaataatat taatctgtat
6181 tatgtgtttt ctaaaatatt tggaaagtct ccagttttct tttgtcaagc tttgaggatc
```

FIGURE 4 (Continued)

```
6241 ctttgttacg gagatgatgt tttgatagtt ttttccagag atgttcaaat tgacaatctt
6301 gacttgattg gacagaaaat tgtagatgag ttcaaaaaac ttggcatgac agccacctca
6361 gctgataaaa atgtgcctca actgaagcca gtttcagaat tgactttct caaaagatct
6421 ttcaatttgg tggaggatag aattagacct gcaatttcag aaaagacaat ttggtctttg
6481 atggcttggc agagaagtaa cgctgagttt gagcagaatt tagaaaatgc tcagtggttt
6541 gcttttatgc atggctatga gttctatcag aaatttatt attttgttca gtcctgtttg
6601 gagaaagaga tgatagaata tagacttaaa tcttatgatt ggtggagaat gagattttat
6661 gaccagtgtt tcatttgtga cctttcatga tttgtttaaa caaattttct tactctttct
6721 gaggtttgtt tatttctttt gtccgctaac tgcatgc
```

Figure 5

```
  1                                        10                                              20
  M    N    M    S    K    Q    G    I    F    R    T    V    G    S    G    L    D    H    I    L
 ATG  AAT  ATG  TCC  AAA  CAA  GGA  ATT  TTC  CGG  ACT  GTT  GGG  AGT  GGC  CTT  GAC  CAC  ATC  CTG 30                                              40
  S    L    A    D    I    E    E    E    Q    M    I    Q    S    V    D    R    T    A    V    T
 TCT  TTG  GCA  GAT  ATT  GAG  GAA  GAG  CAA  ATG  ATT  CAG  TCC  GTT  GAT  AGG  ACT  GCA  GTG  ACT 50                                              60
  G    A    S    Y    F    T    S    V    D    Q    S    S    V    H    T    A    E    V    G    S
 GGA  GCT  TCT  TAC  TTC  ACT  TCT  GTG  GAC  CAA  TCT  TCA  GTT  CAT  ACT  GCT  GAG  GTT  GGC  TCA 70                                              80
  H    Q    I    E    P    L    K    T    S    V    D    K    P    G    S    K    K    T    Q    G
 CAT  CAA  ATT  GAA  CCT  TTG  AAA  ACC  TCT  GTT  GAT  AAA  CCT  GGT  TCT  AAG  AAA  ACT  CAG  GGG 90                                             100
  E    K    F    F    L    I    H    S    A    D    W    L    T    T    H    A    L    F    H    E
 GAA  AAG  TTT  TTC  CTG  ATT  CAT  TCT  GCT  GAT  TGG  CTC  ACT  ACA  CAT  GCT  CTC  TTT  CAT  GAA 110                                             120
  V    A    K    L    D    V    V    K    L    L    Y    N    E    Q    F    A    V    Q    G    L
 GTT  GCA  AAA  TTG  GAT  GTG  GTG  AAA  CTA  CTG  TAT  AAT  GAG  CAG  TTT  GCC  GTC  CAA  GGT  TTG 130                                             140
  L    R    Y    H    T    Y    A    R    F    G    I    E    I    Q    V    Q    I    N    P    T
 TTG  AGA  TAC  CAT  ACA  TAT  GCA  AGA  TTT  GGC  ATT  GAG  ATT  CAA  GTT  CAG  ATA  AAT  CCC  ACA 150                                             160
  P    F    Q    Q    G    G    L    I    C    A    M    V    P    G    D    Q    S    Y    G    S
 CCC  TTT  CAG  CAA  GGA  GGA  CTA  ATT  TGT  GCC  ATG  GTT  CCT  GGT  GAC  CAA  AGT  TAT  GGT  TCA 170                                             180
  I    A    S    L    T    V    Y    P    H    G    L    L    N    C    N    I    N    N    V    V
 ATA  GCA  TCC  TTG  ACT  GTT  TAT  CCT  CAT  GGT  CTG  TTA  AAT  TGC  AAT  ATC  AAC  AAT  GTA  GTT 190                                             200
  R    I    K    V    P    F    I    Y    T    R    G    A    Y    H    F    K    D    P    Q    Y
 AGA  ATA  AAG  GTT  CCA  TTT  ATT  TAT  ACT  AGA  GGT  GCT  TAT  CAT  TTT  AAA  GAT  CCA  CAG  TAC 210                                             220
  P    V    W    E    L    T    I    R    V    W    S    E    L    N    I    G    T    G    T    S
 CCA  GTT  TGG  GAA  TTG  ACA  ATC  AGA  GTT  TGG  TCA  GAG  TTG  AAT  ATT  GGA  ACA  GGA  ACT  TCA 230                                             240
  A    Y    T    S    L    N    V    L    A    R    F    T    D    L    E    L    H    G    L    T
 GCT  TAC  ACT  TCA  CTC  AAT  GTT  TTA  GCT  AGG  TTT  ACA  GAT  TTG  GAG  TTG  CAT  GGA  TTA  ACT 250                                             260
```

FIGURE 5 (Continued)

```
  P   L   S   T   Q   M   M   R   N   E   F   R   V   S   T   T   E   N   V   V
CCT CTT TCT ACA CAG ATG ATG AGA AAT GAA TTT AGG GTC AGT ACT ACT GAA AAT GTT GTA
                                270                                         280
  N   L   S   N   Y   E   D   A   R   A   K   M   S   F   A   L   D   Q   E   D
AAT TTG TCA AAT TAT GAA GAT GCA AGG GCA AAA ATG TCT TTT GCT TTG GAT CAG GAA GAT
                                290                                         300
  W   K   S   D   P   S   Q   G   G   G   I   K   I   T   H   F   T   T   W   T
TGG AAG TCT GAT CCT TCC CAA GGT GGT GGA ATT AAA ATT ACT CAT TTT ACT ACC TGG ACA
                                310                                         320
  S   I   P   T   L   A   A   Q   F   P   F   N   A   S   D   S   V   G   Q   Q
TCC ATT CCA ACC TTA GCT GCT CAG TTT CCA TTT AAT GCT TCA GAT TCA GTT GGA CAA CAA
                                330                                         340
  I   K   V   I   P   V   D   P   Y   F   F   Q   M   T   N   T   N   P   D   Q
ATT AAA GTT ATT CCA GTG GAC CCA TAC TTT TTC CAA ATG ACA AAC ACT AAT CCT GAT CAA
                                350                                         360
  K   C   I   T   A   L   A   S   I   C   Q   M   F   C   F   W   R   G   D   L
AAA TGT ATA ACT GCC TTG GCC TCT ATT TGT CAG ATG TTC TGC TTT TGG AGG GGA GAT CTT
                                370                                         380
  V   F   D   F   Q   V   F   P   T   K   Y   H   S   G   R   L   L   F   C   F
GTT TTT GAT TTT CAG GTT TTT CCA ACC AAA TAT CAT TCA GGT AGA CTG TTG TTT TGT TTT
                                390                                         400
  V   P   G   N   E   L   I   D   V   T   G   I   T   L   K   Q   A   T   T   A
GTT CCT GGG AAT GAG TTA ATA GAT GTT ACT GGA ATT ACA TTA AAA CAG GCA ACT ACT GCT
                                410                                         420
  P   C   A   V   M   D   I   T   G   V   Q   S   T   L   R   F   R   V   P   W
CCT TGT GCA GTG ATG GAC ATT ACA GGA GTG CAG TCA ACC TTG AGA TTT CGT GTT CCT TGG
                                430                                         440
  I   S   D   T   P   Y   R   V   N   R   Y   T   K   S   A   H   Q   K   G   E
ATT TCT GAT ACA CCT TAT CGA GTG AAT AGG TAC ACG AAG TCA GCA CAT CAA AAA GGT GAG
                                450                                         460
  Y   T   A   I   G   K   L   I   V   Y   C   Y   N   R   L   T   S   P   S   N
TAC ACT GCC ATT GGG AAG CTT ATT GTG TAT TGT TAT AAC AGA CTG ACT TCT CCT TCT AAT
                                470                                         480
  V   A   S   H   V   R   V   N   V   Y   L   S   A   I   N   L   E   C   F   A
GTT GCC TCT CAT GTT AGA GTT AAT GTT TAT CTT TCA GCA ATT AAT TTG GAA TGT TTT GCT
                                490                                         500
  P   L   Y   H   A   M   D   V   T   T   Q   V   G   D   D   S   G   G   F   S
```

FIGURE 5 (Continued)

```
    CCT CTT TAC CAT GCT ATG GAT GTT ACT ACA CAG GTT GGA GAT GAT TCA GGA GGT TTC TCA
                                        510                                     520
     T   T   V   S   T   E   Q   N   V   P   D   P   Q   V   G   I   T   T   M   R
    ACA ACA GTT TCT ACA GAG CAG AAT GTT CCT GAT CCC CAA GTT GGG ATA ACA ACC ATG AGG
                                        530                                     540
     D   S   K   G   K   A   N   R   G   K   M   D   V   S   G   V   Q   A   P   V
    GAT TCA AAA GGA AAA GCC AAT AGG GGA AAG ATG GAT GTT TCA GGA GTG CAA GCA CCT GTG
                                        550                                     560
     G   A   I   T   T   I   E   D   P   V   L   A   K   K   V   P   E   T   F   P
    GGA GCT ATC ACA ACA ATT GAA GAT CCA GTT TTA GCA AAG AAA GTA CCT GAG ACA TTT CCT
                                        570                                     580
     E   L   K   P   G   E   S   R   H   T   S   D   H   M   S   I   Y   K   F   M
    GAA TTG AAG CCT GGA GAG TCC AGA CAT ACA TCA GAT CAC ATG TCT ATT TAT AAA TTC ATG
                                        590                                     600
     G   R   S   H   F   L   C   T   F   T   F   N   S   N   N   K   E   Y   T   F
    GGA AGG TCT CAT TTT TTG TGC ACT TTT ACT TTC AAT TCA AAT AAT AAA GAG TAC ACA TTT
                                        610                                     620
     P   I   T   L   S   S   T   S   N   P   P   H   G   L   P   S   T   L   R   W
    CCA ATA ACC CTG TCT TCG ACT TCT AAT CCT CCT CAT GGT TTA CCA TCA ACA TTA AGG TGG
                                        630                                     640
     F   F   N   L   F   Q   L   Y   R   G   P   L   D   L   T   I   I   I   T   G
    TTC TTC AAT TTG TTT CAG TTG TAT AGA GGA CCA TTG GAT TTA ACA ATT ATA ATC ACA GGA
                                        650                                     660
     A   T   D   V   D   G   M   A   W   F   T   P   V   G   L   A   V   D   T   P
    GCC ACT GAT GTG GAT GGT ATG GCC TGG TTT ACT CCA GTG GGC CTT GCT GTC GAC ACC CCT
                                        670                                     680
     W   V   E   K   E   S   A   L   S   I   D   Y   K   T   A   L   G   A   V   R
    TGG GTG GAA AAG GAG TCA GCT TTG TCT ATT GAT TAT AAA ACT GCC CTT GGA GCT GTT AGA
                                        690                                     700
     F   N   T   R   R   T   G   I   I   Q   I   R   L   P   W   Y   S   Y   L   Y
    TTT AAT ACA AGA AGA ACA GGA ATC ATC CAA ATT AGA TTG CCG TGG TAT TCT TAT TTG TAT
                                        710                                     720
     A   V   S   G   A   L   D   G   L   G   D   K   T   D   S   T   F   G   L   V
    GCC GTG TCT GGA GCA CTG GAT GGC TTG GGG GAT AAG ACA GAT TCT ACA TTT GGA TTG GTT
                                        730                                     740
     S   I   Q   I   A   N   Y   N   H   S   D   E   Y   L   S   F   S   C   Y   L
    TCT ATT CAG ATT GCA AAT TAC AAT CAT TCT GAT GAA TAT TTG TCC TTC AGT TGT TAT TTG
```

Page 3

FIGURE 5 (Continued)

```
                          750                                            760
  S   V   T   E   Q   S   E   F   Y   F   P   R   A   P   L   N   S   N   A   M
TCT GTC ACA GAG CAA TCA GAG TTC TAT TTT CCT AGA GCT CCA TTA AAT TCA AAT GCT ATG 770                                    780
  L   S   T   E   S   M   M   S   R   I   A   A   G   D   L   E   S   S   V   D
TTG TCC ACT GAA TCC ATG ATG AGT AGA ATT GCA GCT GGA GAC TTG GAG TCA TCA GTG GAT 790                                            800
  D   P   R   S   E   E   D   R   R   F   E   S   H   I   E   C   R   K   P   Y
GAT CCC AGA TCA GAG GAG GAT AGA AGA TTT GAG AGT CAT ATA GAA TGT AGG AAA CCA TAC 810                            820
  K   E   L   R   L   E   V   G   K   Q   R   L   K   Y   A   Q   E   E   L   S
AAA GAA TTG AGA CTG GAG GTT GGG AAA CAA AGA CTC AAA TAT GCT CAG GAA GAG TTA TCA 830                    836
  N   E   V   L   P   P   P   R   K   I   K   G   L   F   S   Q
AAT GAA GTG CTT CCA CCT CCT AGG AAA ATC AAG GGG TTA TTT TCA CAA
```

Figure 6

```
  1                                          10                                          20
  M   N   M   S   K   Q   G   I   F   Q   T   V   G   S   G   L   D   H   I   L
  ATG AAT ATG TCC AAA CAA GGA ATT TTC CAG ACT GTT GGG AGT GGC CTT GAC CAC ATC CTG 30                                          40
  S   L   A   D   I   E   E   Q   M   I   Q   S   V   D   R   T   A   V   T
  TCT TTG GCA GAT ATT GAG GAA GAG CAA ATG ATT CAG TCC GTT GAT AGG ACT GCA GTG ACT 50                                          60
  G   A   S   Y   F   T   S   V   D   Q   S   S   V   H   T   A   E   V   G   S
  GGA GCT TCT TAC TTC ACT TCT GTG GAC CAA TCT TCA GTT CAT ACT GCT GAG GTT GGC TCA 70                                          80
  H   Q   I   E   P   L   K   T   S   V   D   K   P   G   S   K   K   T   Q   G
  CAT CAA ATT GAA CCT TTG AAA ACC TCT GTT GAT AAA CCT GGT TCT AAG AAA ACT CAG GGG 90                                         100
  E   K   F   F   L   I   H   S   A   D   W   L   T   T   H   A   L   F   H   E
  GAA AAG TTT TTC CTG ATT CAT TCT GCT GAT TGG CTC ACT ACA CAT GCT CTC TTT CAT GAA 110                                         120
  V   A   K   L   D   V   V   K   L   L   Y   N   E   Q   F   A   V   Q   G   L
  GTT GCA AAA TTG GAT GTG GTG AAA CTA CTG TAT AAT GAG CAG TTT GCC GTC CAA GGT TTG 130                                         140
  L   R   Y   H   T   Y   A   R   F   G   I   E   I   Q   V   Q   I   N   P   T
  TTG AGA TAC CAT ACA TAT GCA AGA TTT GGC ATT GAG ATT CAA GTT CAG ATA AAT CCC ACA 150                                         160
  P   F   Q   Q   G   G   L   I   C   A   M   V   P   G   D   Q   S   Y   G   S
  CCC TTT CAG CAA GGA GGA CTA ATT TGT GCC ATG GTT CCT GGT GAC CAA AGT TAT GGT TCA 170                                         180
  I   A   S   L   T   V   Y   P   H   G   L   L   N   C   N   I   N   N   V   V
  ATA GCA TCC TTG ACT GTT TAT CCT CAT GGT CTG TTA AAT TGC AAT ATC AAC AAT GTA GTT 190                                         200
  R   I   K   V   P   F   I   Y   T   R   G   A   Y   H   F   K   D   P   Q   Y
  AGA ATA AAG GTT CCA TTT ATT TAT ACT AGA GGT GCT TAT CAT TTT AAA GAT CCA CAG TAC 210                                         220
  P   V   W   E   L   T   I   R   V   W   S   E   L   N   I   G   T   G   T   S
  CCA GTT TGG GAA TTG ACA ATC AGA GTT TGG TCA GAG TTG AAT ATT GGA ACA GGA ACT TCA 230                                         240
  A   Y   T   S   L   N   V   L   A   R   F   T   D   L   E   L   H   G   L   T
  GCT TAC ACT TCA CTC AAT GTT TTA GCT AGG TTT ACA GAT TTG GAG TTG CAT GGA TTA ACT 250                                         260
  P   L   S   T   Q   M   M   R   N   E   F   R   V   S   T   T   E   N   V   V
  CCT CTT TCT ACA CAG ATG ATG AGA AAT GAA TTT AGG GTC AGT ACT ACT GAA AAT GTT GTA
```

FIGURE 6 (Continued)

```
                                                 270                                                 280
         N   L   S   N   Y   E   D   A   R   A   K   M   S   F   A   L   D   Q   E   D
        AAT TTG TCA AAT TAT GAA GAT GCA AGG GCA AAA ATG TCT TTT GCT TTG GAT CAG GAA GAT 290                                                 300
         W   K   S   D   P   S   Q   G   G   G   I   K   I   T   H   F   T   T   W   T
        TGG AAG TCT GAT CCT TCC CAA GGT GGT GGA ATT AAA ATT ACT CAT TTT ACT ACC TGG ACA 310                                                 320
         S   I   P   T   L   A   A   Q   F   P   F   N   A   S   D   S   V   G   Q   Q
        TCC ATT CCA ACC TTA GCT GCT CAG TTT CCA TTT AAT GCT TCA GAT TCA GTT GGA CAA CAA 330                                                 340
         I   K   V   I   P   V   D   P   Y   F   F   Q   M   T   N   T   N   P   D   Q
        ATT AAA GTT ATT CCA GTG GAC CCA TAC TTT TTC CAA ATG ACA AAC ACT AAT CCT GAT CAA 350                                                 360
         K   C   I   T   A   L   A   S   I   C   Q   M   F   C   F   W   R   G   D   L
        AAA TGT ATA ACT GCC TTG GCC TCT ATT TGT CAG ATG TTC TGC TTT TGG AGG GGA GAT CTT 370                                                 380
         V   F   D   F   Q   V   F   P   T   K   Y   H   S   G   R   L   L   F   C   F
        GTT TTT GAT TTT CAG GTT TTT CCA ACC AAA TAT CAT TCA GGT AGA CTG TTG TTT TGT TTT 390                                                 400
         V   P   G   N   E   L   I   D   V   T   G   I   T   L   K   Q   A   T   T   A
        GTT CCT GGG AAT GAG TTA ATA GAT GTT ACT GGA ATT ACA TTA AAA CAG GCA ACT ACT GCT 410                                                 420
         P   C   A   V   M   D   I   T   G   V   Q   S   T   L   R   F   R   V   P   W
        CCT TGT GCA GTG ATG GAC ATT ACA GGA GTG CAG TCA ACC TTG AGA TTT CGT GTT CCT TGG 430                                                 440
         I   S   D   T   P   Y   R   V   N   R   Y   T   K   S   A   H   Q   K   G   E
        ATT TCT GAT ACA CCT TAT CGA GTG AAT AGG TAC ACG AAG TCA GCA CAT CAA AAA GGT GAG 450                                                 460
         Y   T   A   I   G   K   L   I   V   Y   C   Y   N   R   L   T   S   P   S   N
        TAC ACT GCC ATT GGG AAG CTT ATT GTG TAT TGT TAT AAC AGA CTG ACT TCT CCT TCT AAT 470                                                 480
         V   A   S   H   V   R   V   N   V   Y   L   S   A   I   N   L   E   C   F   A
        GTT GCC TCT CAT GTT AGA GTT AAT GTT TAT CTT TCA GCA ATT AAT TTG GAA TGT TTT GCT 490                                                 500
         P   L   Y   H   A   M   D   V   T   T   Q   V   G   D   D   S   G   G   F   S
        CCT CTT TAC CAT GCT ATG GAT GTT ACT ACA CAG GTT GGA GAT GAT TCA GGA GGT TTC TCA 510                                                 520
         T   T   V   S   T   E   Q   N   V   P   D   P   Q   V   G   I   T   T   M   R
```

Page 2

FIGURE 6 (Continued)

```
ACA ACA GTT TCT ACA GAG CAG AAT GTT CCT GAT CCC CAA GTT GGG ATA ACA ACC ATG AGG
                                    530                                         540
 D   L   K   G   K   A   N   R   G   K   M   D   V   S   G   V   Q   A   P   V
GAT TTA AAA GGA AAA GCC AAT AGG GGA AAG ATG GAT GTT TCA GGA GTG CAA GCA CCT GTG
                                    550                                         560
 G   A   I   T   T   I   E   D   P   V   L   A   K   K   V   P   E   T   F   P
GGA GCT ATC ACA ACA ATT GAA GAT CCA GTT TTA GCA AAG AAA GTA CCT GAG ACA TTT CCT
                                    570                                         580
 E   L   K   P   G   E   S   R   H   T   S   D   H   M   S   I   Y   K   F   M
GAA TTG AAG CCT GGA GAG TCC AGA CAT ACA TCA GAT CAC ATG TCT ATT TAT AAA TTC ATG
                                    590                                         600
 G   R   S   H   F   L   C   T   F   T   F   N   S   N   N   K   E   Y   T   F
GGA AGG TCT CAT TTT TTG TGC ACT TTT ACT TTC AAT TCA AAT AAT AAA GAG TAC ACA TTT
                                    610                                         620
 P   I   T   L   S   S   T   S   N   P   P   H   G   L   P   S   T   L   R   W
CCA ATA ACC CTG TCT TCG ACT TCT AAT CCT CCT CAT GGT TTA CCA TCA ACA TTA AGG TGG
                                    630                                         640
 F   F   N   L   F   Q   L   Y   R   G   P   L   D   L   T   I   I   I   T   G
TTC TTC AAT TTG TTT CAG TTG TAT AGA GGA CCA TTG GAT TTA ACA ATT ATA ATC ACA GGA
                                    650                                         660
 A   T   D   V   D   G   M   A   W   F   T   P   V   G   L   A   V   D   T   P
GCC ACT GAT GTG GAT GGT ATG GCC TGG TTT ACT CCA GTG GGC CTT GCT GTC GAC ACC CCT
                                    670                                         680
 W   V   E   K   E   S   A   L   S   I   D   Y   K   T   A   L   G   A   V   R
TGG GTG GAA AAG GAG TCA GCT TTG TCT ATT GAT TAT AAA ACT GCC CTT GGA GCT GTT AGA
                                    690                                         700
 F   N   T   R   R   T   G   N   I   Q   I   R   L   P   W   Y   S   Y   L   Y
TTT AAT ACA AGA AGA ACA GGA AAC ATT CAA ATT AGA TTG CCG TGG TAT TCT TAT TTG TAT
                                    710                                         720
 A   V   S   G   A   L   D   G   L   G   D   K   T   D   S   T   F   G   L   V
GCC GTG TCT GGA GCA CTG GAT GGC TTG GGG GAT AAG ACA GAT TCT ACA TTT GGA TTG GTT
                                    730                                         740
 S   I   Q   I   A   N   Y   N   H   S   D   E   Y   L   S   F   S   C   Y   L
TCT ATT CAG ATT GCA AAT TAC AAT CAT TCT GAT GAA TAT TTG TCC TTC AGT TGT TAT TTG
                                    750                                         760
 S   V   T   E   Q   S   E   F   Y   F   P   R   A   P   L   N   S   N   A   M
TCT GTC ACA GAG CAA TCA GAG TTC TAT TTT CCT AGA GCT CCA TTA AAT TCA AAT GCT ATG
                                    770                                         780
```

Page 3

FIGURE 6 (Continued)

```
  L   S   T   E   S   M   M   S   R   I   A   A   G   D   L   E   S   S   V   D
TTG TCC ACT GAA TCC ATG ATG AGT AGA ATT GCA GCT GGA GAC TTG GAG TCA TCA GTG GAT
                                790                                         800
  D   P   R   S   E   E   D   R   R   F   E   S   H   I   E   C   R   K   P   Y
GAT CCC AGA TCA GAG GAG GAT AGA AGA TTT GAG AGT CAT ATA GAA TGT AGG AAA CCA TAC
                                810                                         820
  K   E   L   R   L   E   V   G   K   Q   R   L   K   Y   A   Q   E   E   L   S
AAA GAA TTG AGA CTG GAG GTT GGG AAA CAA AGA CTC AAA TAT GCT CAG GAA GAG TTA TCA
                                830                                         840
  N   E   V   L   P   P   P   R   K   M   K   G   L   F   S   Q   A   K   I   S
AAT GAA GTG CTT CCA CCT CCT AGG AAA ATG AAA GGC CTA TTT TCA CAA GCT AAA ATT TCT
                                850                                         860
  L   F   Y   T   E   E   H   E   I   M   K   F   S   W   R   G   V   T   A   D
CTT TTT TAT ACT GAG GAG CAT GAA ATA ATG AAG TTT TCT TGG AGA GGA GTG ACT GCT GAT
                                870                                         880
  T   R   A   L   R   R   F   G   F   S   L   A   A   G   R   S   V   W   T   L
ACT AGG GCT TTG AGA AGA TTT GGA TTC TCT CTG GCT GCT GGT AGA AGT GTG TGG ACT CTT
                                890                                         900
  E   M   D   A   G   V   L   T   G   G   L   I   R   L   N   D   E   K   W   T
GAA ATG GAT GCT GGA GTT CTT ACT GGA GGA TTG ATC AGA TTG AAT GAT GAG AAA TGG ACA
                                910                                         920
  E   M   K   D   D   K   I   V   S   L   I   E   K   F   T   S   N   K   Y   W
GAA ATG AAG GAT GAT AAG ATT GTT TCA TTA ATT GAA AAG TTC ACA AGC AAT AAA TAT TGG
                                930                                         940
  S   K   V   N   F   P   H   A   M   L   D   L   E   E   I   A   A   N   S   K
TCT AAA GTG AAT TTT CCG CAT GCA ATG TTG GAT CTT GAA GAA ATT GCT GCC AAT TCG AAG
                                950                                         960
  D   F   P   N   M   S   E   T   D   L   C   F   L   L   H   W   L   N   P   K
GAT TTT CCA AAT ATG TCT GAG ACA GAT TTG TGT TTC CTG TTA CAT TGG CTA AAT CCA AAG
                                970                                         980
  K   I   N   L   A   D   R   M   L   G   L   S   G   V   Q   E   I   K   E   Q
AAA ATC AAT TTA GCA GAT AGA ATG CTT GGA TTG TCT GGA GTG CAG GAA ATT AAG GAA CAG
```

FIGURE 7

```
  1                                          10                                         20
  M   D   I   E   E   E   Q   M   I   Q   S   V   D   R   T   A   V   T   G   A
ATG GAT ATT GAG GAA GAG CAA ATG ATT CAG TCC GTT GAT AGG ACT GCA GTG ACT GGA GCT 30                                         40
  S   Y   F   T   S   V   D   Q   S   S   V   H   T   A   E   V   G   S   H   Q
TCT TAC TTC ACT TCT GTG GAC CAA TCT TCA GTT CAT ACT GCT GAG GTT GGC TCA CAT CAA 50                                         60
  I   E   P   L   K   T   S   V   D   K   P   G   S   K   K   T   Q   G   E   K
ATT GAA CCT TTG AAA ACC TCT GTT GAT AAA CCT GGT TCT AAG AAA ACT CAG GGG GAA AAG 70                                         80
  F   F   L   I   H   S   A   D   W   L   T   T   H   A   L   F   H   E   V   A
TTT TTC CTG ATT CAT TCT GCT GAT TGG CTC ACT ACA CAT GCT CTC TTT CAT GAA GTT GCA 90                                        100
  K   L   D   V   V   K   L   L   Y   N   E   Q   F   A   V   Q   G   L   L   R
AAA TTG GAT GTG GTG AAA CTA CTG TAT AAT GAG CAG TTT GCC GTC CAA GGT TTG TTG AGA 110                                        120
  Y   H   T   Y   A   R   F   G   I   E   I   Q   V   Q   I   N   P   T   P   F
TAC CAT ACA TAT GCA AGA TTT GGC ATT GAG ATT CAA GTT CAG ATA AAT CCC ACA CCC TTT 130                                        140
  Q   Q   G   G   L   I   C   A   M   V   P   G   D   Q   S   Y   G   S   I   A
CAG CAA GGA GGA CTA ATT TGT GCC ATG GTT CCT GGT GAC CAA AGT TAT GGT TCA ATA GCA 150                                        160
  S   L   T   V   Y   P   H   G   L   L   N   C   N   I   N   N   V   V   R   I
TCC TTG ACT GTT TAT CCT CAT GGT CTG TTA AAT TGC AAT ATC AAC AAT GTA GTT AGA ATA 170                                        180
  K   V   P   F   I   Y   T   R   G   A   Y   H   F   K   D   P   Q   Y   P   V
AAG GTT CCA TTT ATT TAT ACT AGA GGT GCT TAT CAT TTT AAA GAT CCA CAG TAC CCA GTT 190                                        200
  W   E   L   T   I   R   V   W   S   E   L   N   I   G   T   G   T   S   A   Y
TGG GAA TTG ACA ATC AGA GTT TGG TCA GAG TTG AAT ATT GGA ACA GGA ACT TCA GCT TAC 210                                        220
  T   S   L   N   V   L   A   R   F   T   D   L   E   L   H   G   L   T   P   L
ACT TCA CTC AAT GTT TTA GCT AGG TTT ACA GAT TTG GAG TTG CAT GGA TTA ACT CCT CTT

223
  S   T   Q
TCT ACA CAG
```

FIGURE 8

```
  1                                         10                                              20
  M   A   M   M   R   N   E   F   R   V   S   T   T   E   N   V   V   N   L   S
 ATG GCT ATG ATG AGA AAT GAA TTT AGG GTC AGT ACT ACT GAA AAT GTT GTA AAT TTG TCA 30                                              40
  N   Y   E   D   A   R   A   K   M   S   F   A   L   D   Q   E   D   W   K   S
 AAT TAT GAA GAT GCA AGG GCA AAA ATG TCT TTT GCT TTG GAT CAG GAA GAT TGG AAG TCT 50                                              60
  D   P   S   Q   G   G   G   I   K   I   T   H   F   T   T   W   T   S   I   P
 GAT CCT TCC CAA GGT GGT GGA ATT AAA ATT ACT CAT TTT ACT ACC TGG ACA TCC ATT CCA 70                                              80
  T   L   A   A   Q   F   P   F   N   A   S   D   S   V   G   Q   Q   I   K   V
 ACC TTA GCT GCT CAG TTT CCA TTT AAT GCT TCA GAT TCA GTT GGA CAA CAA ATT AAA GTT 90                                             100
  I   P   V   D   P   Y   F   F   Q   M   T   N   T   N   P   D   Q   K   C   I
 ATT CCA GTG GAC CCA TAC TTT TTC CAA ATG ACA AAC ACT AAT CCT GAT CAA AAA TGT ATA 110                                             120
  T   A   L   A   S   I   C   Q   M   F   C   F   W   R   G   D   L   V   F   D
 ACT GCC TTG GCC TCT ATT TGT CAG ATG TTC TGC TTT TGG AGG GGA GAT CTT GTT TTT GAT 130                                             140
  F   Q   V   F   P   T   K   Y   H   S   G   R   L   L   F   C   F   V   P   G
 TTT CAG GTT TTT CCA ACC AAA TAT CAT TCA GGT AGA CTG TTG TTT TGT TTT GTT CCT GGG 150                                             160
  N   E   L   I   D   V   T   G   I   T   L   K   Q   A   T   T   A   P   C   A
 AAT GAG TTA ATA GAT GTT ACT GGA ATT ACA TTA AAA CAG GCA ACT ACT GCT CCT TGT GCA 170                                             180
  V   M   D   I   T   G   V   Q   S   T   L   R   F   R   V   P   W   I   S   D
 GTG ATG GAC ATT ACA GGA GTG CAG TCA ACC TTG AGA TTT CGT GTT CCT TGG ATT TCT GAT 190                                             200
  T   P   Y   R   V   N   R   Y   T   K   S   A   H   Q   K   G   E   Y   T   A
 ACA CCT TAT CGA GTG AAT AGG TAC ACG AAG TCA GCA CAT CAA AAA GGT GAG TAC ACT GCC 210                                             220
  I   G   K   L   I   V   Y   C   Y   N   R   L   T   S   P   S   N   V   A   S
 ATT GGG AAG CTT ATT GTG TAT TGT TAT AAC AGA CTG ACT TCT CCT TCT AAT GTT GCC TCT 230                                             240
  H   V   R   V   N   V   Y   L   S   A   I   N   L   E   C   F   A   P   L   Y
 CAT GTT AGA GTT AAT GTT TAT CTT TCA GCA ATT AAT TTG GAA TGT TTT GCT CCT CTT TAC

H   A   M   D   V   T   T   Q
 CAT GCT ATG GAT GTT ACT ACA CAG
```

FIGURE 9

```
  1                                      10                                        20
  M   A   V   G   D   D   S   G   G   F   S   T   T   V   S   T   E   Q   N   V
ATG GCT GTT GGA GAT GAT TCA GGA GGT TTC TCA ACA ACA GTT TCT ACA GAG CAG AAT GTT 30                                        40
  P   D   P   Q   V   G   I   T   T   M   R   D   S   K   G   K   A   N   R   G
CCT GAT CCC CAA GTT GGG ATA ACA ACC ATG AGG GAT TCA AAA GGA AAA GCC AAT AGG GGA 50                                        60
  K   M   D   V   S   G   V   Q   A   P   V   G   A   I   T   T   I   E   D   P
AAG ATG GAT GTT TCA GGA GTG CAA GCA CCT GTG GGA GCT ATC ACA ACA ATT GAA GAT CCA 70                                        80
  V   L   A   K   K   V   P   E   T   F   P   E   L   K   P   G   E   S   R   H
GTT TTA GCA AAG AAA GTA CCT GAG ACA TTT CCT GAA TTG AAG CCT GGA GAG TCC AGA CAT 90                                       100
  T   S   D   H   M   S   I   Y   K   F   M   G   R   S   H   F   L   C   T   F
ACA TCA GAT CAC ATG TCT ATT TAT AAA TTC ATG GGA AGG TCT CAT TTT TTG TGC ACT TTT 110                                       120
  T   F   N   S   N   N   K   E   Y   T   F   P   I   T   L   S   S   T   S   N
ACT TTC AAT TCA AAT AAT AAA GAG TAC ACA TTT CCA ATA ACC CTG TCT TCG ACT TCT AAT 130                                       140
  P   P   H   G   L   P   S   T   L   R   W   F   F   N   L   F   Q   L   Y   R
CCT CCT CAT GGT TTA CCA TCA ACA TTA AGG TGG TTC TTC AAT TTG TTT CAG TTG TAT AGA 150                                       160
  G   P   L   D   L   T   I   I   I   T   G   A   T   D   V   D   G   M   A   W
GGA CCA TTG GAT TTA ACA ATT ATA ATC ACA GGA GCC ACT GAT GTG GAT GGT ATG GCC TGG 170                                       180
  F   T   P   V   G   L   A   V   D   T   P   W   V   E   K   E   S   A   L   S
TTT ACT CCA GTG GGC CTT GCT GTC GAC ACC CCT TGG GTG GAA AAG GAG TCA GCT TTG TCT 190                                       200
  I   D   Y   K   T   A   L   G   A   V   R   F   N   T   R   R   T   G   N   I
ATT GAT TAT AAA ACT GCC CTT GGA GCT GTT AGA TTT AAT ACA AGA AGA ACA GGA AAC ATC 210                                       220
  Q   I   R   L   P   W   Y   S   Y   L   Y   A   V   S   G   A   L   D   G   L
CAA ATT AGA TTG CCG TGG TAT TCT TAT TTG TAT GCC GTG TCT GGA GCA CTG GAT GGC TTG 230                                       240
  G   G   K   T   D   S   T   F   G   L   V   S   I   Q   I   A   N   Y   N   H
GGG GGT AAG ACA GAT TCT ACA TTT GGA TTG GTT TCT ATT CAG ATT GCA AAT TAC AAT CAT 250                                       260
  S   D   E   Y   L   S   F   S   C   Y   L   S   V   T   E   Q   S   E   F   Y
TCT GAT GAA TAT TTG TCC TTC AGT TGT TAT TTG TCT GTC ACA GAG CAA TCA GAG TTC TAT
```

FIGURE 9 (Continued)

```
                                    270                                         280
  F    P    R    A    P    L    N    S    N    A    M    L    S    T    E    S    M    M    S    R
 TTT  CCT  AGA  GCT  CCA  TTA  AAT  TCA  AAT  GCT  ATG  TTG  TCC  ACT  GAA  TCC  ATG  ATG  AGT  AGA 290                                         300
  I    A    A    G    D    L    E    S    S    V    D    D    P    R    S    E    E    D    R    R
 ATT  GCA  GCT  GGA  GAC  TTG  GAG  TCA  TCA  GTG  GAT  GAT  CCC  AGA  TCA  GAG  GAG  GAT  AGA  AGA

F    E
 TTT  GAG
```

Page 2

FIGURE 10

```
  1                                    10                                   20
  M   A   T   K   A   V   C   V   L   K   G   D   G   P   V   Q   G   I   I   N
ATG GCT ACA AAG GCT GTT TGT GTT TTG AAG GGT GAC GGC CCA GTT CAA GGT ATT ATT AAC 30                                   40
  F   E   Q   K   E   S   N   G   P   V   K   V   W   G   S   I   K   G   L   T
TTC GAG CAG AAG GAA AGT AAT GGA CCA GTG AAG GTG TGG GGA AGC ATT AAA GGA CTG ACT 50                                   60
  E   G   L   H   G   F   H   V   H   E   F   G   D   N   T   A   G   C   T   S
GAA GGC CTG CAT GGA TTC CAT GTT CAT GAG TTT GGA GAT AAT ACA GCA GGC TGT ACC AGT 70                                   80
  A   G   P   H   F   N   P   L   S   R   K   H   G   G   P   K   D   E   E   R
GCA GGT CCT CAC TTT AAT CCT CTA TCC AGA AAA CAC GGT GGG CCA AAG GAT GAA GAG AGG 90                                  100
  H   V   G   D   L   G   N   V   T   A   D   K   D   G   V   A   D   V   S   I
CAT GTT GGA GAC TTG GGC AAT GTG ACT GCT GAC AAA GAT GGT GTG GCC GAT GTG TCT ATT 110                                  120
  E   D   S   V   I   S   L   S   G   D   H   C   I   I   G   R   T   L   V   V
GAA GAT TCT GTG ATC TCA CTC TCA GGA GAC CAT TGC ATC ATT GGC CGC ACA CTG GTG GTC 130                                  140
  H   E   K   A   D   D   L   G   K   G   G   N   E   E   S   T   K   T   G   N
CAT GAA AAA GCA GAT GAC TTG GGC AAA GGT GGA AAT GAA GAA AGT ACA AAG ACA GGA AAC 150                                  160
  A   G   S   R   L   A   C   G   V   I   G   I   A   Q   N   L   G   I   Q   I
GCT GGA AGT CGT TTG GCT TGT GGT GTA ATT GGG ATC GCC CAG AAT TTG GGA ATT CAG ATC 170                                  180
  S   R   A   S   H   I   E   C   R   K   P   Y   K   E   L   R   L   E   V   G
TCT CGA GCT AGT CAT ATA GAA TGT AGG AAA CCA TAC AAA GAA TTG AGA CTG GAG GTT GGG 190                                  200
  K   Q   R   L   K   Y   A   Q   E   E   L   S   N   E   V   L   P   P   P   R
AAA CAA AGA CTC AAA TAT GCT CAG GAA GAG TTA TCA AAT GAA GTG CTT CCA CCT CCT AGG 210                                  220
  K   M   K   G   L   F   S   Q   A   K   I   S   L   F   Y   T   E   E   H   E
AAA ATG AAG GGG TTA TTT TCA CAA GCT AAA ATT TCT CTT TTT TAT ACT GAG GAG CAT GAA 230                                  240
  I   M   K   F   S   W   R   G   V   T   A   D   T   R   A   L   R   R   F   G
ATA ATG AAG TTT TCT TGG AGA GGA GTG ACT GCT GAT ACT AGG GCT TTG AGA AGA TTT GGA 250                                  260
  F   S   L   A   A   G   R   S   V   W   T   L   E   M   D   A   G   V   L   T
TTC TCT CTG GCT GCT GGT AGA AGT GTG TGG ACT CTT GAA ATG GAT GCT GGA GTT CTT ACT
```

FIGURE 10 (Continued)

```
                                270                                         280
    G   G   L   I   R   L   N   D   E   K   W   T   E   M   K   D   D   K   I   V
   GGA GGA TTG ATC AGA TTG AAT GAT GAG AAA TGG ACA GAA ATG AAG GAT GAT AAG ATT GTT 290                                         300
    S   L   I   E   K   F   T   S   N   K   Y   W   S   K   V   N   F   P   H   A
   TCA TTA ATT GAA AAG TTC ACA AGC AAT AAA TAT TGG TCT AAA GTG AAT TTT CCG CAT GCA 310                                         320
    M   L   D   L   E   E   I   A   A   N   S   K   D   F   P   N   M   S   E   T
   ATG TTG GAT CTT GAA GAA ATT GCT GCC AAT TCG AAG GAT TTT CCA AAT ATG TCT GAG ACA 330                                         340
    D   L   C   F   L   L   H   W   L   N   P   K   K   I   N   L   A   D   R   M
   GAT TTG TGT TTC CTG TTA CAT TGG CTA AAT CCA AAG AAA ATC AAT TTA GCA GAT AGA ATG

350
    L   G   L   S   G   V   Q   E   I   K   E   Q
   CTT GGA TTG TCT GGA GTG CAG GAA ATT AAG GAA CAG
```

FIGURE 11

```
  1                                        10                                        20
  M   A   T   K   A   V   C   V   L   K   G   D   G   P   V   Q   G   I   I   N
ATG GCT ACA AAG GCT GTT TGT GTT TTG AAG GGT GAC GGC CCA GTT CAA GGT ATT ATT AAC 30                                        40
  F   E   Q   K   E   S   N   G   P   V   K   V   W   G   S   I   K   G   L   T
TTC GAG CAG AAG GAA AGT AAT GGA CCA GTG AAG GTG TGG GGA AGC ATT AAA GGA CTG ACT 50                                        60
  E   G   L   H   G   F   H   V   H   E   F   G   D   N   T   A   G   C   T   S
GAA GGC CTG CAT GGA TTC CAT GTT CAT GAG TTT GGA GAT AAT ACA GCA GGC TGT ACC AGT 70                                        80
  A   G   P   H   F   N   P   L   S   R   K   H   G   G   P   K   D   E   E   R
GCA GGT CCT CAC TTT AAT CCT CTA TCC AGA AAA CAC GGT GGG CCA AAG GAT GAA GAG AGG 90                                       100
  H   V   G   D   L   G   N   V   T   A   D   K   D   G   V   A   D   V   S   I
CAT GTT GGA GAC TTG GGC AAT GTG ACT GCT GAC AAA GAT GGT GTG GCC GAT GTG TCT ATT 110                                       120
  E   D   S   V   I   S   L   S   G   D   H   C   I   I   G   R   T   L   V   V
GAA GAT TCT GTG ATC TCA CTC TCA GGA GAC CAT TGC ATC ATT GGC CGC ACA CTG GTG GTC 130                                       140
  H   E   K   A   D   D   L   G   K   G   G   N   E   E   S   T   K   T   G   N
CAT GAA AAA GCA GAT GAC TTG GGC AAA GGT GGA AAT GAA GAA AGT ACA AAG ACA GGA AAC 150                                       160
  A   G   S   R   L   A   C   G   V   I   G   I   A   Q   N   L   G   I   Q   I
GCT GGA AGT CGT TTG GCT TGT GGT GTA ATT GGG ATC GCC CAG AAT TTG GGA ATT CAG ATC 170                                       180
  S   R   G   I   S   D   D   D   N   D   S   A   M   A   E   F   F   Q   S   F
TCT CGA GGA ATT TCA GAT GAT GAC AAT GAT AGT GCA ATG GCT GAG TTT TTC CAG TCT TTT 190                                       200
  P   S   G   E   P   S   N   S   K   L   S   S   F   F   Q   S   V   T   N   H
CCA TCT GGT GAA CCA TCA AAT TCC AAG TTA TCT AGT TTT TTC CAA TCT GTC ACT AAT CAC 210                                       220
  K   W   V   A   V   G   A   A   V   G   I   L   G   V   L   V   G   G   W   F
AAG TGG GTT GCT GTG GGA GCT GCA GTT GGC ATT CTT GGA GTG CTT GTG GGA GGA TGG TTT

230
  V   Y   K   H   F   S   R   K   E   E   E   P   I   P   A   E
GTG TAT AAG CAT TTT TCC CGC AAA GAG GAA GAA CCA ATT CCA GCT GAA
```

FIGURE 12

```
     1                                      10
     M   A   T   K   A   V   C   V   L   K   G   D   G   P   V   Q   G   I   I
CC  ATG GCT ACA AAG GCT GTT TGT GTT TTG AAG GGT GAC GGC CCA GTT CAA GGT ATT ATT 20                                     30
    N   F   E   Q   K   E   S   N   G   P   V   K   V   W   G   S   I   K   G   L
   AAC TTC GAG CAG AAG GAA AGT AAT GGA CCA GTG AAG GTG TGG GGA AGC ATT AAA GGA CTG 40                                     50
    T   E   G   L   H   G   F   H   V   H   E   F   G   D   N   T   A   G   C   T
   ACT GAA GGC CTG CAT GGA TTC CAT GTT CAT GAG TTT GGA GAT AAT ACA GCA GGC TGT ACC 60                                     70
    S   A   G   P   H   F   N   P   L   S   R   K   H   G   P   K   D   E   E
   AGT GCA GGT CCT CAC TTT AAT CCT CTA TCC AGA AAA CAC GGT GGG CCA AAG GAT GAA GAG 80                                     90
    R   H   V   G   D   L   G   N   V   T   A   D   K   D   G   V   A   D   V   S
   AGG CAT GTT GGA GAC TTG GGC AAT GTG ACT GCT GAC AAA GAT GGT GTG GCC GAT GTG TCT 100                                    110
    I   E   D   S   V   I   S   L   S   G   D   H   C   I   I   G   R   T   L   V
   ATT GAA GAT TCT GTG ATC TCA CTC TCA GGA GAC CAT TGC ATC ATT GGC CGC ACA CTG GTG 120                                    130
    V   H   E   K   A   D   D   L   G   K   G   G   N   E   E   S   T   K   T   G
   GTC CAT GAA AAA GCA GAT GAC TTG GGC AAA GGT GGA AAT GAA GAA AGT ACA AAG ACA GGA 140                                    150
    N   A   G   S   R   L   A   C   G   V   I   G   I   A   Q   N   L   G   I   Q
   AAC GCT GGA AGT CGT TTG GCT TGT GGT GTA ATT GGG ATC GCC CAG AAT TTG GGA ATT CAG 160                                    170
    I   S   R   A   S   T   L   E   I   A   G   L   V   R   K   N   L   V   Q   F
   ATC TCT CGA GCA TCA ACT CTA GAA ATA GCA GGA TTA GTT AGG AAA AAT CTG GTT CAG TTT 180                                    190
    G   V   G   E   K   N   G   C   V   R   W   V   M   N   A   L   G   V   K   D
   GGA GTT GGT GAG AAA AAT GGA TGT GTG AGA TGG GTC ATG AAT GCC TTA GGA GTG AAG GAT 200                                    210
    D   W   L   L   V   P   S   H   A   Y   K   F   E   K   D   Y   E   M   M   E
   GAT TGG TTG TTA GTA CCT TCT CAT GCT TAT AAA TTT GAA AAG GAT TAT GAA ATG ATG GAG 220                                    230
    F   Y   F   N   R   G   G   T   Y   Y   S   I   S   A   G   N   V   V   I   Q
   TTT TAC TTC AAT AGA GGT GGA ACT TAC TAT TCA ATT TCA GCT GGT AAT GTT GTT ATT CAA 240                                    250
    S   L   D   V   G   F   Q   D   V   V   L   M   K   V   P   T   I   P   K   F
```

Page 1

FIGURE 12 (Continued)

```
TCT TTA GAT GTG GGA TTT CAA GAT GTT GTT TTA ATG AAG GTT CCT ACA ATT CCC AAG TTT 260                                         270
 R   D   I   T   Q   H   F   I   K   K   G   D   V   P   R   A   L   N   R   L
AGA GAT ATT ACT CAA CAC TTT ATT AAG AAA GGA GAT GTG CCT AGA GCC TTA AAT CGC TTG 280                                         290
 A   T   L   V   T   T   V   N   G   T   P   M   L   I   S   E   G   P   L   K
GCA ACA TTA GTG ACA ACC GTT AAT GGA ACT CCT ATG TTA ATT TCT GAG GGA CCA TTA AAG 300                                         310
 M   E   E   K   A   T   Y   V   H   K   K   N   D   G   T   T   V   D   L   T
ATG GAA GAA AAA GCC ACT TAT GTT CAT AAG AAG AAT GAT GGT ACT ACA GTT GAT TTG ACT 320                                         330
 V   D   Q   A   W   R   G   K   G   E   G   L   P   G   M   C   G   G   A   L
GTA GAT CAG GCA TGG AGA GGA AAA GGT GAA GGT CTT CCT GGA ATG TGT GGT GGG GCC CTA 340                                         350
 V   S   S   N   Q   S   I   Q   N   A   I   L   G   I   H   V   A   G   G   N
GTG TCA TCA AAT CAG TCC ATA CAG AAT GCA ATT TTG GGT ATT CAT GTT GCT GGA GGA AAT 360                                         370
 S   I   L   V   A   K   L   V   T   Q   E   M   F   Q   N   I   D   K   K   I
TCA ATT CTT GTG GCA AAG CTG GTT ACT CAA GAA ATG TTT CAA AAC ATT GAT AAG AAA ATT

380
 E   S   Q
GAA AGT CAG
```

Page 2

FIGURE 13

```
  1                                           10                                          20
  M   A   T   K   A   V   C   V   L   K   G   D   G   P   V   Q   G   I   I   N
 ATG GCT ACA AAG GCT GTT TGT GTT TTG AAG GGT GAC GGC CCA GTT CAA GGT ATT ATT AAC 30                                          40
  F   E   Q   K   E   S   N   G   P   V   K   V   W   G   S   I   K   G   L   T
 TTC GAG CAG AAG GAA AGT AAT GGA CCA GTG AAG GTG TGG GGA AGC ATT AAA GGA CTG ACT 50                                          60
  E   G   L   H   G   F   H   V   H   E   F   G   D   N   T   A   G   C   T   S
 GAA GGC CTG CAT GGA TTC CAT GTT CAT GAG TTT GGA GAT AAT ACA GCA GGC TGT ACC AGT 70                                          80
  A   G   P   H   F   N   P   L   S   R   K   H   G   G   P   K   D   E   E   R
 GCA GGT CCT CAC TTT AAT CCT CTA TCC AGA AAA CAC GGT GGG CCA AAG GAT GAA GAG AGG 90                                         100
  H   V   G   D   L   G   N   V   T   A   D   K   D   G   V   A   D   V   S   I
 CAT GTT GGA GAC TTG GGC AAT GTG ACT GCT GAC AAA GAT GGT GTG GCC GAT GTG TCT ATT 110                                         120
  E   D   S   V   I   S   L   S   G   D   H   C   I   I   G   R   T   L   V   V
 GAA GAT TCT GTG ATC TCA CTC TCA GGA GAC CAT TGC ATC ATT GGC CGC ACA CTG GTG GTC 130                                         140
  H   E   K   A   D   D   L   G   K   G   G   N   E   E   S   T   K   T   G   N
 CAT GAA AAA GCA GAT GAC TTG GGC AAA GGT GGA AAT GAA GAA AGT ACA AAG ACA GGA AAC 150                                         160
  A   G   S   R   L   A   C   G   V   I   G   I   A   Q   N   L   G   I   Q   I
 GCT GGA AGT CGT TTG GCT TGT GGT GTA ATT GGG ATC GCC CAG AAT TTG GGA ATT CAG ATC 170                                         180
  S   R   A   R   I   M   K   V   E   F   T   Q   C   S   M   N   V   V   S   K
 TCT CGA GCA AGA ATA ATG AAA GTG GAA TTT ACT CAA TGT TCA ATG AAT GTA GTC TCC AAA 190                                         200
  T   L   F   R   K   S   P   I   H   H   H   I   D   K   T   M   I   N   F   P
 ACG CTT TTT AGA AAG AGT CCC ATT CAT CAC CAC ATT GAT AAA ACC ATG ATT AAT TTT CCT 210                                         220
  A   A   M   P   F   S   K   A   E   I   D   P   M   A   M   T   L   S   K   Y
 GCA GCT ATG CCT TTC TCT AAA GCT GAA ATT GAT CCA ATG GCT ATG ACG TTG TCC AAA TAT 230                                         240
  S   L   P   I   V   E   E   P   E   D   Y   K   E   A   S   V   F   Y   Q   N
 TCA TTA CCT ATT GTG GAG GAA CCA GAG GAT TAC AAG GAA GCT TCA GTT TTT TAT CAA AAC 250                                         260
```

Page 1

FIGURE 13 (Continued)

```
  K   I   V   G   K   T   Q   L   V   D   D   F   L   D   L   D   M   A   I   T
 AAA ATA GTA GGC AAG ACT CAG CTA GTT GAT GAC TTT TTA GAT CTT GAT ATG GCT ATT ACA
                                 270                                         280
  G   A   P   G   I   D   A   I   N   M   D   S   S   P   G   F   P   Y   V   Q
 GGG GCT CCA GGC ATT GAT GCT ATC AAT ATG GAT TCA TCT CCT GGG TTT CCT TAT GTT CAA
                                 290                                         300
  E   K   L   T   K   R   D   L   I   W   L   D   E   N   G   L   L   L   G   V
 GAA AAA TTG ACC AAA AGA GAT TTA ATT TGG TTG GAT GAA AAT GGT TTG CTG TTA GGA GTT
                                 310                                         320
  H   P   R   L   A   Q   R   I   L   F   N   T   V   M   M   E   N   C   S   D
 CAC CCA AGA TTG GCC CAG AGA ATT TTA TTT AAT ACT GTC ATG ATG GAA AAT TGT TCT GAC
                                 330                                         340
  L   D   V   V   F   T   T   C   P   K   D   E   L   R   P   L   E   K   V   L
 TTA GAT GTT GTT TTT ACA ACT TGT CCA AAA GAT GAA TTG AGA CCA TTA GAG AAA GTT TTG
                                 350                                         360
  E   S   K   T   R   A   I   D   A   C   P   L   D   Y   T   I   L   C   R   M
 GAA TCA AAA ACA AGA GCC ATT GAT GCT TGT CCT TTG GAT TAT ACA ATT CTA TGT CGA ATG
                                 370                                         380
  Y   W   G   P   A   I   S   Y   F   H   L   N   P   G   F   H   T   G   V   A
 TAT TGG GGT CCA GCT ATC AGT TAT TTC CAT TTG AAT CCA GGG TTT CAC ACA GGT GTT GCT
                                 390                                         400
  I   G   I   D   P   D   K   Q   W   D   E   L   F   K   T   M   I   R   F   G
 ATT GGC ATA GAT CCT GAT AAA CAG TGG GAT GAA TTA TTT AAA ACA ATG ATA AGA TTT GGA
                                 410                                         420
  D   V   G   L   D   L   D   F   S   A   F   D   A   S   L   S   P   F   M   I
 GAT GTT GGT CTT GAT TTA GAT TTC TCT GCT TTT GAT GCC AGT CTT AGT CCA TTT ATG ATT
                                 430                                         440
  R   E   A   G   R   I   M   S   E   L   S   G   T   P   S   H   F   G   T   A
 AGG GAA GCA GGT AGA ATC ATG AGT GAA TTA TCT GGA ACA CCA TCT CAT TTT GGA ACA GCT
                                 450                                         460
  L   I   N   T   I   I   Y   S   K   H   L   L   Y   N   C   C   Y   H   V   C
 CTT ATC AAT ACT ATC ATT TAT TCT AAA CAT CTG CTG TAC AAC TGT TGT TAT CAT GTT TGT
                                 470                                         480
  G   S   M   P   S   G   S   P   C   T   A   L   L   N   S   I   I   N   N   I
 GGT TCA ATG CCT TCT GGG TCT CCT TGC ACA GCT TTG TTG AAT TCA ATT ATT AAT AAT ATT
                                 490                                         500
  N   L   Y   Y   V   F   S   K   I   F   G   K   S   P   V   F   F   C   Q   A
```

Page 2

FIGURE 13 (Continued)

```
                                            510                                   520
                                  L   R   I   L   C   Y   G   D   D   V   L   I   V   F   S   R   D   V   Q   I
AAT CTG TAT TAT GTG TTT TCT AAA ATA TTT GGA AAG TCT CCA GTT TTC TTT TGT CAA GCT
TTG AGG ATC CTT TGT TAC GGA GAT GAT GTT TTG ATA GTT TTT TCC AGA GAT GTT CAA ATT 530                                   540
D   N   L   D   L   I   G   Q   K   I   V   D   E   F   K   K   L   G   M   T
GAC AAT CTT GAC TTG ATT GGA CAG AAA ATT GTA GAT GAG TTC AAA AAA CTT GGC ATG ACA 550                                   560
A   T   S   A   D   K   N   V   P   Q   L   K   P   V   S   E   L   T   F   L
GCC ACC TCA GCT GAT AAA AAT GTG CCT CAA CTG AAG CCA GTT TCA GAA TTG ACT TTT CTC 570                                   580
K   R   S   F   N   L   V   E   D   R   I   R   P   A   I   S   E   K   T   I
AAA AGA TCT TTC AAT TTG GTG GAG GAT AGA ATT AGA CCT GCA ATT TCA GAA AAG ACA ATT 590                                   600
W   S   L   M   A   W   Q   R   S   N   A   E   F   E   Q   N   L   E   N   A
TGG TCT TTG ATG GCT TGG CAG AGA AGT AAC GCT GAG TTT GAG CAG AAT TTA GAA AAT GCT 610                                   620
Q   W   F   A   F   M   H   G   Y   E   F   Y   Q   K   F   Y   Y   F   V   Q
CAG TGG TTT GCT TTT ATG CAT GGC TAT GAG TTC TAT CAG AAA TTT TAT TAT TTT GTT CAG 630                                   640
S   C   L   E   K   E   M   I   E   Y   R   L   K   S   Y   D   W   W   R   M
TCC TGT TTG GAG AAA GAG ATG ATA GAA TAT AGA CTT AAA TCT TAT GAT TGG TGG AGA ATG

650
R   F   Y   D   Q   C   F   I   C   D   L   S
AGA TTT TAT GAC CAG TGT TTC ATT TGT GAC CTT TCA
```

Page 3

HEPATITIS A VIRUS NUCLEOTIDE SEQUENCES, RECOMBINANT PROTEINS AND USES THEREOF

CROSS-REFERENCE TO RELATED APPLICATIONS

This application is related to provisional patent applications Ser. No. 60/328,933 filed Oct. 12, 2001, from which priority is claimed under 35 USC §119(e)(1) and which application is incorporated herein by reference in its entireties.

TECHNICAL FIELD

The present invention pertains generally to viral diagnostics. In particular, the invention relates to nucleic acid and antibody-based as says for accurately diagnosing hepatitis A virus infection.

BACKGROUND OF THE INVENTION

Hepatitis A is an enterically transmitted disease that causes fever, malaise, anorexia, nausea, abdominal discomfort and jaundice. The etiologic agent of hepatitis A, the hepatitis A virus, is a small, nonenveloped, spherical virus classified in the genus Hepatovirus of the Picornaviridae family. The HAV genome consists of a single-strand, linear, 7.5 kb RNA molecule encoding a polyprotein precursor that is processed to yield the structural proteins and enzymatic activities required for viral replication. HAV grows poorly in cell culture, is not cytopathic, and produces low yields of virus. Although HAV RNA extracted from virions is infectious in cell culture (Locarnini et al., J. Virol. 37:216–225, 1981 and Siegl et al., J. Gen. Virol. 57:331–341, 1981), direct manipulation of the viral genome becomes difficult because of its RNA composition.

HAV encodes four capsid proteins (A, B, C and D) which contain the major antigenic domains recognized by antibodies of infected individuals. In addition to the capsid proteins, antigenic domains have been reported in nonstructural proteins such as 2A and the viral encoded protease. Another important HAV antigenic domain has been described in the junction between the capsid precursor P1 and 2A.

HAV is normally acquired by fecal-oral route, by either person-to-person contact or ingestion of contaminated food or water. However, there is the potential for HAV transmission by pooled plasma products. The absence of a lipid envelope makes HAV very resistant to physicochemical inactivation, and the virus can withstand conventional heat treatment of blood products. Thus, HAV, as well as Parvovirus B19, have been transmitted through the administration of pooled plasma derivatives. The development of sensitive and specific diagnostic assays to identify HAV antigens and/or antibodies in infected individuals as well as nucleic acid-based tests to detect viremic samples to exclude them from transfusion represents an important public health challenge.

Therefore, there remains a need for the development of reliable diagnostic tests to detect hepatitis A virus in viremic samples, in order to prevent transmission of the virus through blood and plasma derivatives or by close personal contact.

SUMMARY OF THE INVENTION

The present invention is based on the development of a sensitive, reliable nucleic acid-based diagnostic test for the detection of hepatitis A virus (HAV) in biological samples from potentially infected individuals. The techniques described herein utilize extracted sample RNA as a template for amplification of HAV genomic sequence using transcription-mediated amplification (TMA), as well as in a 5' nuclease assay, such as the TaqMan™ technique. The methods allow for the detection of HAV in viremic samples. Accordingly, infected samples can be identified and excluded from transfusion, as well as from the preparation of blood derivatives.

In one aspect, the invention is directed to an isolated polynucleotide comprising (a) a nucleotide sequence comprising any one of the nucleotide sequences depicted in SEQ ID NOs: 1–39; (b) an isolated polynucleotide encoding a polypeptide comprising any one of SEQ ID NOs: 40–48; (c) a sequence complementary to any one of the sequences of (a) or (b); or (d) a fragment of any of the sequences in (a) or (b) wherein the fragment is at least 10 nucleotides.

In another embodiment, the invention is directed to an oligonucleotide primer consisting of a promoter region recognized by a DNA-dependent RNA polymerase operably linked to a HAV-specific complexing sequence of about 10 to about 75 nucleotides. In certain embodiments, the promoter region is the T7 promoter and said polymerase is T7 RNA polymerase. Additionally, the HAV-specific sequence may be from the HAV genome, such as a nucleotide sequence comprising any one of the nucleotide sequences depicted in SEQ ID NOs: 1–39.

In yet further embodiments, the invention is directed an oligonucleotide primer consisting of a T7 promoter operably linked to a HAV-specific complexing sequence of about 10 to about 75 nucleotides, wherein the HAV-specific complexing sequence is derived from any one of the polynucleotide sequences of SEQ ID NOs: 1–39.

In another embodiment, the invention is directed to an oligonucleotide probe comprising a HAV-specific hybridizing sequence of about 10 to about 50 nucleotides linked to an acridinium ester label. In certain embodiments, the HAV-specific hybridizing sequence is a polynucleotide sequence derived from any one of the polynucleotide sequences of SEQ ID NOs: 1–39.

In another embodiment, the invention is directed to a vaccine composition comprising an isolated immunogenic Hepatitis A virus (HAV) polypeptide, and a pharmaceutically acceptable excipient, wherein the HAV polypeptide is a polypeptide with at least 80% sequence identity to any one of the sequences of SEQ ID NOs: 40–48, or an immunogenic fragment thereof comprising at least 10 amino acids.

In yet an additional embodiment, the invention is directed to a diagnostic test kit comprising one or more oligonucleotide primers described herein, and instructions for conducting the diagnostic test. In certain embodiments, the test kit further comprises an oligonucleotide probe comprising a HAV hybridizing sequence of about 10 to about 50 nucleotides linked to an acridinium ester label.

In another embodiment, the invention is directed to an immunoassay for detecting antibodies that bind to a hepatitis A virus polypeptide comprising: providing an antigen comprising a sequence having at least 80% sequence identity to any one of the sequences of SEQ ID NOs: 40–48, or fragment thereof; incubating the antigen with a biological sample under conditions that allow for formation of an antibody-antigen complex; and detecting any antibody-antigen complexes comprised of said antigen. The antigen may be immobilized on a solid support, and may be at least 10 amino acids. In addition, the biological sample can be bodily fluid, tissue, or organ, such as human blood or a fraction thereof.

In yet another embodiment, the invention is directed to a method for detecting Hepatitis A virus (HAV) infection in a biological sample, the method comprising (a) isolating nucleic acid from a biological sample suspected of containing Hepatitis A virus (HAV) RNA, wherein said nucleic acid comprises a target sequence, (b) reacting the HAV nucleic acid with a detectably labeled probe sufficiently complementary to and capable of hybridizing with the target sequence, wherein the probe is derived from any one of SEQ ID NOs: 1–39, and further wherein said reacting is done under conditions that provide for the formation of a probe/target sequence complex, and (c) detecting the presence or absence of label as an indication of the presence or absence of the target sequence.

These and other aspects of the present invention will become evident upon reference to the following detailed description and attached drawings. In addition, various references are set forth herein which describe in more detail certain procedures or compositions, and are therefore incorporated by reference in their entirety.

BRIEF DESCRIPTION OF THE DRAWINGS

FIG. 1 illustrates the nucleotide sequence of the 243 base pair VP3/VP1 HAV fragment determined for thirteen Indonesian (IND) (SEQ ID NOs: 1–13) and fourteen Chilean (SCL) (SEQ ID NOs: 14–27) isolates.

FIG. 2 illustrates the nucleotide sequence (SEQ ID NO: 28) of a 2,950 bp KpnI/SphI insert encoding the HAV P1/2A precursor.

FIG. 3 illustrates the nucleotide sequence (SEQ ID NO: 29) of a 6,696 bp KpnI/SphI insert encoding the full length HAV open reading frame.

FIG. 4 illustrates the nucleotide sequence (SEQ ID NO: 30) of a 6,757 bp KpnI/SphI insert encoding the full length HAV open reading frame plus additional 3' untranslated sequences.

FIG. 5 illustrates the nucleotide (SEQ ID NO: 31) and corresponding amino acid sequence (SEQ ID NO: 40) of the recombinant protein of 94 kDa consisting of the capsid precursor P1 (methionine$^{1}$-glutamic acid$^{791}$) plus the 45 amino terminal residues of the nonstructural protein 2A (serine$^{792}$ through glutamine$^{836}$).

FIG. 6 illustrates the nucleotide (SEQ ID NO: 32) and corresponding amino acid sequence (SEQ ID NO: 41) of the recombinant protein of 115.5 kDa consisting of precursor P1 (Met$^{1}$-Glu$^{791}$) fused with the nonstructural protein 2A (Ser$^{792}$-Gln$^{980}$).

FIG. 7 illustrates the nucleotide (SEQ ID NO: 33) and corresponding amino acid sequence (SEQ ID NO: 42) of the recombinant protein of 25 kDa (Asp$^{24}$-Gln$^{245}$) representing HAV capsid protein 1B (VP2 gene product).

FIG. 8 illustrates the nucleotide (SEQ ID NO: 34) and corresponding amino acid sequence (SEQ ID NO: 43) of the recombinant protein of 28 kDa (Met$^{246}$-Gln$^{491}$) representing HAV capsid protein 1C (VP3 gene product).

FIG. 9 illustrates the nucleotide (SEQ ID NO: 35) and corresponding amino acid sequence (SEQ ID NO: 44) of the recombinant protein of 33.3 kDa (Val$^{492}$-Glu$^{791}$) representing HAV capsid protein 1D (VP1 gene, product).

FIG. 10 illustrates the nucleotide (SEQ ID NO: 36) and corresponding amino acid sequence (SEQ ID NO: 45) of the recombinant protein of 38.8 kDa consisting of human superoxide dismutase (153 aminoacids) fused with the HAV nonstructural protein 2A (Ser$^{792}$-Gln$^{980}$).

FIG. 11 illustrates the nucleotide (SEQ ID NO: 37) and corresponding amino acid sequence (SEQ ID NO: 46) of the recombinant protein of 24.9 kDa consisting of human superoxide dismutase (153 amino acids) fused with the HAV nonstructural protein 3A (Gly$^{1423}$ -Glu$^{1496}$).

FIG. 12 illustrates the nucleotide (SEQ ID NO: 38) and corresponding amino acid sequence (SEQ ID NO: 47) of the recombinant protein of 41 kDa consisting of human superoxide dismutase (153 amino acids) fused with the HAV nonstructural protein 3C (Protease: Ser$^{1520}$-Gln$^{1678}$).

FIG. 13 illustrates the nucleotide (SEQ ID NO: 39) and corresponding amino acid sequence (SEQ ID NO: 48) of the recombinant protein of human superoxide dismutase (153 amino acids) fused with the HAV nonstructural protein 3D (RNA dependent RNA polymerase: Arg$^{1739}$-Ser$^{2227}$).

DETAILED DESCRIPTION OF THE INVENTION

The practice of the present invention will employ, unless otherwise indicated, conventional methods of chemistry, biochemistry, recombinant DNA techniques and virology, within the skill of the art. Such techniques are explained fully in the literature. See, e.g., *Fundamental Virology,* 2nd Edition, vol. I & II (B. N. Fields and D. M. Knipe, eds.); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Oligonucleotide Synthesis* (N. Gait, ed., 1984); *A Practical Guide to Molecular Cloning* (1984).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

Alanine: Ala (A)
Asparagine: Asn (N)
Cysteine: Cys (C)
Glutamic acid: Glu (E)
Histidine: His (H)
Leucine: Leu (L)
Methionine: Met (M)
Proline: Pro (P)
Threonine: Thr (T)
Tyrosine: Tyr (Y)
Arginine: Arg (R)
Aspartic acid: Asp (D)
Glutamine: Gln (Q)
Glycine: Gly (G)
Isoleucine: Ile (I)
Lysine: Lys (K)
Phenylalanine: Phe (F)
Serine: Ser (S)
Tryptophan: Trp (W)
Valine: Val (V)

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

The terms "analog" and "mutein" refer to biologically active derivatives of the reference molecule, or fragments of such derivatives, that retain desired activity, such as immunoreactivity in diagnostic assays. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publication No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5–10 conservative or non-conservative amino acid substitutions, or even up to about 15–25 conservative or non-conservative amino acid substitutions, or any integer between 5–25, so long as the desired function of the molecule remains intact. One of skill in the art may readily determine regions of the molecule of interest that can tolerate change by reference to Hopp/Woods and Kyte-Doolittle plots, well known in the art.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

A polynucleotide "derived from" or "specific for" a designated sequence refers to a polynucleotide sequence which comprises a contiguous sequence of approximately at least about 6 nucleotides, preferably at least about 8 nucleotides, more preferably at least about 10–12 nucleotides, and even more preferably at least about 15–20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%–85%, preferably at least about 90%, and most preferably at least about 95%–98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter= none; strand=both; cutoff=60; expect=10; Matrix= BLOSUM62; Descriptions=50 sequences; sort by=HIGH SCORE; Databases=non-redundant, GenBank+EMBL+ DDBJ+PDB+GenBank CDS translations+Swiss protein+ Spupdate+PIR. Details of these programs can be found at the following internet address: http://www.ncbi.nlm.gov/cgi-bin/BLAST:

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Operably linked" refers to an arrangement of elements wherein the components so described are configured so as to perform their desired function. Thus, a given promoter operably linked to a nucleic acid sequence is capable of effecting the transcription, and in the case of a coding sequence, the expression of the coding sequence when the proper transcription factors, etc., are present. The promoter need not be contiguous with the nucleic acid sequence, so long as it functions to direct the transcription and/or expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the transcription and/or translation of a nucleotide sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a regulatory region capable of binding a polymerase and initiating transcription of a downstream (3' direction) nucleotide sequence operably linked thereto. For purposes of the present invention, a promoter sequence includes the minimum number of bases or elements necessary to initiate transcription of a sequence of interest at levels detectable above background. Within the promoter sequence is a transcription initiation site, as well as protein binding domains (consensus sequences) responsible for the binding of RNA or DNA polymerase. For example, promoter may be a nucleic acid sequence that is recognized by a DNA-dependent RNA polymerase ("transcriptase") as a signal to bind to the nucleic acid and begin the transcription of RNA at a specific site. For binding, such transcriptases generally require DNA which is double-stranded in the portion comprising the promoter sequence and its complement; the template portion (sequence to be transcribed) need not be double-stranded. Individual DNA-dependent RNA polymerases recognize a variety of different promoter sequences which can vary markedly in their efficiency in promoting transcription. When an RNA polymerase binds to a promoter sequence to initiate transcription, that promoter sequence is not part of the sequence transcribed. Thus, the RNA transcripts produced thereby will not include that sequence.

A control sequence "directs the transcription" of a nucleotide sequence when RNA or DNA polymerase will bind the promoter sequence and transcribe the adjacent sequence.

A "DNA-dependent DNA polymerase" is an enzyme that synthesizes a complementary DNA copy from a DNA template. Examples are DNA polymerase I from *E. coli* and bacteriophage T7 DNA polymerase. All known DNA-dependent DNA polymerases require a complementary primer to initiate synthesis. Under suitable conditions, a DNA-dependent DNA polymerase may synthesize a complementary DNA copy from an RNA template.

A "DNA-dependent RNA polymerase" or a "transcriptase" is an enzyme that synthesizes multiple RNA copies from a double-stranded or partially-double stranded DNA molecule having a (usually double-stranded) promoter sequence. The RNA molecules ("transcripts") are synthesized in the 5' to 3' direction beginning at a specific position just downstream of the promoter. Examples of transcriptases are the DNA-dependent RNA polymerase from *E. coli* and bacteriophages T7, T3, and SP6.

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with both RNA and DNA templates.

"RNAse H" is an enzyme that degrades the RNA portion of an RNA:DNA duplex. These enzymes may be endonucleases or exonucleases. Most reverse transcriptase enzymes normally contain an RNAse H activity in addition to their polymerase activity. However, other sources of the RNAse H are available without an associated polymerase activity. The degradation may result in separation of RNA from a RNA:DNA complex. Alternatively, the RNAse H may simply cut the RNA at various locations such that portions of the RNA melt off or permit enzymes to unwind portions of the RNA.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Ore., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

As used herein, the term "target nucleic acid region" or "target nucleic acid" denotes a nucleic acid molecule with a "target sequence" to be amplified. The target nucleic acid may be either single-stranded or double-stranded and may include other sequences besides the target sequence, which may not be amplified. The term "target sequence" refers to the particular nucleotide sequence of the target nucleic acid which is to be amplified. The target sequence may include a probe-hybridizing region contained within the target molecule with which a probe will form a stable hybrid under desired conditions. The "target sequence" may also include the complexing sequences to which the oligonucleotide primers complex and be extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands.

The term "primer" or "oligonucleotide primer" as used herein, refers to an oligonucleotide which acts to initiate synthesis of a complementary DNA strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer is first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

As used herein, the term "probe" or "oligonucleotide probe" refers to a structure comprised of a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs. When an "oligonucleotide probe" is to be used in a 5' nuclease assay, such as the TaqMan™ technique, the probe will contain at least one fluorescer and at least one quencher which is digested by the 5' endonuclease activity of a polymerase used in the reaction in order to detect any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers. When an oligonucleotide probe is used in the TMA technique, it will be suitably labeled, as described below.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

Stringent hybridization conditions will typically include salt concentrations of less than about 1 M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art. Less stringent, and/or more physiological, hybridization conditions are used where a labeled polynucleotide amplification product cycles on and off a substrate linked to a complementary probe polynucleotide during a real-time assay which is monitored during PCR amplification such as a molecular beacon assay. Such less stringent hybridization conditions can also comprise solution conditions effective for other aspects of the method, for example reverse transcription or PCR.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. Unless the context clearly indicates otherwise, the terms "affinity molecule" and "target analyte" are used herein to refer to first and second members of a binding pair, respectively.

The terms "specific-binding molecule" and "affinity molecule" are used interchangeably herein and refer to a molecule that will selectively bind, through chemical or physical means to a detectable substance present in a sample. By "selectively bind" is meant that the molecule binds preferentially to the target of interest or binds with greater affinity to the target than to other molecules. For example, a DNA molecule will bind to a substantially complementary sequence and not to unrelated sequences.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$. The highest rate of nucleic acid hybridization occurs approximately 25° C. below the $T_m$. The $T_m$ may be estimated using the following relationship: $T_m=69.3+0.41(GC)\%$ (Marmur et al. (1962) *J. Mol. Biol.* 5:109–118).

As used herein, a "biological sample" refers to a sample of tissue or fluid isolated from a subject, that commonly includes antibodies produced by the subject. Typical samples that include such antibodies are known in the art and include but not limited to, blood, plasma, serum, fecal matter, urine, bone marrow, bile, spinal fluid, lymph fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range.

An "antigen" includes any substance that may be specifically bound by an antibody molecule. Thus, the term "antigen" encompasses biologic molecules including, but not limited to, simple intermediary metabolites, sugars, lipids, autoacids, and hormones, as well as macromolecules such as complex carbohydrates, phopholipids, nucleic acids and proteins.

An "immunogen" is a macromolecular antigen that is capable of initiating lymphocyte activation resulting in an antigen-specific immune response. An immunogen therefore includes any molecule which contains one or more epitopes that will stimulate a host's immune system to initiate a secretory, humoral and/or cellular antigen-specific response.

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) *Nature* 349:293–299; and U.S. Pat. No. 4,816,567); F(ab')2 and F(ab) fragments; Fv molecules (noncovalent heterodimers, see, for example, Inbar et al. (1972) *Proc Natl Acad Sci USA* 69:2659–2662; and Ehrlich et al. (1980) *Biochem* 19:4091–4096); single-chain Fv molecules (sFv) (see, e.g., Huston et al. (1988) *Proc Natl Acad Sci USA* 85:5879–5883); dimeric and trimeric antibody fragment constructs; minibodies (see, e.g., Pack et al. (1992) *Biochem* 31:1579–1584; Cumber et al. (1992) *J Immunology* 149B:120–126); humanized antibody molecules (see, e.g., Riechmann et al. (1988) *Nature* 332:323–327; Verhoeyan et al. (1988) *Science* 239:1534–1536; and U.K. Patent Publication No. GB 2,276,169, published 21 Sep. 1994); and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins.

Methods of making polyclonal and monoclonal antibodies are known in the art. Polyclonal antibodies are generated by immunizing a suitable animal, such as a mouse, rat, rabbit, sheep or goat, with an antigen of interest. In order to enhance immunogenicity, the antigen can be linked to a carrier prior to immunization. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as toxoid from diphtheria, tetanus, cholera, etc., in order to enhance the immunogenicity thereof.

Rabbits, sheep and goats are preferred for the preparation of polyclonal sera when large volumes of sera are desired. These animals are good design choices also because of the availability of labeled anti-rabbit, anti-sheep and anti-goat antibodies. Immunization is generally performed by mixing or emulsifying the antigen in saline, preferably in an adjuvant such as Freund's complete adjuvant ("FCA"), and injecting the mixture or emulsion parenterally (generally subcutaneously or intramuscularly). The animal is generally boosted 2–6 weeks later with one or more injections of the antigen in saline, preferably using Freund's incomplete adjuvant ("FIA"). Antibodies may also be generated by in vitro immunization, using methods known in the art. Polyclonal antisera is then obtained from the immunized animal.

Monoclonal antibodies are generally prepared using the method of Kohler and Milstein, Nature (1975) 256:495–497, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention is based on the discovery of novel diagnostic methods for accurately detecting HAV infection in a biological sample. The methods rely on sensitive nucleic acid-based detection techniques that allow identification of HAV target nucleic acid sequences in samples containing small amounts of virus.

In particular, the inventors herein have characterized regions within the HAV genome which are desirable targets for diagnostic tests. Primers and probes derived from these regions are extremely useful for detection of HAV infection in biological samples.

HAV primers and probes described above are used in nucleic acid-based assays for the detection of HAV infection in biological samples. In particular, primers and probes for use in these assays are preferably derived from the nucleotide sequences depicted in FIGS. 1–13 herein.

Particularly preferred primers and probes for use with the present assays are designed from HAV genome to allow detection of HAV infection caused by a variety of isolates.

The four capsid proteins, nonstructural proteins, protease and the junction between the capsid precursor P1 and 2A are readily obtained from additional isolates using portions of the HAV sequence found within these particular regions as primers in PCR reactions such as those described herein. Another method of obtaining nucleotide sequences with the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al. (1991) Proc. Natl. Acad. Sci. USA 88:4084–4088. Once the sequences have been prepared or isolated, they can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

Recombinant clones are readily identified by restriction enzyme analysis and polyacryamide or agarose gel electrophresis, using techniques well known in the art, and described in the examples below.

Polynucleotides of the invention encoding the HAV proteins are useful for designing hybridization probes for isolating and identifying cDNA clones and genomic clones encoding HAV proteins or allelic forms thereof. Such hybridization techniques are known to those of skill in the art. Sequence of polynucleotides that encode HAV proteins are also useful for designing primers for polymerase chain reaction (PCR). Also encompassed by the present invention, are single stranded polynucleotides, hereinafter referred to as antisense polynucleotides, having sequences which are complementary to the RNA sequences which encode the HAV proteins.

Primers and probes for use in the assays herein are derived from these sequences and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) *Tetrahedron* 48:2223–2311; and Applied Biosystems User Bulletin No. 13 (1 Apr. 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109. Poly(A) or poly(C), or other non-complementary nucleotide extensions may be incorporated into probes using these same methods. Hexaethylene oxide extensions may be coupled to probes by methods known in the art. Cload et al. (1991) *J. Am. Chem. Soc.* 113:6324–6326; U.S. Pat. No. 4,914,210 to Levenson et al.; Durand et al. (1990) *Nucleic Acids Res.* 18:6353–6359; and Horn et al. (1986) *Tet. Lett.* 27:4705–4708. Typically, the primer sequences are in the range of between 10–100 nucleotides in length, such as 15–60, 20–40 and so on, more typically in the range of between 20–40 nucleotides long, and any length between the stated ranges. The typical probe is in the range of between 10–100 nucleotides long, such as 10–50, 15–40, 18–30, and so on, and any length between the stated ranges.

Thus, one aspect of the invention encompasses oligonucleotides that are used as primers and probes in polymerase chain reaction (PCR) technologies to amplify transcripts of the genes which encode HAV proteins or portions of such transcripts. Preferably, the primers have a G+C content of 40% or greater. Such oligonucleotides are at least 80% complementary with a sequence of SEQ ID NOs: 1–39. Preferably, the primers and probes are at least 85% complementarity, 90% complementary, 95% complementary or more preferably 98% or 99% complementary with the sense strand or its corresponding antisense strand of SEQ ID NOs: 1–39.

Moreover, the probes may be coupled to labels for detection. There are several means known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al.

(1978) *Nucl. Acids Res.* 5:363–384 which discloses the use of ferritin-avidin-biotin labels; and Chollet et al. (1985) *Nucl. Acids Res.* 13:1529–1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) *Nucl. Acids Res.* 15:3131–3139, Gibson et al. (1987) *Nucl. Acids Res.* 15:6455–6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) *Nucl. Acids Res.* 13:4485–4502 and Spoat et al. (1987) Nucl. Acids Res. 15:4837–4848. A comprehensive review of methodologies for labeling DNA fragments is provided in Matthews et al., *Anal. Biochem.* (1988) 169:1–25.

For example, probes may be fluorescently labeled by linking a fluorescent molecule to the non-ligating terminus of the probe. Guidance for selecting appropriate fluorescent labels can be found in Smith et al., *Meth. Enzymol.* (1987) 155:260–301; Karger et al., *Nucl. Acids Res.* (1991) 19:4955–4962; Haugland (1989) *Handbook of Fluorescent Probes and Research Chemicals* (Molecular Probes, Inc., Eugene, Ore.). Preferred fluorescent labels include fluorescein and derivatives thereof, such as disclosed in U.S. Pat. No. 4,318,846 and Lee et al., *Cytometry* (1989) 10:151–164. Dyes for use in the present invention include 3-pheniyl-7-isocyanatocoumarini, acridines, such as 9-isothiocyanatoacridine and acridine orange, pyrenes, benzoxadiazoles, and stilbenes. Additional dyes include 3-($\epsilon$-carboxypentyl)-3'-ethyl-5,5'-dimethyloxacarbocyanine (CYA); 6-carboxy fluorescein (FAM); 5,6-carboxyrhodamine-110 (R110); 6-carboxyrhodamine-6G (R6G); N',N',N',N'-tetramethyl-6-carboxyrhodamine (TAMRA); 6-carboxy-X-rhodamine (ROX); 2',4',5',7',-tetrachloro-4-7-dichlorofluorescein (TET); 2',7'-dimethoxy-4',5'-6 carboxyrhodamine (JOE); 6-carboxy-2',4,4',5',7,7'-hexachlorofluorescein (HEX); ALEXA; Cy3 and Cy5. These dyes are commercially available from various suppliers such as Applied Biosystems Division of Perkin Elmer Corporation (Foster City, Calif.), and Molecular Probes, Inc. (Eugene, Ore.). Preferred fluorescent labels include fluorescein and derivatives thereof, such as disclosed in U.S. Pat. No. 4,318,846 and Lee et al., *Cytometry* (1989) 10:151–164, and 6-FAM, JOE, TAMRA, ROX, HEX-1, HEX-2, ZOE, TET-1 or NAN-2, and the like.

Additionally, probes can be labeled with an acridinium ester (AE) using the techniques described below. Current technologies allow the AE label to be placed at any location within the probe. See, e.g., Nelson et al. (1995) "Detection of Acridinium Esters by Chemiluminescence" in *Nonisotopic Probing, Blotting and Sequencing*, Kricka L. J.(ed) Academic Press, San Diego, Calif.; Nelson et al. (1994) "Application of the Hybridization Protection Assay (HPA) to PCR" in *The Polymerase Chain Reaction*, Mullis et al. (eds.) Birkhauser, Boston, Mass.; Weeks et al., *Clin. Chem.* (1983) 29:1474–1479; Berry et al., *Clin. Chem.* (1988) 34:2087–2090. An AE molecule can be directly attached to the probe using non-nucleotide-based linker arm chemistry that allows placement of the label at any location within the probe. See, e.g., U.S. Pat. Nos. 5,585,481 and 5,185,439.

The primers and probes described above may be used in polymerase chain reaction (PCR)-based techniques to detect HAV infection in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) *PCR Protocols* (Academic Press, NY 1990); Taylor (1991) *Polymerase chain reaction: basic principles and automation*, in *PCR: A Practical Approach*, McPherson et al. (eds.) IRL Press, Oxford; Saiki et al. (1986) *Nature* 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers which are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grow exponentially with each cycle. Preferably, PCR is carried out with a commercially available thermal cycler, e.g., Perkin Elmer.

RNAs may be amplified by reverse transcribing the mRNA into cDNA, and then performing PCR (RT-PCR), as described above. Alternatively, a single enzyme may be used for both steps as described in U.S. Pat. No. 5,322,770. mRNA may also be reverse transcribed into cDNA, followed by asymmetric gap ligase chain reaction (RT-AGLCR) as described by Marshall et al. (1994) *PCR Meth. App.* 4:80–84.

The fluorogenic 5' nuclease assay, known as the TaqMan™ assay (Perkin-Elmer), is a powerful and versatile PCR-based detection system for nucleic acid targets. Hence, primers and probes derived from regions of the HAV genome described herein can be used in TaqMan™ analyses to detect the presence of infection in a biological sample. Analysis is performed in conjunction with thermal cycling by monitoring the generation of fluorescence signals. The assay system dispenses with the need for gel electrophoretic analysis, and has the capability to generate quantitative data allowing the determination of target copy numbers.

The fluorogenic 5' nuclease assay is conveniently performed using, for example, AmpliTaq Gold™ DNA polymerase, which has endogenous 5' nuclease activity, to digest an internal oligonucleotide probe labeled with both a fluorescent reporter dye and a quencher (see, Holland et al. (1991) *Proc. Natl. Acad.Sci. USA* 88:7276–7280; and Lee et al. (1993) *Nucl. Acids Res.* 21:3761–3766). Assay results are detected by measuring changes in fluorescence that occur during the amplification cycle as the fluorescent probe is digested, uncoupling the dye and quencher labels and causing an increase in the fluorescent signal that is proportional to the amplification of target DNA.

The amplification products can be detected in solution or using solid supports. In this method, the TaqMan™ probe is designed to hybridize to a target sequence within the desired PCR product. The 5' end of the TaqMan™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

In particular, the oligonucleotide probe is constructed such that the probe exists in at least one single-stranded conformation when unhybridized where the quencher molecule is near enough to the reporter molecule to quench the fluorescence of the reporter molecule. The oligonucleotide probe also exists in at least one conformation when hybridized to a target polynucleotide such that the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence unless the probe is either hybridized or digested.

Accordingly, the present invention relates to methods for amplifying a target HAV nucleotide sequence using a nucleic acid polymerase having 5' to 3' nuclease activity, one or more primers capable of hybridizing to the target HAV sequence, and an oligonucleotide probe capable of hybridizing to the target HAV sequence 3' relative to the primer. During amplification, the polymerase digests the oligonucleotide probe when it is hybridized to the target sequence, thereby separating the reporter molecule from the quencher molecule. As the amplification is conducted, the fluorescence of the reporter molecule is monitored, with fluorescence corresponding to the occurrence of nucleic acid amplification. The reporter molecule is preferably a fluorescein dye and the quencher molecule is preferably a rhodamine dye.

While the length of the primers and probes can vary, the probe sequences are selected such that they have a lower melt temperature than the primer sequences. Hence, the primer sequences are generally longer than the probe sequences. Typically, the primer sequences are in the range of between 10–75 nucleotides long, more typically in the range of 20–45. The typical probe is in the range of between 10–50 nucleotides long, more typically 15–40 nucleotides in length.

If a solid support is used, the oligonucleotide probe may be attached to the solid support in a variety of manners. For example, the probe may be attached to the solid support by attachment of the 3' or 5' terminal nucleotide of the probe to the solid support. More preferably, the probe is attached to the solid support by a linker which serves to distance the probe from the solid support. The linker is usually at least 15–30 atoms in length, more preferably at least 15–50 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of probe to the target oligonucleotide. Polyethylene glycol is particularly preferred.

The linkages between the solid support, the linker and the probe are preferably not cleaved during removal of base protecting groups under basic conditions at high temperature. Examples of preferred linkages include carbamate and amide linkages.

Examples of preferred types of solid supports for immobilization of the oligonucleotide probe include controlled pore glass, glass plates, polystyrene, avidin-coated polystyrene beads, cellulose, nylon, acrylamide gel and activated dextran.

For a detailed description of the TaqMan™ assay, reagents and conditions for use therein, see, e.g., Holland et al. (1991) *Proc. Natl. Acad. Sci, U.S.A.* 88:7276–7280; U.S. Pat. Nos. 5,538,848, 5,723,591, and 5,876,930, all incorporated herein by reference in their entireties.

The HAV sequences described herein may also be used as a basis for transcription-mediated amplification (TMA) assays. TMA provides a method of identifying target nucleic acid sequences present in very small amounts in a biological sample. Such sequences may be difficult or impossible to detect using direct assay methods. In particular, TMA is an isothemal, autocatalytic nucleic acid target amplification system that can provide more than a billion RNA copies of a target sequence. The assay can be done qualitatively, to accurately detect the presence or absence of the target sequence in a biological sample. The assay can also provide a quantitative measure of the amount of target sequence over a concentration range of several orders of magnitude. TMA provides a method for autocatalytically synthesizing multiple copies of a target nucleic acid sequence without repetitive manipulation of reaction conditions such as temperature, ionic strength and pH.

Generally, TMA includes the following steps: (a) isolating nucleic acid, including RNA, from the biological sample of interest suspected of being infected with HAV; and (b) combining into a reaction mixture (i) the isolated nucleic acid, (ii) first and second oligonucleotide primers, the first primer having a complexing sequence sufficiently complementary to the 3' terminal portion of an RNA target sequence, if present (for example the (+) strand), to complex therewith, and the second primer having a complexing sequence sufficiently complementary to the 3' terminal portion of the target sequence of its complement (for example, the (−) strand) to complex therewith, wherein the first oligonucleotide further comprises a sequence 5' to the complexing sequence which includes a promoter, (iii) a reverse transcriptase or RNA and DNA dependent DNA polymerases, (iv) an enzyme activity which selectively degrades the RNA strand of an RNA-DNA complex (such as an RNAse H) and (v) an RNA polymerase which recognizes the promoter.

The components of the reaction mixture may be combined stepwise or at once. The reaction mixture is incubated under conditions whereby an oligonucleotide/target sequence is formed, including DNA priming and nucleic acid synthesizing conditions (including ribonucleotide triphosphates and deoxyribonucleotide triphosphates) for a period of time sufficient to provide multiple copies of the target sequence. The reaction advantageously takes place under conditions suitable for maintaining the stability of reaction components such as the component enzymes and without requiring modification or manipulation of reaction conditions during the course of the amplification reaction. Accordingly, the reaction may take place under conditions that are substantially isothermal and include substantially constant ionic strength and pH. The reaction conveniently does not require a denaturation step to separate the RNA-DNA complex produced by the first DNA extension reaction.

Suitable DNA polymerases include reverse transcriptases, such as avian myeloblastosis virus (AMV) reverse transcriptase (available from, e.g., Seikagaku America, Inc.) and Moloney murine leukemia virus (MMLV) reverse transcriptase (available from, e.g., Bethesda Research Laboratories).

Promoters or promoter sequences suitable for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Examples of useful promoters include those which are recognized by certain bacteriophage polymerases such as those from bacteriophage T3, T7 or SP6, or a promoter from *E. coli*. These RNA polymerases are readily available from commercial sources, such as New England Biolabs and Epicentre.

Some of the reverse transcriptases suitable for use in the methods herein have an RNAse H activity, such as AMV reverse transcriptase. It may, however, be preferable to add exogenous RNAse H, such as *E. coli* RNAse H, even when AMV reverse transcriptase is used. RNAse H is readily available from, e.g., Bethesda Research Laboratories.

The RNA transcripts produced by these methods may serve as templates to produce additional copies of the target sequence through the above-described mechanisms. The system is autocatalytic and amplification occurs autocatalytically without the need for repeatedly modifying or changing reaction conditions such as temperature, pH, ionic strength or the like.

Detection may be done using a wide variety of methods, including direct sequencing, hybridization with sequence-specific oligomers, gel electrophoresis and mass spectrometry. these methods can use heterogeneous or homogeneous formats, isotopic or nonisotopic labels, as well as no labels at all.

One preferable method of detection is the use of target sequence-specific oligonucleotide probes, derived from the sequences described in FIGS. 1–13 and fragments thereof. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in *Nonisotopic Probing, Blotting and Sequencing*, Kricka L. J.(ed) Academic Press, San Diego, Calif.; Nelson et al. (1994) "Application of the Hybridization Protection Assay (HPA) to PCR" in *The Polymerase Chain Reaction*, Mullis et al. (eds.) Birkhauser, Boston, Mass.; Weeks et al. (1983) *Clin. Chem.* 29:1474–1479; Berry et al. (1988) *Clin. Chem.* 34:2087–2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon. Additionally, AE causes ester hydrolysis which yields the nonchemiluminescent-methyl acridinium carboxylic acid.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally consists of the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. Preferably, the differential hydrolysis step is conducted at the same temperature as the hybridization step, typically at 50 to 70° C. Alternatively, a second differential hydrolysis step may be conducted at room temperature. This allows elevated pHs to be used, for example in the range of 10–11, which yields larger differences in the rate of hydrolysis between hybridized and unhybridized AE-labeled probe. HPA is described in detail in, e.g., U.S. Pat. Nos. 6,004,745; 5,948,899; and 5,283,174, the disclosures of which are incorporated by reference herein in their entireties.

TMA is described in detail in, e.g., U.S. Pat. No. 5,399,491, the disclosure of which is incorporated herein by reference in its entirety. In one example of a typical assay, an isolated nucleic acid sample, suspected of containing a HAV target sequence, is mixed with a buffer concentrate containing the buffer, salts, magnesium, nucleotide triphosphates, primers, dithiothreitol, and spermidine. The reaction is optionally incubated at about 100° C. for approximately two minutes to denature any secondary structure. After cooling to room temperature, reverse transcriptase, RNA polymerase, and RNAse H are added and the mixture is incubated for two to four hours at 37° C. The reaction can then be assayed by denaturing the product, adding a probe solution, incubating 20 minutes at 60° C., adding a solution to selectively hydrolyze the unhybridized probe, incubating the reaction six minutes at 60° C., and measuring the remaining chemiluminescence in a luminometer.

As is readily apparent, design of the assays described herein are subject to a great deal of variation, and many formats are known in the art. The above descriptions are merely provided as guidance and one of skill in the art can readily modify the described protocols, using techniques well known in the art.

The above-described assay reagents, including the primers, probes, solid support with bound probes, as well as other detection reagents, can be provided in kits, with suitable instructions and other necessary reagents, in order to conduct the assays as described above. The kit will normally contain in separate containers the combination of primers and probes (either already bound to a solid matrix or separate with reagents for binding them to the matrix), control formulations (positive and/or negative), labeled reagents when the assay format requires sane and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular assay used, other packaged reagents and materials (i.e. wash buffers and the like). Standard assays, such as those described above, can be conducted using these kits.

Recombinant or synthetic HAV polypeptides can be used as diagnostics, or those which produce an immunological response, such as those that give rise to neutralizing antibodies, may be formulated into vaccines. Antibodies raised against these polypeptides can also be used as diagnostics, or for passive immunotherapy. In addition, antibodies to these polypeptides are useful for isolating and identifying HAV particles. The HAV antigens may also be isolated from HAV virions. The virions may be grown in HAV infected cells in tissue culture, or in an infected host.

Particularly, the antibodies may be polyclonal or monoclonal, may be a human antibody, or may be a hybrid or chimeric antibody, such as a humanized antibody, an altered antibody, F(ab')$_2$ fragments, F(ab) fragments, Fv fragments, a single-domain antibody, a dimeric or trimeric antibody fragment construct, a minibody, or functional fragments thereof which bind to the analyte of interest. Antibodies are produced using techniques well known to those of skill in the art and disclosed in, for example, U.S. Pat. Nos. 4,011,308; 4,722,890; 4,016,043; 3,876,504; 3,770,380; and 4,372,745.

For example, polyclonal antibodies are generated by immunizing a suitable animal, such as a mouse, rat, rabbit, sheep or goat, with an antigen of interest. In order to enhance immunogenicity, the antigen can be linked to a carrier prior to immunization. Such carriers are well known to those of ordinary skill in the art. Immunization is generally performed by mixing or emulsifying the antigen in saline, preferably in an adjuvant such as Freund's complete adjuvant, and injecting the mixture or emulsion parenterally (generally subcutaneously or intramuscularly). The animal is generally boosted 2–6 weeks later with one or more injections of the antigen in saline, preferably using Freund's incomplete adjuvant. Antibodies may also be generated by in vitro immunization, using methods known in the art. Polyclonal antiserum is then obtained from the immunized animal.

Monoclonal antibodies are generally prepared using the method of Kohler and Milstein (1975) *Nature* 256:495–497, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice). Human monoclonal antibodies are obtained by using human rather than murine hybridomas. See, e.g., Cote, et. al. *Monclonal Antibodies and Cancer Therapy*, Alan R. Liss, 1985, p. 77

Monoclonal antibodies or portions thereof may be identified by first screening a B-cell cDNA library for DNA molecules that encode antibodies that specifically bind to p185, according to the method generally set forth by Huse et al. (1989) *Science* 246:1275–1281. The DNA molecule may then be cloned and amplified to obtain sequences that encode the antibody (or binding domain) of the desired specificity.

As explained above, antibody fragments which retain the ability to recognize the molecule of interest, will also find use in the subject invention. A number of antibody fragments are known in the art which comprise antigen-binding sites capable of exhibiting immunological binding properties of an intact antibody molecule. For example, functional antibody fragments can be produced by cleaving a constant region, not responsible for antigen binding, from the antibody molecule, using e.g., pepsin, to produce F(ab')$_2$ fragments. These fragments will contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques such as recombinant production or preferential proteolytic cleavage of immunoglobulin molecules. These fragments are known as $F_v$. See, e.g., Inbar et al. (1972) *Proc. Nat. Acad. Sci. USA* 69:2659–2662; Hochman et al. (1976) *Biochem* 15:2706–2710; and Ehrlich et al. (1980) *Biochem* 19:4091–4096.

A single-chain Fv ("sFv"or "scFv") polypeptide is a covalently linked $V_H$-$V_L$ heterodimer which is expressed from a gene fusion including $V_H$- and $V_L$-encoding genes linked by a peptide-encoding linker. Huston et al. (1988) *Proc. Nat. Acad. Sci. USA* 85:5879–5883. A number of methods have been described to discern and develop chemical structures (linkers) for converting the naturally aggregated, but chemically separated, light and heavy polypeptide chains from an antibody V region into an sFv molecule which will fold into a three dimensional structure substantially similar to the structure of an antigen-binding site. See, e.g., U.S. Pat. Nos. 5,091,513, 5,132,405 and 4,946,778. The sFv molecules may be produced using methods described in the art. See, e.g., Huston et al. (1988) *Proc. Nat. Acad. Sci. USA* 85:5879–5883; U.S. Pat. Nos. 5,091,513, 5,132,405 and 4,946,778. Design criteria include determining the appropriate length to span the distance between the C-terminus of one chain and the N-terminus of the other, wherein the linker is generally formed from small hydrophilic amino acid residues that do not tend to coil or form secondary structures. Such methods have been described in the art. See, e.g., U.S. Pat. Nos. 5,091,513, 5,132,405 and 4,946,778. Suitable linkers generally comprise polypeptide chains of alternating sets of glycine and serine residues, and may include glutamic acid and lysine residues inserted to enhance solubility.

"Mini-antibodies" or "minibodies" will also find use with the present invention. Minibodies are sFv polypeptide chains which include oligomerization domains at their C-termini, separated from the sFv by a hinge region. Pack et al. (1992) *Biochem* 31: 1579–1584. The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992) *Biochem* 31:1579–1584; Cumber et al. (1992) *J Immunology* 149B:120–126.

While the polypeptides of the present invention may comprise a substantially complete viral domain, in many applications all that is required is that the polypeptide comprise an antigenic or immunogenic region of the virus. Thus, in one aspect of the invention, the polypeptides of SEQ ID Nos: 40–48 are used to elicit an immunological response. In another aspect of the invention, an immunological region of a polypeptide is generally relatively small—typically 8 to 10 amino acids or less in length. Fragments of as few as 5 amino acids may characterize an antigenic region. These segments may correspond to regions encoding for capsid proteins, nonstructural proteins, and the junction between the capsid precursor P1 and 2A. Accordingly, using the cDNAs of these regions as a basis, DNAs encoding short segments of these polypeptides can be expressed recombinantly either as fusion proteins, or as isolated polypeptides. In addition, short amino acid sequences can be conveniently obtained by chemical synthesis.

In instances wherein the synthesized polypeptide is correctly configured so as to provide the correct epitope, but is too small to be immunogenic, the polypeptide may be linked to a suitable carrier. A number of techniques for obtaining such linkage are known in the art, including the formation of disulfide linkages using N-succinimidyl-3-(2-pyridyl-thio) propionate (SPDP) and succinimidyl 4-(N-maleimido-methyl)cyclohexane-1-carboxylate (SMCC) obtained from Pierce Company, Rockford, Ill., (if the peptide lacks a sulfhydryl group, this can be provided by addition of a cysteine residue). These reagents create a disulfide linkage between themselves and peptide cysteine residues on one protein and an amide linkage through the epsilon-amino on a lysine, or other free amino group in the other. A variety of such disulfide/amide-forming agents are known. See, for example, Immun. Rev. (1982) 62:185. Other bifunctional coupling agents form a thioether rather than a disulfide linkage. Many of these thio-ether-forming agents are commercially available and include reactive esters of 6maleimidocaproic acid, 2-bromoacetic acid, 2-iodoacetic acid, 4-(N-maleimido-methyl)cyclohexane-1-carboxylic acid, and the like. The carboxyl groups can be activated by combining them with succinimide or 1-hydroxyl-2-nitro-4sulfonic acid, sodium salt. Additional methods of coupling antigens employs the rotavirus/"binding peptide" system described in EPO Pub. No. 259,149, the disclosure of which is incorporated herein by reference. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysaccharides, such as latex functionalized Sepharose™, agarose, cellulose, cellulose beads and the like; polymeric amino acids, such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, tetanus toxoid, and other proteins well known to those skilled in the art.

In addition to the polypeptides comprising SEQ ID NOs: 40–48, polypeptides comprising truncated HAV amino acid sequences encoding at least one viral epitope are useful immunological reagents. For example, polypeptides comprising such truncated sequences can be used as reagents in an immunoassay. These polypeptides also are candidate subunit antigens in compositions for antiserum production or vaccines. While these truncated sequences can be produced by various known treatments of native viral protein, it is generally preferred to make synthetic or recombinant polypeptides comprising an HAV sequence. Polypeptides comprising these truncated HAV sequences can be made up entirely of HAV sequences (one or more epitopes, either contiguous or noncontiguous), or HAV sequences and heterologous sequences in a fusion protein. Useful heterologous sequences include sequences that provide for secretion from a recombinant host, enhance the immunological reactivity of the HAV epitope(s), or facilitate the coupling of the polypeptide to an immunoassay support or a vaccine carrier. See, e.g., EPO Pub. No. 116,201; U.S. Pat. No. 4,722,840; EPO Pub. No. 259,149; U.S. Pat. No. 4,629,783, the disclosures of which are incorporated herein by reference.

The size of polypeptides comprising the truncated HAV sequences can vary widely, the minimum size being a sequence of sufficient size to provide an HAV epitope, while the maximum size is not critical. In some applications, the maximum size usually is not substantially greater than that required to provide the desired HAV epitopes and function (s) of the heterologous sequence, if any. Typically, the truncated HAV amino acid sequence will range from about 5 to about 100 amino acids in length. More typically, however, the HAV sequence will be a maximum of about 50 amino acids in length, preferably a maximum of about 30 amino acids. It is usually desirable to select HAV sequences of at least about 10, 12 or 15 amino acids, up to a maximum of about 20 or 25 amino acids. In another aspect, the truncated HAV amino acid sequence are selected from SEQ ID NOs: 40–48. In yet another aspect of the invention, the polynucleotides or the truncated amino acid sequences have at least about 50% homology to the polynucleotides of SEQ ID NOs: 40–48, preferably about 80% homology to the polynucleotides of SEQ ID NOs: 40–48, more preferably about 90%, 95%, or 99% homology to the polynucleotides of SEQ ID NOs: 40–48.

Truncated HAV amino acid sequences comprising epitopes can be identified in a number of ways. For example, the entire viral protein sequence can be screened by preparing a series of short peptides that together span the entire protein sequence. By starting with, for example, 100-mer polypeptides, it would be routine to test each polypeptide for the presence of epitope(s) showing a desired reactivity, and then testing progressively smaller and overlapping fragments from an identified 100-mer to map the epitope of interest. Screening such peptides in an immunoassay is within the skill of the art. It is also known to carry out a computer analysis of a protein sequence to identify potential epitopes, and then prepare oligopeptides comprising the identified regions for screening. It is appreciated by those of skill in the art that such computer analysis of antigenicity does not always identify an epitope that actually exists, and can also incorrectly identify a region of the protein as containing an epitope.

The immunogenicity of the HAV sequences may also be enhanced by preparing the sequences fused to or assembled with particle-forming proteins such as, for example, hepatitis B surface antigen or rotavirus VP6 antigen. Constructs wherein the HAV epitope is linked directly to the particle-forming protein coding sequences produce hybrids which are immunogenic with respect to the HAV epitope. In addition, all of the vectors prepared include epitopes specific to HAV, having various degrees of immunogenicity, such as, for example, the pre-S peptide. Thus, particles constructed from particle forming protein which include HAV sequences are immunogenic with respect to HAV and particle-form protein.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

In the following examples, enzymes were purchased from commercial sources, and used according to the manufacturers' directions. Nitrocellulose filters and the like were also purchased from commercial sources.

In the isolation of DNA fragments, except where noted, all DNA manipulations were done according to standard procedures. See, Sambrook et al., supra. Restriction enzymes, $T_4$ DNA ligase, *E. coli*, DNA polymerase I, Klenow fragment, and other biological reagents can be purchased from commercial suppliers and used according to the manufacturers' directions. Double stranded DNA fragments were separated on agarose gels.

EXAMPLE 1

Hepatitis A Nucleic Acid Extraction for RT-PCR

Human serum samples that had previously tested positive for HAV by IgM anti-HAV ELISA [ETI-HA-IgMK PLUS; DiaSorin, Inc; Saluggia (VC), Italy] were used to isolate RNA for subsequent experiments. Samples were stored at −80° C. until used. RNA was extracted from 0.14 mL of serum using the QIAamp Viral Mini Spin Kit (QIAGEN, Valencia, Calif.) following the manufacturer's specifications.

EXAMPLE 2

Detection of Hepatitis A Nucleic Acid-Positive Samples by RT-PCR

The RT-PCR was performed using the Titan One Tube RT-PCR Kit (Roche, Mannheim, Germany) to amplify a 243bp fragment in the VP3/VP1 region. The 243bp fragment corresponds to nucleotide positions 2172–2415 of the HAV genome as reported by Cohen et al. (1987) *J. Virol.* 61: 50–59.

Experiments were performed using the primers shown in Table 1 and the procedures described below.

TABLE 1

Primers used in the "RT-PCR" Experiments

| Primer | Sequence | PCR product | Genomic region | SEQ ID NO: |
|---|---|---|---|---|
| SN2172 | GCTCCTCTTTATCATGCTATGGAT | 243 bp | VP3/VP1 | 49 |
| SN2415 | CAGGAAATGTCTCAGGTACTTTCT | 243 bp | VP3/VP1 | 50 |

For this experiment, the "RT-PCR" was performed in a final volume of 50 µL using 10 µL of extracted HAV RNA following the manufacturer's specifications. The amplification profile involved reverse transcription at 50° C. for 30 min., template denaturation at 94° C. for 2 min., denaturation at 94° C. for 30 sec., primer annealing at 55° C. for 30 sec. and elongation at 68° C. for 45 sec. for 40 cycles. A final 10 min. incubation at 68° C. to ensure the full extension of fragments followed the 40 PCR cycles.

PCR products were electrophoresed on 4–20% polyacrylamide gels, stained with ethidium bromide and visualized under an UV source. Purification of amplified fragments was carried out using the QiaQuick PCR purification kit (QIAGEN, Valencia, Calif.).

EXAMPLE 3

Cloning of Hepatitis A fragments

The PCR fragments were cloned into TOPO-TA vectors (Invitrogen, Carlsbad, Calif.). Cloning into these vectors is highly facilitated when the amplified DNA contains a single deoxyadenosine (A) at its 3' end. Accordingly, a catalytic reaction to add the 3' (A) overhead was used. The reaction mix contained 1.25 mM of dATP, 0.5 units of Taq polymerase (Perkin Elmer, Boston, Mass.) and proceeded at 72 C for 15 min.

PCR fragments were cloned into the pCR2.1-TOPO vector using the Invitrogen's TA cloning kit (TOPO™ TA Cloning$^R$ Kit with One Shot TOP10 Electrocompetent Cells) following the manufacturer's specifications. Bacterial cells were incubated at 37° C. on Luria Broth plates containing ampicillin at 100 µg/mL, 0.66 mM IPTG and 0.033% X-Gal. A number of white colonies were inoculated in 4 mL of Luria-Broth ampicillin (100 µg/ml) and incubated overnight at 37° C. with shaking. Three mL of the overnight cultures were used to prepare plasmid DNA using the QIAprep Miniprep kit (QIAGEN). Recombinant clones were identified by restriction enzyme analysis with EcoRI (New England and Biolabs) and 4–20% polyacryamide electrophoresis as described above.

In order to determine the DNA sequences of the clones, large amounts of plasmids from recombinant clones were prepared as above and the DNA suspended in TE (10 mM Tris-HCl, pH 8.0, 1 mM EDTA) at 0.2 mg/mL. Nucleotide sequence determination of the Hepatitis A fragments was performed using an Applied Biosystems Model 373 or Model 377 DNA Sequencer system (Foster City, Calif.). The nucleotide sequence of the 243 bp VP3/VP1 fragment determined for 13 Indonesian (IND) (SEQ ID NOs: 1–13) and 14 Chilean (SCL) (SEQ ID NOs: 14–27) HAV isolates is shown in FIG. 1.

EXAMPLE 4

Cloning of HAV Nucleotide Sequences in Vectors Suitable for in vitro Transcription of Viral RNA Cloning of HAV P1/2A precursor and full length open reading frame nucleotide fragments of interest include PCR of fragments of interest from the Chiron plasmid pHAVFL 18.3 #2 already containing a full length ORF of HAV and cloning those fragments of interest into the pGEM-4z vector (Promega, Madison Wis.). The pGEM vector has both an SP6 and T7 promoter to facilitate in vitro RNA synthesis of cloned products. The pGEM-4z vector was made by restriction digest of the plasmid using KpnI and SphI restriction enzymes (Roche Applied Science, Indianapolis, Ind.) followed by a phosphatase reaction using shrimp alkaline phosphatase (Roche Applied Science). The vector was then electrophoresed on an agarose gel and purified using the Promega Wizard PCR Purification kit (Promega).

Primers were designed to flank the regions of interest and included the KpnI and SphI restriction sites to facilitate cloning. Primers were ordered from an in-house DNA synthesis facility. PCR reactions using pHAVFL 18.3 #2 as template were done using the Roche Expand High Fidelity PCR System following the manufacturer's recommendations. The PCR products were electrophoresed on an agarose gel and purified using the Promega Wizard PCR Purification kit (Promega).

The PCR products were ligated into the pGEM-4z vector using Roche Rapid DNA Ligation kit (Roche Applied Science) and transformed into HB101 competent cells. Bacterial cells were incubated at 37° C. on Luria Broth plates containing ampicillin at 100 µg/mL overnight. Three mL of overnight cultures were used to prepare plasmid DNA using the QIAprep Miniprep kit (QIAGEN, Valencia Calif.). Recombinant clones were identified by restriction enzyme analysis with KpnI and SphI (Roche Applied Science) and gel electrophoresed.

Cloning of HAV full length open reading frame plus additional 3' untranslated sequences include insertion of the HAV fragment from KpnI-DrdI from the above described HAV full length cloned fragment and a synthetic DNA region from DrdI-SphI into the pGEM-4z KpnI-SphI vector described above.

Restriction enzyme digest was done on the pGEM-4z full length HAV construct described above to isolate a fragment using KpnI and DrdI enzymes (Roche Applied Science). The digest was electrophoresed and purified using the Promega Wizard PCR Purification kit (Promega). Synthetic DNA oligos were designed and ordered from an in-house DNA synthesis facility. The synthetic DrdI-SphI region was annealed from separate oligos and kinased according to standard molecular biology protocol. The two separate fragments were then ligated into the pGEM-4z vector using Roche Rapid DNA Ligation kit (Roche Applied Science) and transformed into HB101 competent cells. Bacterial cells were incubated at 37° C. on Luria Broth plates containing ampicillin at 100 µg/mL overnight. Three mL of the overnight cultures were used to prepare plasmid DNA using the QIAprep Miniprep kit (Qiagen, Valencia Calif.). Recombinant clones were identified by restriction enzyme analysis with KpnI and SphI (Roche Applied Science) and gel electrophoresed.

Large amounts of plasmids from recombinant clones were prepared using Qiagen Maxi Plasmid kit (Qiagen) and the DNA suspended in ddH$_2$O at 0.2 mg/mL. Nucleotide sequence determination of the HAV fragments was performed using an Applied BioSystems Model 373 or Model 377 DNA Sequencer system. The nucleotide sequence of the HAV inserts cloned in the pGEM-4z vector is shown in FIGS. 2–4.

EXAMPLE 5

Cloning and Expression of HAV P1, P1-2A, 1B, 1C, 1D, SOD-2A and SOD-3A Recombinant Proteins Fragments encoding for P1, P1-2A, 1B, 1C, 1D, 2A and 3A were amplified using the DNA of a recombinant plasmid obtained in Chiron Corporation which contains the full-length HAV coding reading frame cloned in pUC18. PCR primers were designed to PCR out the P1, P1-2A, 1B, 1C, 1D, 2A and 3A regions of HAV. To facilitate the cloning of these regions into Chiron yeast expression vectors the NcoI, XhoI, and SalI restriction sites were introduced in the primers as required.

PCR primers were synthesized in the DNA synthesis facility of Chiron Corporation. Synthetic oligonucleotides were purified, suspended in 300 ul of dH$_2$O and their optical densities at 260 nm determined. The reaction mix contained 0.25 ng of template, 100 pmol of each primer, 10 ul of 1.25 mM of each DNTP and 1 unit of Taq polymerase (Vendor) in a final volume of 50 uL. Amplification conditions were 94° C. for 1 min., 50° C. for 2 min. and 68° C. for 4 min. for 35 cycles. A 7-min. post incubation at 75° C. was added to ensure the full extension of fragments. Aliquots of 5 µL were used to check PCR synthesis by electrophoresis on 1% agarose gels. The entire PCR product was then electrophoresed and fragments exhibiting the expected sizes were purified from the gels using the PCR Purification kit (Promega) following the vendor's recommendations. Approximately 0.8 µg of purified PCR DNA was digested with the appropriate restriction enzymes (Roche) for 3h at 37° C. and the products were further purified using the Promega PCR Purification kit.

Plasmid pBS24.1, that was engineered to contain the yeast hybrid promoter ADH2/GAPDH (Cousens et al. (1987) *Gene* 61, 265–275) and an XhoI restriction site, was used for heterologous expression of the HAV recombinant proteins. This yeast expression vector contains 2µ sequences and inverted repeats (IR) for autonomous replication in yeast, the α-factor terminator to ensure transcription termination, and the yeast leu2-d and URA3 for selection. The ColE1 origin of replication and the β-lactamase gene are also present for propagation and selection in *E. coli* (Pichuantes et al. (1996) "Expression of Heterologous Gene Products in Yeast" in *Protein Engineering A Guide to Design and Production*, Chapter 5. J. L. Cleland and C. Craik, eds., Wiley-Liss, Inc., New York, N.Y. pp 129–161). Plasmid pBS24.1 was digested with BamHI/SalI or XhoI/SalI and dephosphorylated with 10 units of calf intestine alkaline phosphatase (Boheringer Manheim, Indianapolis, Ind.) under the conditions recommended by the vendor. The HAV nucleotide sequences coding for HAV 2A and 3A were fused to DNA sequences coding for the human superoxide dismutase (SOD) prior to the cloning. The digested and purified HAV recombinant fragments were ligated with digested pBS24.1 using the Roche Rapid Ligation kit and protocol. The ligation mix was then used to transform *Escherichia coli* HB101 competent cells and transformants were selected in Luria-Broth plates containing ampicillin at 100 μg/mL after an overnight incubation at 37° C. Several colonies of each transformation were picked and inoculated in 3 mL of Luria-Broth with ampicillin at 100 μg/mL and incubated at 37° C. with shaking overnight. Plasmid DNA was prepared using 1.5 mL of cultures and the QIAprep Miniprep kit (QIAGEN). Recombinant clones were identified by analytical restriction enzyme analysis with BamHI-SalI. Large-scale preparations of recombinant plasmids were made to perform sequencing to confirm the nucleotide sequence of the cloned HAV fragments. Yeast expression plasmids exhibiting the expected sequence for HAV P1, P1-2A, 1B, 1C, 1D, SOD-2A and SOD-3A were used in experiments of yeast transformation as follows. Competent *Saccharomyces cerevisiae* AD3 cells [Mat a, trp1+, ura3-52, prb1-1122, pep4-3, prc1-407, [$cir^0$],::pDM15(pGAP/ADR1::$G418^R$)], leu2(ΔAD)]were transformed with plasmid DNAs encoding for NS1, VP1 or VP2. Selection of yeast recombinants was achieved by two rounds of uracil-deficient plates followed by one round of leucine-deficient plates after incubation at 30° C. for 48–72 hours. Cultures were then grown in leucine-deficient media and then in YEP supplemented with 2% glucose (Pichuantes et al. (1989) Proteins: Struct. Funct. Genet. 6: 324–337) for 48 h before checking expression of the recombinant proteins.

The nucleotide (SEQ ID NOs: 31–39) and corresponding amino acid sequences for the various proteins (SEQ ID NOs: 40–48) are shown in FIGS. 5–13. The amino acid sequence of the polypeptides was deduced from the nucleotide sequences. The nucleotide sequences and the amino acid sequences were compared to the wild-type HAV nucleotide and protein sequences reported by Cohen et al. (1987) J. Virol. 61:50–59. The polynucleotide sequences from the Indonesian samples have a 93.8–96.7% homology, while the polynucleotide sequences from the Chilean samples have a 90.5–94.7% homology. The amino acid sequences from the Indonesian and the Chilean samples have a homology of 98.8–100% and 97.5–98.8%, respectively.

Accordingly, novel hepatitis A virus sequences and detection assays using these sequences have been disclosed. From the foregoing, it will be appreciated that, although specific embodiments of the invention have been described herein for purposes of illustration, various modifications may be made without deviating from the spirit and scope thereof.

We claim:

1. An isolated polynucleotide comprising:
   (a) a nucleotide sequence comprising the nucleotide sequence of SEQ ID NO: 15;
   (b) a sequence complementary to the sequence of (a); or
   (c) a fragment of either of the sequences in (a) or (b) wherein the fragment comprises at least 15 contiguous nucleotides of SEQ ID NO: 15 or of the complement of SEQ ID NO: 15.

2. The polynucleotide of claim 1, wherein the nucleotide sequence comprises the sequence of SEQ ID NO: 15.

3. A method for detecting Hepatitis A virus (HAV) infection in a biological sample, the method comprising:
   (a) isolating nucleic acid from a biological sample suspected of containing Hepatitis A virus (HAV) RNA, wherein said nucleic acid comprises a target sequence;
   (b) reacting the HAV nucleic acid with a detectably labeled probe sufficiently complementary to and capable of hybridizing with the target sequence, wherein the probe is a polynucleotide according to claim 1, and further wherein said reacting is done under conditions that provide for the formation of a probe/target sequence complex; and
   (c) detecting the presence or absence of label as an indication of the presence or absence of the target sequence.

4. The method of claim 3, wherein the probe comprises a detectable label at the 5'-end and/or at the 3'-end.

5. The method of claim 3, wherein the detectable label is a fluorescent label selected from the group consisting of 6-carboxyfluorescein (6-FAM), tetramethyl rhodamine (TAMRA), and 2', 4', 5', 7',-tetrachloro-4-7-dichlorofluorescein (TET).

6. A method for detecting Hepatitis A virus (HAV) infection in a biological sample, the method comprising:
   isolating nucleic acids from a biological sample suspected of containing HAV;
   amplifying the nucleic acids using at least two primers wherein each of the primers is not more than about 50 nucleotides in length and comprises a nucleotide sequence of at least 10 contiguous nucleotides from a polynucleotide according to claim 1 or a nucleotide sequence having 90% sequence identity thereto, wherein each of the two primer is sufficiently complementary to a portion of the sense and antisense strands, respectively, of the isolated nucleic acid to hybridize therewith; and
   detecting the of the amplified nucleic acids as an indication of the presence or absence of HAV in the sample.

\* \* \* \* \*

```
                         SEQUENCE LISTING

<160> NUMBER OF SEQ ID NOS: 50

<210> SEQ ID NO 1
<211> LENGTH: 245
<212> TYPE: DNA
<213> ORGANISM: Artificial Sequence
<220> FEATURE:
<223> OTHER INFORMATION: Description of Artificial Sequence: IND-1-2

<400> SEQUENCE: 1
tgctcctctt tatcatgcta tggatgtcac cacacaggtt ggagatgatt ccggaggttt     60
ttcaacgaca gtttctacag agcagaatgt tccagatccc caagttggta taacaactat    120
gaaggattta aaaggaaaag ccaatagagg gaaaatggat gtttcaggag tacaagcacc    180
tgtgggagct attacaacaa ttgaggatcc agttttagca aagaaagtac ctgagacatt    240
tcctg                                                                245

<210> SEQ ID NO 2
<211> LENGTH: 245
<212> TYPE: DNA
<213> ORGANISM: Artificial Sequence
<220> FEATURE:
<223> OTHER INFORMATION: Description of Artificial Sequence: IND-2-2

<400> SEQUENCE: 2
gctcctcttt atcatgctat ggatgtcacc acacaggttg gagatgattc cggaggtttt     60
tcaacgacag tttctacaga gcagaatgtt cctgatcccc aagttggcat aacaaccatg    120
agggacttaa aagggaaagc caataggggg aagatggatg tttcaggagt gcaagcacct    180
gtgggagcta ttacaacaat tgaggatcca gttttagcaa agaaagtacc tgagacattt    240
cctga                                                                245
```

<210> SEQ ID NO 3
<211> LENGTH: 245
<212> TYPE: DNA
<213> ORGANISM: Artificial Sequence
<220> FEATURE:
<223> OTHER INFORMATION: Description of Artificial Sequence: IND-2-4

<400> SEQUENCE: 3

```
tgctcctctt tatcatgcta tggatgtcac cacacaggtt ggagatgatt ccggaggttt     60
ttcaacgaca gtttctacag agcagaatgt tccagatccc caagttggta taacaaccat    120
gagggattta aaaggaaaag ccaatagagg gaaaatggat gtttcaggag tacaagcacc    180
tgtgggagct attacaacaa ttgaggatcc agttttagca aagaaagtac ctgagacatt    240
tcctg                                                                245
```

<210> SEQ ID NO 4
<211> LENGTH: 245
<212> TYPE: DNA
<213> ORGANISM: Artificial Sequence
<220> FEATURE:
<223> OTHER INFORMATION: Description of Artificial Sequence: IND-3-2

<400> SEQUENCE: 4

```
tgctcctctt tatcatgcta tggatgtcac cacacaggtt ggagatgatt ccggaggttt     60
ttcaacaaca gtttctacag agcagaatgt tcctgatccc caagttggca taacaaccat    120
gagggattta aaagggaaag ctaatagggg aaagatggat gtgtcaggag tgcaagcacc    180
tgtgggagcc atcacaacaa ttgaggatcc agttttagca aagaaagtac ctgagacatt    240
tcctg                                                                245
```

<210> SEQ ID NO 5
<211> LENGTH: 245
<212> TYPE: DNA
<213> ORGANISM: Artificial Sequence
<220> FEATURE:
<223> OTHER INFORMATION: Description of Artificial Sequence: IND-4-5

<400> SEQUENCE: 5

```
gctcctcttt atcatgctat ggatgtcacc acacaggttg agatgattc cggaggtttt      60 tcaacgacag tttctacaga gcagaatgtt ccagatcccc aagttggtat aacaactatg    120
aaggatttaa aaggaaaagc caatagaggg aaaatggatg tttcaggagt acaagcacct    180
gtgggagcta tcacaacaat tgaggatcca gttttagcaa agaaagtacc tgagacattt    240
cctga                                                                245
```

<210> SEQ ID NO 6
<211> LENGTH: 245
<212> TYPE: DNA
<213> ORGANISM: Artificial Sequence
<220> FEATURE:
<223> OTHER INFORMATION: Description of Artificial Sequence: IND-6-4

<400> SEQUENCE: 6

```
tgctcctctt tatcatgcta tggatgtcac cacacaggtt ggagatgatt ccggaggttt     60
ttcaacgaca gtttctacag agcagaatgt tccagatccc caagttggta taacaactat    120
gaaggattta aaaggaaaag ccaatagagg gaaaatggat gtttcaggag tacaagcacc    180
tgtgggagct attacaacag ttgaggatcc agttttagca aagaaagtac ctgagacatt    240
```

-continued

```
tcctg                                                          245

<210> SEQ ID NO 7
<211> LENGTH: 245
<212> TYPE: DNA
<213> ORGANISM: Artificial Sequence
<220> FEATURE:
<223> OTHER INFORMATION: Description of Artificial Sequence: IND-7-1

<400> SEQUENCE: 7
gctcctcttt atcatgctat ggatgtcacc acacaggttg gagatgattc cggaggtttt    60
tcaacgacag tttctacaga gcagaatgtt ccagatcccc aagttggtat aacaactatg   120
aaggatttaa aaggaaaagc aatagaggg aaaatggatg tttcaggagt acaagcacct   180
gtgggagcta ttacaacagt tgaggatcca gttttagcaa agaaagtacc tgagacattt   240
cctga                                                          245

<210> SEQ ID NO 8
<211> LENGTH: 245
<212> TYPE: DNA
<213> ORGANISM: Artificial Sequence
<220> FEATURE:
<223> OTHER INFORMATION: Description of Artificial Sequence: IND-8-2

<400> SEQUENCE: 8
gctcctcttt atcatgctat ggatgtcacc acacaggttg gagatgattc cggaggtttt    60
tcaacgacag tttctacaga gcagaatgtt ccagatcccc aagttggtat aacaactatg   120
aaggatttaa aaggaaaagc aatagaggg aaaatggatg tttcaggagt acaagcacct   180
gtgggagcta ttacaacagt tgaggatcca gttttagcaa agaaagtacc tgagacattt   240
cctga                                                          245

<210> SEQ ID NO 9
<211> LENGTH: 245
<212> TYPE: DNA
<213> ORGANISM: Artificial Sequence
<220> FEATURE:
<223> OTHER INFORMATION: Description of Artificial Sequence: IND-9-1

<400> SEQUENCE: 9
tgctcctctt tatcatgcta tggatgtcac cacacaggtt ggagatgatt ccggaggttt    60
ttcaacgaca gtttctacag agcagaatgt tccagatccc caagttggta taacaactat   120
gaaggattta aaggaaaag ccaatagagg gaaaatggat gtttcaggag tacaagcacc   180
tgtgggagct attacaacag ttgaggatcc agttttagca agaaagtac ctgagacatt   240 tcctg                                                          245

<210> SEQ ID NO 10
<211> LENGTH: 245
<212> TYPE: DNA
<213> ORGANISM: Artificial Sequence
<220> FEATURE:
<223> OTHER INFORMATION: Description of Artificial Sequence: IND-10-5

<400> SEQUENCE: 10
tgctcctctt tatcatgcta tggatgtcac cacacaggtt ggagatgatt ccggaggttt    60
ttcaacgaca gtttctacag agcagaatgt tcctggtccc caagttggca taacaaccat   120
gagggactta aagggaaag ccaataggg gaagatggat gtttcaggag tgcaagcacc   180
tgtgggagct attacaacaa ttgaggatcc agttttagca agaaagtac ctgagacatt   240
``` tcctg                                                          245

<210> SEQ ID NO 11
<211> LENGTH: 245
<212> TYPE: DNA
<213> ORGANISM: Artificial Sequence
<220> FEATURE:
<223> OTHER INFORMATION: Description of Artificial Sequence: IND-11-5

<400> SEQUENCE: 11
tgctcctctt tatcatgcta tggatgtcac cacacaggtt ggagatgatt ccggaggttt      60
ttcaacgaca gtttctacag agcagaatgt tccagatccc caagttggta taacaactat    120
gaaggattta aaaggaaaag ccaatagagg gaaaatggat gtttcaggag tacaagcacc    180
tgtgggagct attacaacaa ttgaggatcc agttttagca aagaaagtac ctgagacatt    240
tcctg                                                                245

<210> SEQ ID NO 12
<211> LENGTH: 245
<212> TYPE: DNA
<213> ORGANISM: Artificial Sequence
<220> FEATURE:
<223> OTHER INFORMATION: Description of Artificial Sequence: IND-12-1

<400> SEQUENCE: 12
gctcctcttt atcatgctat ggatgttact acacaggttg gagatgattc aggaggtttc      60
tcaacaacag tttccacaga gcagaatgtt cctgatcccc aagttgggat aacaaccatg    120
agggatttaa aagggaagc caataggga agatggatg tttcaggagt gcaagcacct    180
gtgggagcta tcacaacaat tgaggatcca gttttagcaa agaaagtacc tgagacattt    240
cctga                                                                245

<210> SEQ ID NO 13
<211> LENGTH: 244
<212> TYPE: DNA
<213> ORGANISM: Artificial Sequence
<220> FEATURE:
<223> OTHER INFORMATION: Description of Artificial Sequence: IND-12-2

<400> SEQUENCE: 13
ctcctcttta tcatgctatg gatgttacca cacaggttgg agatgattca ggaggttttt      60
caacaacagt ttctacagag cagaatgttc ctgatcccca gttggcata acaaccatga    120 gggacttaaa agggaaagcc aatagggga agatggatgt ttcaggagtg caagcacctg    180
tgggagctat tacaacaatt gaggatccag ttttagcaaa gaaagtacct gagacatttc    240
ctga                                                                 244

<210> SEQ ID NO 14
<211> LENGTH: 245
<212> TYPE: DNA
<213> ORGANISM: Artificial Sequence
<220> FEATURE:
<223> OTHER INFORMATION: Description of Artificial Sequence: SCL2-10

<400> SEQUENCE: 14
tgctcctctt tatcatgcta tggatgtcac cacacaggtt ggagatgatt ccgggggttt      60
ttcaacgaca gtttctacag agcagaatgt tccagatccc caagttggta taacaactat    120
gaaggattta aaaggaaaag ccaatagagg gaaaatggat gtttcaggag tacaagcacc    180

```
tgtgggagct attacaacag ttgaggatcc agttttagca agaaaagtac ctgagacatt    240
tcctg                                                                245

<210> SEQ ID NO 15
<211> LENGTH: 245
<212> TYPE: DNA
<213> ORGANISM: Artificial Sequence
<220> FEATURE:
<223> OTHER INFORMATION: Description of Artificial Sequence: SCL3-10

<400> SEQUENCE: 15
gctcctcttt atcatgctat ggatgtcacc acacaggttg agatgattc cggaggtttt     60 tcaacgacag tttctacaga gcagaatgtt ccagatcccc aagttggtat aacaactatg   120
aaggatttaa aaggaaaagc caatagaggg aaaatggatg tttcaggagt acaagcacct   180
gtgggagcta ttacaacagt tgaggatcca gttttagcaa agaaagtacc tgagacattt   240
cctga                                                                245

<210> SEQ ID NO 16
<211> LENGTH: 245
<212> TYPE: DNA
<213> ORGANISM: Artificial Sequence
<220> FEATURE:
<223> OTHER INFORMATION: Description of Artificial Sequence: SCL4-3

<400> SEQUENCE: 16
gctcctcttt atcatgctat ggatgttacc acacaggttg agacgattc aggaggtttt     60 tcaacaacag tttctactga gcagaatgtt cctgatcccc aagttggtat aacaaccatg   120
agggacctaa aagggaaagc caatagaggg aagatggatg tttcaggagt acaagcacct   180
gtgggagcta ttacaacaat tgaggatcca gtcttggcaa agaaagtacc tgagacattt   240
cctga                                                                245

<210> SEQ ID NO 17
<211> LENGTH: 245
<212> TYPE: DNA
<213> ORGANISM: Artificial Sequence
<220> FEATURE:
<223> OTHER INFORMATION: Description of Artificial Sequence: SCL7-6

<400> SEQUENCE: 17
gctcctcttt atcatgctat ggatgtcacc acacaggttg agatgattc cggaggtttt     60 tcaacgacag tttctacaga gcagaatgtt ccagatcccc aagttggtat aacaactatg   120
aaggatttaa aaggaaaagc caatagaggg aaaatggatg tttcaggagt acaagcacct   180
gtgggagcta ttacaacagt tgaggatcca gttttagcaa agaaagtacc tgagacattt   240
cctga                                                                245

<210> SEQ ID NO 18
<211> LENGTH: 245
<212> TYPE: DNA
<213> ORGANISM: Artificial Sequence
<220> FEATURE:
<223> OTHER INFORMATION: Description of Artificial Sequence: SCL8-2

<400> SEQUENCE: 18
gctcctcttt atcatgctat ggatgtcacc acacaggttg agatgattc aggaggtttt     60 tcaacaacag tttctacaga acagaatgtt cctgatcccc aggttggcat aacaactatg   120
agggatctaa aagggaaggc caatagtgga aagatggatg tttcaggagt gcaagcacct   180
```

```
gtgggggcta ttacaacaat tgaggatcca gttttagcaa agaaagtacc tgagacattt    240
cctga                                                                245

<210> SEQ ID NO 19
<211> LENGTH: 245
<212> TYPE: DNA
<213> ORGANISM: Artificial Sequence
<220> FEATURE:
<223> OTHER INFORMATION: Description of Artificial Sequence: SCL8-5

<400> SEQUENCE: 19
gctcctcttt atcatgctat ggatgtcacc acacaggttg gagatgattc aggaggtttt     60
tcaacaacag tttctacaga gcagaatgtt cctgatcccc aggttggcat aacaactatg    120
agggatctaa aagggaaggc caatagtgga aagatggatg tttcaggagt gcaagcacct    180
gtgggggcta ttacaacaat tgaggatcca gttttagcaa agaaagtacc tgagacattt    240
cctga                                                                245

<210> SEQ ID NO 20
<211> LENGTH: 245
<212> TYPE: DNA
<213> ORGANISM: Artificial Sequence
<220> FEATURE:
<223> OTHER INFORMATION: Description of Artificial Sequence: SCL9-4

<400> SEQUENCE: 20
gctcctcttt atcatgctat ggatgttacc acacaggttg gagatgattc aggaggtttt     60
tcaacaacag tttctacaga acagaatgtt cctgatcccc aggttggcat aacaactatg    120
agggatctaa aagggaaggc caatagtgga aagatggatg tttcaggagt gcaagcacct    180
gtgggggcta ttacaacaat tgaggatcca gttttagcaa agaaagtacc tgagacattt    240
cctga                                                                245

<210> SEQ ID NO 21
<211> LENGTH: 245
<212> TYPE: DNA
<213> ORGANISM: Artificial Sequence
<220> FEATURE:
<223> OTHER INFORMATION: Description of Artificial Sequence: SCL10-1

<400> SEQUENCE: 21
gctcctcttt atcatgctat ggatgttacc acacaggttg gagatgattc aggaggtttt     60
tcaacaacag tttctacaga acagaatgtt cctgatcccc aggttggcat aacaactatg    120
agggatctaa aagggaaggc caatagtgga aagatggatg tttcaggagt gcaagcacct    180
gtgggggcta ttacaacaat tgaggatcca gttttagcaa agaaagtacc tgagacattt    240
cctga                                                                245

<210> SEQ ID NO 22
<211> LENGTH: 245
<212> TYPE: DNA
<213> ORGANISM: Artificial Sequence
<220> FEATURE:
<223> OTHER INFORMATION: Description of Artificial Sequence: SCL11-5

<400> SEQUENCE: 22
gctcctcttt atcatgctat ggatgttacc acacaggttg gagatgattc aggaggtttt     60
tcaacaacag tttctacaga acagaatgtt cctgatcccc aggttggcat aacaactatg    120
```

```
aggatctaa aagggaaggc caatagtgga aagatggatg tttcaggagt gcaagcacct      180 gtggggcta ttacaacaat tgaggatcca gttttagcaa agaaagtacc tgagacattt      240
cctga                                                                245

<210> SEQ ID NO 23
<211> LENGTH: 245
<212> TYPE: DNA
<213> ORGANISM: Artificial Sequence
<220> FEATURE:
<223> OTHER INFORMATION: Description of Artificial Sequence: SCL12-6

<400> SEQUENCE: 23
gctcctcttt atcatgctat ggatgtcacc acacaggttg gagatgattc cggaggtttt      60
tcaacgacag tttctacaga gcagaatgtt ccagatcccc aagttggtat aacaactatg     120
aaggatttaa aggaaaagc caatagaggg aaaatggatg tttcaggagt acaagcacct     180
gtgggagcta ttacaacagt tgaggatcca gttttagcaa agaaagtacc tgagacattt     240
cctga                                                                245

<210> SEQ ID NO 24
<211> LENGTH: 245
<212> TYPE: DNA
<213> ORGANISM: Artificial Sequence
<220> FEATURE:
<223> OTHER INFORMATION: Description of Artificial Sequence: SCL14-3

<400> SEQUENCE: 24
gctcctcttt atcatgctat ggatgttacc acacaggttg gagacgattc aggaggtttt      60
tcaacaacag tttctacaga gcagaatgtt cctgatcccc aagttggtat aacaaccatg     120
agggacctaa aagggaaagc caatagaggg aagatggatg tttcaggagt acaagcacct     180
gtgggagcta ttacaacaat tgaggatcca gtcttggcaa agaaagtacc tgagacattt     240
cctga                                                                245

<210> SEQ ID NO 25
<211> LENGTH: 245
<212> TYPE: DNA
<213> ORGANISM: Artificial Sequence
<220> FEATURE:
<223> OTHER INFORMATION: Description of Artificial Sequence: SCL15-1

<400> SEQUENCE: 25
gctcctcttt atcatgctat ggatgttacc acacaggttg gagacgattc aggaggtttt      60
tcaacaacag tttctacaga gcagaatgtt cctgatcccc aagttggtat aacaaccatg     120
agggacctaa aagggaaagc caatagaggg aagatggatg tttcaggagt acaagcacct     180
gtgggagcta ttacaacaat tgaggatcca gttttggcaa agaaagtacc tgagacattt     240
cctga                                                                245

<210> SEQ ID NO 26
<211> LENGTH: 245
<212> TYPE: DNA
<213> ORGANISM: Artificial Sequence
<220> FEATURE:
<223> OTHER INFORMATION: Description of Artificial Sequence: SCL15-2

<400> SEQUENCE: 26
gctcctcttt atcatgctat ggatgttacc acacaggttg gagacgattc aggaggtttt      60
tcaacaacag tttctacaga gcagaatgtt cctgatcccc aagttggtat aacaaccatg     120
```

```
agggacctaa aagggaaagc caatagaggg aagatggatg tttcaggagt acaagcacct    180
gtgggagcta ttacaacaat tgaggatcca gtcttggcaa agaaagtacc tgagacattt    240
cctga                                                                245
```

<210> SEQ ID NO 27
<211> LENGTH: 245
<212> TYPE: DNA
<213> ORGANISM: Artificial Sequence
<220> FEATURE:
<223> OTHER INFORMATION: Description of Artificial Sequence: SCL16-8

<400> SEQUENCE: 27

```
gctcctcttt atcatgctat ggatgttacc acacaggttg gagatgattc aggaggtttt     60
tcaacaacag tttctacaga acagaatgtt cctgatcccc aggttggcat aacaactatg    120
agggatctaa aagggaaggc caatagtgga aagatggatg tttcaggagt gcaagcacct    180
gtgggggcta ttacaacaat tgaggatcca gttttagcaa agaaagtacc tgagacattt    240
cctga                                                                245
```

<210> SEQ ID NO 28
<211> LENGTH: 2950
<212> TYPE: DNA
<213> ORGANISM: Artificial Sequence
<220> FEATURE:
<223> OTHER INFORMATION: Description of Artificial Sequence: HAV P1/2A
      precursor

<400> SEQUENCE: 28

```
ggtaccatga

-continued

```
ccttggattt ctgatacacc ttatcgagtg aataggtaca cgaagtcagc acatcaaaaa   1320
ggtgagtaca ctgccattgg gaagcttatt gtgtattgtt ataacagact gacttctcct   1380
tctaatgttg cttctcatgt tagagttaat gtttatcttt cagcaattaa tttggaatgt   1440
tttgctcctc tttaccatgc tatggatgtt actacacagg ttggagatga ttcaggaggt   1500
ttctcaacaa cagtttctac agagcagaat gttcctgatc cccaagttgg gataacaacc   1560
atgagggatt taaaaggaaa agccaatagg ggaaagatgg atgtttcagg agtgcaagca   1620
cctgtgggag ctatcacaac aattgaagat ccagttttag caaagaaagt acctgagaca   1680
tttcctgaat tgaagcctgg agagtccaga catacatcag atcacatgtc tatttataaa   1740
ttcatgggaa ggtctcattt tttgtgcact tttactttca attcaaataa taaagagtac   1800
acatttccaa taaccctgtc ttcgacttct aatcctcctc atggtttacc atcaacatta   1860
aggtggttct tcaatttgtt tcagttgtat agaggaccat tggatttaac aattataatc   1920
acaggagcca ctgatgtgga tggtatggcc tggtttactc cagtgggcct tgctgtcgac   1980
accccttggg tggaaaagga gtcagctttg tctattgatt ataaaactgc ccttggagct   2040
gttagattta atacaagaag aacaggaaac attcaaatta gattgccgtg gtattcttat   2100
ttgtatgccg tgtctggagc actggatggc ttgggggata agacagattc tacatttgga   2160
ttggtttcta ttcagattgc aaattacaat cattctgatg aatatttgtc cttcagttgt   2220
tatttgtctg tcacagagca atcagagttc tattttccta gagctccatt aaattcaaat   2280
gctatgttgt ccactgaatc catgatgagt agaattgcag ctggagactt ggagtcatca   2340
gtggatgatc ccagatcaga ggaggataga agatttgaga gtcatataga atgtaggaaa   2400
ccatacaaag aattgagact ggaggttggg aaacaaagac tcaaatatgc tcaggaagag   2460
ttatcaaatg aagtgcttcc acctcctagg aaaatgaagg ggttattttc acaagctaaa   2520
atttctcttt tttatactga ggagcatgaa ataatgaagt tttcttggag aggagtgact   2580
gctgatacta gggctttgag aagatttgga ttctctctgg ctgctggtag aagtgtgtgg   2640
actcttgaaa tggatgctgg agttcttact ggaagattga tcagattgaa tgatgagaaa   2700
tggacagaaa tgaaggatga taagattgtt tcattaattg aaaagttcac aagcaataaa   2760
tattggtcta aagtgaattc tccacatgga atgttggatc ttgaagaaat gctgccaatt   2820
ctaagatttt ccaaatatgt ctgagacaga tttgtgtttc ctgttacatt ggctaaatcc   2880
aaagaaaatc aatttagcag atagaatgct tggattgtct ggagtgcagg aaattaagga   2940
acaggcatgc                                                          2950
```

<210> SEQ ID NO 29
<211> LENGTH: 6696
<212> TYPE: DNA
<213> ORGANISM: Artificial Sequence
<220> FEATURE:
<223> OTHER INFORMATION: Description of Artificial Sequence: HAV open
reading frame

<400> SEQUENCE: 29

```
ggtaccatga atatgtccaa acaaggaatt ttccagactg ttgggagtgg ccttgaccac     60
atcctgtctt tggcagatat tgaggaagag caaatgattc agtccgttga taggactgca    120
gtgactggag cttcttactt cacttctgtg gaccaatctt cagttcatac tgctgaggtt    180
ggctcacatc aaattgaacc tttgaaaacc tctgttgata aacctggttc taagaaaact    240 caggggggaaa agtttttcct gattcattct gctgattggc tcactacaca tgctctcttt    300

-continued

```
catgaagttg caaaattgga tgtggtgaaa ctactgtata atgagcagtt tgccgtccaa    360
ggtttgttga gataccatac atatgcaaga tttggcattg agattcaagt tcagataaat    420
cccacaccct ttcagcaagg aggactaatt tgtgccatgg ttcctggtga ccaaagttat    480
ggttcaatag catccttgac tgtttatcct catggtctgt taaattgcaa tatcaacaat    540
gtagttagaa taaggttcc atttatttat actagaggtg cttatcattt taaagatcca     600
cagtacccag tttgggaatt gacaatcaga gtttggtcag agttgaatat tggaacagga    660
acttcagctt acacttcact caatgtttta gctaggttta cagatttgga gttgcatgga    720
ttaactcctc tttctacaca gatgatgaga atgaattta gggtcagtac tactgaaaat     780
gttgtaaatt tgtcaaatta tgaagatgca agggcaaaaa tgtcttttgc tttggatcag    840
gaagattgga agtctgatcc ttcccaaggt ggtggaatta aaattactca ttttactacc    900
tggacatcca ttccaaccct tagctgctcag tttccattta atgcttcaga ttcagttgga    960
caacaaatta agttattcc agtggaccca tactttttcc aaatgacaaa cactaatcct    1020
gatcaaaaat gtataactgc cttggcctct atttgtcaga tgttctgctt ttggagggga   1080
gatcttgttt ttgattttca ggttttttcca accaaatatc attcaggtag actgttgttt   1140
tgttttgttc ctgggaatga gttaatagat gttactggaa ttacattaaa acaggcaact   1200
actgctcctt gtgcagtgat ggacattaca ggagtgcagt caaccttgag atttcgtgtt   1260
ccttggattt ctgatacacc ttatcgagtg aataggtaca cgaagtcagc acatcaaaaa   1320
ggtgagtaca ctgccattgg gaagcttatt gtgtattgtt ataacagact gacttctcct   1380
tctaatgttg cctctcatgt tagagttaat gtttatcttt cagcaattaa tttggaatgt   1440
tttgctcctc tttaccatgc tatggatgtt actacacagg ttggagatga ttcaggaggt   1500
ttctcaacaa cagtttctac agagcagaat gttcctgatc cccaagttgg gataacaacc   1560
atgagggatt taaaggaaa agccaatagg ggaaagatgg atgtttcagg agtgcaagca   1620
cctcgtggga gctatcagca acaattgaac gatccagttt tagcaaagaa agtacctgag   1680
acatttcctg aattgaagcc tggagagtcc agacatacat cagatcacat gtctattat    1740
aaattcatgg gaaggtctca tttttttgtgc acttttactt tcaattcaaa taataaagag   1800
tacacatttc caataaccct gtcttcgact tctaatcctc ctcatggttt accatcaaca   1860
ttaaggtggt tcttcaattt gtttcagttg tatagaggac cattggattt aacaattata   1920
atcacaggag ccactgatgt ggatggtatg gcctggttta ctccagtggg ccttgctgtc   1980
gacccttggg tggaaaagga gtcagctttg tctattgatt ataaaactgc ccttggagct   2040
gttagattta atacaagaag aacaggaaac attcaaatta gattgccgtg gtattcttat   2100
ttgtatgccg tgtctggagc actggatggc ttggggggata agacagattc tacatttgga   2160
ttgtttctat tcgagattgc aaattacaat cattctgatg aatatttgtc cttcagttgt   2220
tatttgtctg tcacagagca atcagagttc tattttcctta gagctccatt aaattcaaat   2280
gctatgttgt ccactgaatc catgatgagt agaattgcag ctggagactt ggagtcatca   2340
gtggatgatc ccagatcaga ggaggataga agatttgaga gtcatataga atgtaggaaa   2400
ccatacaaag aattgagact ggaggttggg aaacaaagac tcaaatatgc tcaggaagag   2460
ttatcaaatg aagtgcttcc acctcctagg aaaatgaagg ggttatttc acaagctaaa   2520
atttctcttt tttatactga ggagcatgaa ataatgaagt ttcttggag aggagtgact   2580
gctgatacta gggctttgag aagatttgga ttctctctgg ctgctggtag aagtgtgtgg   2640
```

```
actcttgaaa tggatgctgg agttcttact ggaagattga tcagattgaa tgatgagaaa      2700
tggacagaaa tgaaggatga taagattgtt tcattaattg aaaagttcac aagcaataaa      2760
tattggtcta aagtgaattt tccacatgga atgttggatc ttgaagaaat tgctgccaat      2820
tctaaggatt ttccaaatat gtctgagaca gatttgtgtt tcctgttaca ttggctaaat      2880
ccaaagaaaa tcaatttagc agatagaatg cttggattgt ctggagtgca ggaaattaag      2940
gaacagggtg ttggactgat agcagagtgt agaactttct tggattctat tgctgggact      3000
ttgaaatcta tgatgtttgg gtttcatcat tctgtgactg ttgaaattat aaatactgtg      3060
ctttgttttg ttaagagtgg aatcctgctt tatgtcatac aacaattgaa ccaagatgaa      3120
cactctcaca taattggttt gttgagagtt atgaattatg cagatattgg ctgttcagtt      3180
atttcatgtg gtaaagtttt ttccaaaatg ttagaaacag tttttaattg gcaaatggat      3240
tctagaatga tggagctgag gactcagagc ttctctaatt ggttaagaga tatttgttca      3300
ggaattacta ttttttaaaag ttttaaggat gccatatatt ggttatatac aaaattgaag      3360
gatttttatg aagtaaatta tggcaagaaa aaggatattc ttaatattct caaagataat      3420
cagcaaaaaa tagaaaaagc cattgaagaa gcagacaatt tttgcatttt gcaaattcaa      3480
gatgtagaga aatttgatca gtatcagaaa ggggttgatt taatacaaaa gctgagaact      3540
gtccattcaa tggcgcaagt tgaccccaat ttggggttc atttgtcacc tctcagagat      3600
tgcatagcaa gagtccacca aaagctcaag aatcttggat ctataaatca ggccatggta      3660
acaagatgtg agccagttgt ttgctatttg tatggcaaaa gagggggagg gaaaagcttg      3720
acttcaattg cattggcaac caaaatttgt aaacactatg gtgttgaacc tgagaaaaat      3780
atttacacca aacctgtggc ctcagattat tgggatggat atagtggaca attagtttgc      3840
attattgatg atattggcca aaacacaaca gatgaagatt ggtcagattt ttgtcaatta      3900
gtgtcaggat gcccaatgag attgaatatg gcttctctag aggagaaggg cagacatttt      3960
tcctctcctt ttataatagc aacttcaaat tggtcaaatc caagtccaaa aacagtttat      4020
gttaaggaag caattgatcg taggcttcat tttaaggttg aagttaaacc tgcttcattt      4080
tttaaaaatc ctcacaatga tatgttgaat gttaatttgg ccaaaacaaa tgatgcaatt      4140
aaggacatgt cttgtgttga tttaataatg gatggacaca atatttcatt gatggattta      4200
cttagttcct tagtgatgac agttgaaatt aggaaacaga atatgagtga attcatggag      4260
ttgtggtctc agggaatttc agatgatgac aatgatagtg cagtggctga gttttttccag      4320 tcttttccat ctggtgaacc atcaaattgg aagttatcta gttttttcca atctgtcact      4380
aatcacaagt gggttgctgt gggagctgca gttggcattc ttgagtgct tgtgggagga      4440 tggtttgtgt ataagcattt ttcccgcaaa gaggaagaac caattccagc tgaagggggtt     4500 tatcatggcg tgactaagcc caaacaagtg attaaattgg atgcagatcc agtagagtcc      4560
cagtcaactc tagaaatagc aggattagtt aggaaaaaatc tggttcagtt tggagttggt     4620
gagaaaaatg gatgtgtgag atgggtcatg aatgccttag gagtgaagga tgattggttg      4680
ttagtacctt ctcatgctta taaatttgaa aaggattatg aaatgatgga gttttacttc      4740
aatagaggtg gaacttacta ttcaatttca gctggtaatg ttgttattca atctttagat      4800
gtgggatttc aagatgttgt tttaatgaag gtttctacaa ttcccaagtt tagagatatt      4860
actcaacact ttattaagaa aggagatgtg cctagagcct taaatcgctt ggcaacatta      4920
gtgacaaccg ttaatggaac tcctatgtta atttctgagg gaccattaaa gatggaagaa      4980
aaagccactt atgttcataa gaagaatgat ggtactacag ttgatttgac tgtagatcag      5040
```

-continued

```
gcatggagag gaaaaggtga aggtcttcct ggaatgtgtg gtggggccct agtgtcatca      5100
aatcagtcca tacagaatgc aattttgggt attcatgttg ctggaggaaa ttcaattctt      5160
gtggcaaagc tggttactca agaaatgttt caaaacattg ataagaaaat tgaaagtcag      5220
agaataatga aagtggaatt tactcaatgt tcaatgaatg tagtctccaa aacgcttttt      5280
agaaagagtc ccattcatca ccacattgat agaaccatga ttaattttcc tgcagctatg      5340
cctttctcta aagctgaaat tgatccaatg gctatgatgt tgtccaaata ttcattacct      5400
attgtggagg aaccagagga ttacaaggaa gcttcagttt tttatcaaaa caaaatagta      5460
ggcaagactc agctagttga tgactttta gatcttgata tggctattac aggggctcca      5520
ggcattgatg ctatcaatat ggattcatct cctgggtttc cttatgttca agaaaaattg      5580
accaaaagag atttaattg gttggatgaa atggtttgc tgttaggagt tcacccaaga      5640
ttggcccaga gaatttttatt taatactgtc atgatggaaa attgttctga cttagatgtt      5700 gttttttacaa cttgtccaaa agatgaattg agaccattag aaaaagtttt ggaatcaaaa      5760
acaagagcca ttgatgcttg tcctttggat tatacaattc tatgtcgaat gtattggggt      5820
ccagctatca gttatttcca tttgaatcca gggtttcaca caggtgttgc tattggcata      5880
gatcctgata gacagtggga tgaattattt aaaacaatga taagatttgg agatgttggt      5940
cttgatttag atttctctgc ttttgatgcc agtcttagtc catttatgat tagggaagca      6000
ggtagaatca tgagtgaatt atctggaaca ccatctcatt ttggaacagc tcttatcaat      6060
actatcattt attctaaaca tctgctgtac aactgttgtt atcatgtttg tggttcaatg      6120 ccttctggt ctccttgcac agctttgttg aattcaatta ttaataatat taatctgtat      6180
tatgtgtttt ctaaaatatt tggaaagtct ccagttttct tttgtcaagc tttgaggatc      6240
ctttgttacg gagatgatgt tttgatagtt ttttccagag atgttcaaat tgacaatctt      6300
gacttgattg gacagaaaat tgtagatgag ttcaaaaaac ttggcatgac agccacctca      6360
gctgataaaa atgtgcctca actgaagcca gtttcagaat tgactttct caaaagatct      6420 ttcaatttgg tggaggatag aattagacct gcaatttcag aaaagacaat tggtctttg      6480 atggcttggc agagaagtaa cgctgagttt gagcggaatt tagaaaatgc tcagtggttt      6540 gctttttatgc atggctatga gttctatcag aaattttatt attttgttca gtcctgtttg      6600
gagaaagaga tgatagaata tagacttaaa tcttatgatt ggtggagaat gagatttttat      6660 gaccagtgtt tcatttgtga cctttcatga gcatgc                                6696
```

<210> SEQ ID NO 30
<211> LENGTH: 6757
<212> TYPE: DNA
<213> ORGANISM: Artificial Sequence
<220> FEATURE:
<223> OTHER INFORMATION: Description of Artificial Sequence: HAV open
      reading frame plus additional 3' untranslated sequences

<400> SEQUENCE: 30

```
ggtaccatga atatgtccaa acaaggaatt ttccagactg ttgggagtgg ccttgaccac        60
atcctgtctt tggcagatat tgaggaagag caaatgattc agtccgttga taggactgca       120
gtgactggag cttcttactt cacttctgtg gaccaatctt cagttcatac tgctgaggtt       180
ggctcacatc aaattgaacc tttgaaaacc tctgttgata aacctggttc taagaaaact       240 caggggaaa agttttttcct gattcattct gctgattggc tcactacaca tgctctcttt       300
catgaagttg caaaattgga tgtggtgaaa ctactgtata atgagcagtt tgccgtccaa       360
```

```
ggtttgttga gataccatac atatgcaaga tttggcattg agattcaagt tcagataaat    420
cccacaccct ttcagcaagg aggactaatt tgtgccatgg ttcctggtga ccaaagttat    480
ggttcaatag catccttgac tgtttatcct catggtctgt taaattgcaa tatcaacaat    540
gtagttagaa taaaggttcc atttatttat actagaggtg cttatcattt taaagatcca    600
cagtacccag tttgggaatt gacaatcaga gtttggtcag agttgaatat tggaacagga    660
acttcagctt acacttcact caatgttttα gctaggttta cagatttgga gttgcatgga    720
ttaactcctc tttctacaca gatgatgaga atgaattta gggtcagtac tactgaaaat     780
gttgtaaatt tgtcaaatta tgaagatgca agggcaaaaa tgtcttttgc tttggatcag    840
gaagattgga agtctgatcc ttcccaaggt ggtggaatta aaattactca ttttactacc    900
tggacatcca ttccaacctt agctgctcag tttccattta atgcttcaga ttcagttgga    960
caacaaatta aagttattcc agtggaccca tactttttcc aaatgacaaa cactaatcct   1020
gatcaaaaat gtataactgc cttggcctct atttgtcaga tgttctgctt ttggagggga   1080
gatcttgttt ttgattttca ggttttcca accaaatatc attcaggtag actgttgttt   1140
tgttttgttc ctgggaatga gttaatagat gttactggaa ttacattaaa acaggcaact   1200
actgctcctt gtgcagtgat ggacattaca ggagtgcagt caaccttgag atttcgtgtt   1260 ccttggatt ctgatacacc ttatcgagtg aataggtaca cgaagtcagc acatcaaaaa   1320
ggtgagtaca ctgccattgg gaagcttatt gtgtattgtt ataacagact gacttctcct   1380
tctaatgttg cctctcatgt tagagttaat gtttatcttt cagcaattaa tttggaatgt   1440
tttgctcctc tttaccatgc tatggatgtt actacacagg ttggagatga ttcaggaggt   1500
ttctcaacaa cagtttctac agagcagaat gttcctgatc cccaagttgg gataacaacc   1560
atgagggatt taaaggaaa agccaatagg ggaaagatgg atgtttcagg agtgcaagca   1620
cctcgtggga gctatcagca acaattgaac gatccagttt tagcaaagaa agtacctgag   1680
acatttcctg aattgaagcc tggagagtcc agacatacat cagatcacat gtctatttat   1740
aaattcatgg gaaggtctca tttttttgtgc acttttactt tcaattcaaa taataaagag   1800
tacacatttc caataaccct gtcttcgact tctaatcctc ctcatggttt accatcaaca   1860
ttaaggtggt tcttcaattt gttcagttg tatagaggac cattggattt aacaattata   1920
atcacaggag ccactgatgt ggatggtatg gcctggttta ctccagtggg ccttgctgtc   1980 gaccctttggg tggaaaagga gtcagctttg tctattgatt ataaaactgc ccttggagct   2040
gttagattta atacaagaag aacaggaaac attcaaatta gattgccgtg gtattcttat   2100
ttgtatgccg tgtctggagc actggatggc ttgggggata agacagattc tacatttgga   2160 ttgttttctat tcgagattgc aaattacaat cattctgatg aatatttgtc cttcagttgt   2220
tatttgtctg tcacagagca atcagagttc tattttccta gagctccatt aaattcaaat   2280
gctatgttgt ccactgaatc catgatgagt agaattgcag ctggagactt ggagtcatca   2340
gtggatgatc ccagatcaga ggaggataga agatttgaga gtcatataga atgtaggaaa   2400
ccatacaaag aattgagact ggaggttggg aaacaaagac tcaaatatgc tcaggaagag   2460
ttatcaaatg aagtgcttcc acctcctagg aaaatgaagg ggttatttc acaagctaaa   2520 atttctcttt tttatactga ggagcatgaa ataatgaagt tttcttggag aggagtgact   2580
gctgatacta gggctttgag aagatttgga ttctctctgg ctgctggtag aagtgtgtgg   2640
actcttgaaa tggatgctgg agttcttact ggaagattga tcagattgaa tgatgagaaa   2700
```

```
tggacagaaa tgaaggatga taagattgtt tcattaattg aaaagttcac aagcaataaa    2760
tattggtcta aagtgaattt tccacatgga atgttggatc ttgaagaaat tgctgccaat    2820
tctaaggatt ttccaaatat gtctgagaca gatttgtgtt tcctgttaca ttggctaaat    2880
ccaaagaaaa tcaatttagc agatagaatg cttggattgt ctggagtgca ggaaattaag    2940
gaacagggtg ttggactgat agcagagtgt agaactttct tggattctat tgctgggact    3000
ttgaaatcta tgatgtttgg gtttcatcat tctgtgactg ttgaaattat aaatactgtg    3060
ctttgttttg ttaagagtgg aatcctgctt tatgtcatac aacaattgaa ccaagatgaa    3120
cactctcaca taattggttt gttgagagtt atgaattatg cagatattgg ctgttcagtt    3180
atttcatgtg gtaaagtttt ttccaaaatg ttagaaacag ttttttaattg gcaaatggat    3240 tctagaatga tggagctgag gactcagagc ttctctaatt ggttaagaga tatttgttca    3300
ggaattacta ttttttaaaag ttttaaggat gccatatatt ggttatatac aaaattgaag    3360
gatttttatg aagtaaatta tggcaagaaa aaggatattc ttaatattct caaagataat    3420
cagcaaaaaa tagaaaaagc cattgaagaa gcagacaatt tttgcatttt gcaaattcaa    3480
gatgtagaga aatttgatca gtatcagaaa ggggttgatt taatacaaaa gctgagaact    3540
gtccattcaa tggcgcaagt tgaccccaat ttgggggttc atttgtcacc tctcagagat    3600
tgcatagcaa gagtccacca aaagctcaag aatcttggat ctataaatca ggccatggta    3660
acaagatgtg agccagttgt ttgctatttg tatggcaaaa gagggggagg gaaaagcttg    3720
acttcaattg cattggcaac caaaatttgt aaacactatg gtgttgaacc tgagaaaaat    3780
atttacacca aacctgtggc ctcagattat tgggatggat atagtggaca attagtttgc    3840
attattgatg atattggcca aaacacaaca gatgaagatt ggtcagattt ttgtcaatta    3900
gtgtcaggat gcccaatgag attgaatatg gcttctctag aggagaaggg cagacatttt    3960
tcctctcctt ttataatagc aacttcaaat tggtcaaatc caagtccaaa acagtttat    4020 gttaaggaag caattgatcg taggcttcat tttaaggttg aagttaaacc tgcttcattt    4080
tttaaaaatc ctcacaatga tatgttgaat gttaatttgg ccaaaacaaa tgatgcaatt    4140
aaggacatgt cttgtgttga tttaataatg gatggacaca atatttcatt gatggattta    4200
cttagttcct tagtgatgac agttgaaatt aggaaacaga atatgagtga attcatggag    4260
ttgtggtctc agggaatttc agatgatgac aatgatagtg cagtggctga gtttttccag    4320
tcttttccat ctggtgaacc atcaaattgg aagttatcta gttttttcca atctgtcact    4380
aatcacaagt gggttgctgt gggagctgca gttggcattc ttgagtgct tgtgggagga    4440 tggtttgtgt ataagcattt tcccgcaaaa gaggaagaac caattccagc tgaagggggtt    4500 tatcatggcg tgactaagcc caaacaagtg attaaattgg atgcagatcc agtagagtcc    4560
cagtcaactc tagaaatagc aggattagtt aggaaaaatc tggttcagtt tggagttggt    4620
gagaaaaatg gatgtgtgag atgggtcatg aatgccttag gagtgaagga tgattggttg    4680
ttagtacctt ctcatgctta taaatttgaa aaggattatg aaatgatgga gttttacttc    4740
aatagaggtg gaacttacta ttcaatttca gctggtaatg ttgttattca atctttagat    4800
gtgggatttc aagatgttgt tttaatgaag gtttctacaa ttcccaagtt tagagatatt    4860
actcaacact ttattaagaa aggagatgtg cctagagcct taaatcgctt ggcaacatta    4920
gtgacaaccg ttaatggaac tcctatgtta atttctgagg gaccattaaa gatggaagaa    4980
aaagccactt atgttcataa gaagaatgat ggtactacag ttgatttgac tgtagatcag    5040
gcatggagag gaaaaggtga aggtcttcct ggaatgtgtg gtgggccct agtgtcatca    5100
```

-continued

```
aatcagtcca tacagaatgc aattttgggt attcatgttg ctggaggaaa ttcaattctt    5160
gtggcaaagc tggttactca agaaatgttt caaaacattg ataagaaaat tgaaagtcag    5220
agaataatga aagtggaatt tactcaatgt tcatgaatg tagtctccaa aacgcttttt    5280
agaaagagtc ccattcatca ccacattgat agaaccatga ttaatttttcc tgcagctatg    5340 cctttctcta aagctgaaat tgatccaatg gctatgatgt tgtccaaata ttcattacct    5400
attgtggagg aaccagagga ttacaaggaa gcttcagttt tttatcaaaa caaaatagta    5460
ggcaagactc agctagttga tgactttttta gatcttgata tggctattac agggctcca    5520 ggcattgatg ctatcaatat ggattcatct cctgggtttc cttatgttca agaaaaattg    5580
accaaaagag atttaatttg gttggatgaa atggtttgc tgttaggagt tcacccaaga    5640
ttggcccaga gaattttatt taatactgtc atgatggaaa attgttctga cttagatgtt    5700 gttttttacaa cttgtccaaa agatgaattg agaccattag aaaaagtttt ggaatcaaaa    5760
acaagagcca ttgatgcttg tcctttggat tatacaattc tatgtcgaat gtattgggt    5820 ccagctatca gttatttcca tttgaatcca gggtttcaca caggtgttgc tattggcata    5880
gatcctgata gacagtggga tgaattattt aaaacaatga taagatttgg agatgttggt    5940
cttgatttag atttctctgc ttttgatgcc agtcttagtc catttatgat tagggaagca    6000
ggtagaatca tgagtgaatt atctggaaca ccatctcatt ttggaacagc tcttatcaat    6060
actatcattt attctaaaca tctgctgtac aactgttgtt atcatgttg tggttcaatg    6120 ccttctgggt ctccttgcac agctttgttg aattcaatta ttaataatat taatctgtat    6180
tatgtgtttt ctaaaatatt tggaaagtct ccagttttct tttgtcaagc tttgaggatc    6240 cttttgttacg gagatgatgt tttgatagtt tttttccagag atgttcaaat tgacaatctt    6300
gacttgattg gacagaaaat tgtagatgag ttcaaaaaac ttggcatgac agccaccctca    6360 gctgataaaa atgtgcctca actgaagcca gtttcagaat tgacttttct caaaagatct    6420
ttcaatttgg tggaggatag aattagacct gcaatttcag aaaagacaat ttggtctttg    6480
atggcttggc agagaagtaa cgctgagttt gagcagaatt tagaaaatgc tcagtggttt    6540
gcttttatgc atggctatga gttctatcag aaatttttatt attttgttca gtcctgtttg    6600
gagaaagaga tgatagaata tagacttaaa tcttatgatt ggtggagaat gagatttat    6660 gaccagtgtt tcatttgtga cctttcatga tttgtttaaa caaattttct tactctttct    6720
gaggtttgtt tatttctttt gtccgctaac tgcatgc                             6757
```

<210> SEQ ID NO 31
<211> LENGTH: 2508
<212> TYPE: DNA
<213> ORGANISM: Artificial Sequence
<220> FEATURE:
<223> OTHER INFORMATION: Description of Artificial Sequence: recombinant protein of 94 kDa

<400> SEQUENCE: 31

```
atgaatatgt ccaaacaagg aatttttccgg actgttggga gtggccttga ccacatcctg     60
tctttggcag atattgagga agagcaaatg attcagtccg ttgataggac tgcagtgact    120
ggagcttctt acttcacttc tgtggaccaa tcttcagttc atactgctga ggttggctca    180
catcaaattg aacctttgaa aacctctgtt gataaacctg gttctaagaa aactcagggg    240
gaaaagtttt tcctgattca ttctgctgat tggctcacta cacatgctct ctttcatgaa    300
gttgcaaaat tggatgtggt gaaactactg tataatgagc agtttgccgt ccaaggtttg    360
```

```
ttgagatacc atacatatgc aagatttggc attgagattc aagttcagat aaatcccaca      420 cccctttcagc aaggaggact aatttgtgcc atggttcctg gtgaccaaag ttatggttca      480
atagcatcct tgactgttta tcctcatggt ctgttaaatt gcaatatcaa caatgtagtt      540
agaataaagg ttccatttat ttatactaga ggtgcttatc attttaaaga tccacagtac      600
ccagtttggg aattgacaat cagagtttgg tcagagttga atattggaac aggaacttca      660
gcttacactt cactcaatgt tttagctagg tttacagatt ggagttgca tggattaact       720 cctctttcta cacagatgat gagaaatgaa tttagggtca gtactactga aaatgttgta      780
aatttgtcaa attatgaaga tgcaagggca aaaatgtctt ttgctttgga tcaggaagat      840
tggaagtctg atccttccca aggtggtgga attaaaatta ctcattttac tacctggaca      900
tccattccaa ccttagctgc tcagtttcca tttaatgctt cagattcagt tggacaacaa      960
attaaagtta ttccagtgga cccatacttt ttccaaatga caaacactaa tcctgatcaa     1020
aaatgtataa ctgccttggc tctatttgt cagatgttct gcttttggag gggagatctt      1080 gttttgatt ttcaggtttt tccaaccaaa tatcattcag gtagactgtt gttttgtttt      1140
gttcctggga atgagttaat agatgttact ggaattacat aaaacaggc aactactgct      1200 ccttgtgcag tgatggacat tacaggagtg cagtcaacct tgagatttcg tgttccttgg      1260
atttctgata caccttatcg agtgaatagg tacacgaagt cagcacatca aaaaggtgag      1320
tacactgcca ttgggaagct tattgtgtat tgttataaca gactgacttc tccttctaat      1380
gttgcctctc atgttagagt taatgtttat cttcagcaa ttaatttgga atgttttgct      1440
cctctttacc atgctatgga tgttactaca caggttggag atgattcagg aggtttctca      1500
acaacagttt ctacagagca gaatgttcct gatccccaag ttgggataac aaccatgagg      1560
gattcaaaag gaaaagccaa taggggaaag atggatgttt caggagtgca agcacctgtg      1620
ggagctatca caacaattga agatccagtt ttagcaaaga aagtacctga gacatttcct      1680
gaattgaagc ctggagagtc cagacataca tcagatcaca tgtctattta taaattcatg      1740
ggaaggtctc atttttgtg cacttttact ttcaattcaa ataataaaga gtacacattt      1800
ccaataaccc tgtcttcgac ttctaatcct cctcatggtt taccatcaac attaaggtgg      1860
ttcttcaatt tgtttcagtt gtatagagga ccattggatt taacaattat aatcacagga      1920
gccactgatg tggatggtat ggcctggttt actccagtgg gccttgctgt cgacacccct      1980
tgggtggaaa aggagtcagc tttgtctatt gattataaaa ctgcccttgg agctgttaga      2040
tttaatacaa gaagaacagg aatcatccaa attagattgc cgtggtattc ttatttgtat      2100
gccgtgtctg gagcactgga tggcttgggg gataagacag attctacatt tggattggtt      2160
tctattcaga ttgcaaatta caatcattct gatgaatatt tgtccttcag ttgttatttg      2220
tctgtcacag agcaatcaga gttctatttt cctagagctc cattaaattc aaatgctatg      2280
ttgtccactg aatccatgat gagtagaatt gcagctggag acttggagtc atcagtggat      2340
gatcccagat cagaggagga tagaagattt gagagtcata tagaatgtag gaaaccatac      2400
aaagaattga gactggaggt tgggaaacaa agactcaaat atgctcagga agagttatca      2460
aatgaagtgc ttccacctcc taggaaaatc aagggggttat tttcacaa                  2508
```

<210> SEQ ID NO 32
<211> LENGTH: 2940
<212> TYPE: DNA
<213> ORGANISM: Artificial Sequence
<220> FEATURE:

<223> OTHER INFORMATION: Description of Artificial Sequence: recombinant
      protein of 115.5 kDa

<400> SEQUENCE: 32

| | | | | | |
|---|---|---|---|---|---|
| atgaatatgt | ccaaacaagg | aattttccag | actgttggga | gtggccttga | ccacatcctg | 60 |
| tctttggcag | atattgagga | agagcaaatg | attcagtccg | ttgataggac | tgcagtgact | 120 |
| ggagcttctt | acttcacttc | tgtggaccaa | tcttcagttc | atactgctga | ggttggctca | 180 |
| catcaaattg | aacctttgaa | aacctctgtt | gataaacctg | gttctaagaa | aactcagggg | 240 |
| gaaaagtttt | tcctgattca | ttctgctgat | tggctcacta | cacatgctct | ctttcatgaa | 300 |
| gttgcaaaat | tggatgtggt | gaaactactg | tataatgagc | agtttgccgt | ccaaggtttg | 360 |
| ttgagatacc | atacatatgc | aagatttggc | attgagattc | aagttcagat | aaatcccaca | 420 |
| ccctttcagc | aaggaggact | aatttgtgcc | atggttcctg | gtgaccaaag | ttatggttca | 480 |
| atagcatcct | tgactgttta | tcctcatggt | ctgttaaatt | gcaatatcaa | caatgtagtt | 540 |
| agaataaagg | ttccatttat | ttatactaga | ggtgcttatc | attttaaaga | tccacagtac | 600 |
| ccagtttggg | aattgacaat | cagagtttgg | tcagagttga | atattggaac | aggaacttca | 660 |
| gcttacactt | cactcaatgt | tttagctagg | tttacagatt | tggagttgca | tggattaact | 720 |
| cctctttcta | cacagatgat | gagaaatgaa | tttagggtca | gtactactga | aaatgttgta | 780 |
| aatttgtcaa | attatgaaga | tgcaagggca | aaaatgtctt | ttgctttgga | tcaggaagat | 840 |
| tggaagtctg | atccttccca | aggtggtgga | attaaaatta | ctcattttac | tacctggaca | 900 |
| tccattccaa | ccttagctgc | tcagtttcca | tttaatgctt | cagattcagt | tggacaacaa | 960 |
| attaaagtta | ttccagtgga | cccatacttt | tccaaatga | caaacactaa | tcctgatcaa | 1020 |
| aaatgtataa | ctgccttggc | ctctatttgt | cagatgttct | gcttttggag | gggagatctt | 1080 |
| gtttttgatt | tcaggttttt | tccaaccaaa | tatcattcag | gtagactgtt | gttttgtttt | 1140 |
| gttcctggga | atgagttaat | agatgttact | ggaattacat | taaaacaggc | aactactgct | 1200 |
| ccttgtgcag | tgatggacat | tacaggagtg | cagtcaacct | tgagatttcg | tgttccttgg | 1260 |
| atttctgata | caccttatcg | agtgaatagg | tacacgaagt | cagcacatca | aaaaggtgag | 1320 |
| tacactgcca | ttgggaagct | tattgtgtat | tgttataaca | gactgacttc | tccttctaat | 1380 |
| gttgcctctc | atgttagagt | taatgtttat | ctttcagcaa | ttaatttgga | atgttttgct | 1440 |
| cctctttacc | atgctatgga | tgttactaca | caggttggag | atgattcagg | aggtttctca | 1500 |
| acaacagttt | ctacagagca | gaatgttcct | gatccccaag | ttgggataac | aaccatgagg | 1560 |
| gatttaaaag | gaaaagccaa | taggggaaag | atggatgttt | caggagtgca | agcacctgtg | 1620 |
| ggagctatca | caacaattga | agatccagtt | ttagcaaaga | aagtacctga | gacatttcct | 1680 |
| gaattgaagc | ctggagagtc | cagacataca | tcagatcaca | tgtctatttta | taaattcatg | 1740 |
| ggaaggtctc | attttttgtg | cacttttact | ttcaattcaa | ataataaaga | gtacacattt | 1800 |
| ccaataaccc | tgtcttcgac | ttctaatcct | cctcatggtt | taccatcaac | attaaggtgg | 1860 |
| ttcttcaatt | tgtttcagtt | gtatagagga | ccattggatt | taacaattat | aatcacagga | 1920 |
| gccactgatg | tggatggtat | ggcctggttt | actccagtgg | gccttgctgt | cgacacccct | 1980 |
| tgggtggaaa | aggagtcagc | tttgtctatt | gattataaaa | ctgcccttgg | agctgttaga | 2040 |
| tttaatacaa | gaagaacagg | aaacattcaa | attagattgc | cgtggtattc | ttatttgtat | 2100 |
| gccgtgtctg | gagcactgga | tggcttgggg | gataagacag | attctacatt | tggattggtt | 2160 |
| tctattcaga | ttgcaaatta | caatcattct | gatgaatatt | tgtccttcag | ttgttatttg | 2220 |

| | |
|---|---|
| tctgtcacag agcaatcaga gttctatttt cctagagctc cattaaattc aaatgctatg | 2280 |
| ttgtccactg aatccatgat gagtagaatt gcagctggag acttggagtc atcagtggat | 2340 |
| gatcccagat cagaggagga tagaagattt gagagtcata tagaatgtag gaaaccatac | 2400 |
| aaagaattga gactggaggt tgggaaacaa agactcaaat atgctcagga agagttatca | 2460 |
| aatgaagtgc ttccacctcc taggaaaatg aaaggcctat tttcacaagc taaaatttct | 2520 |
| cttttttata ctgaggagca tgaaataatg aagtttctt ggagaggagt gactgctgat | 2580 |
| actagggctt tgagaagatt tggattctct ctggctgctg gtagaagtgt gtggactctt | 2640 |
| gaaatggatg ctggagttct tactggagga ttgatcagat tgaatgatga gaaatggaca | 2700 |
| gaaatgaagg atgataagat tgtttcatta attgaaaagt tcacaagcaa taaatattgg | 2760 |
| tctaaagtga attttccgca tgcaatgttg gatcttgaag aaattgctgc caattcgaag | 2820 |
| gattttccaa atatgtctga gacagatttg tgtttcctgt tacattggct aaatccaaag | 2880 |
| aaaatcaatt tagcagatag aatgcttgga ttgtctggag tgcaggaaat taaggaacag | 2940 |

<210> SEQ ID NO 33
<211> LENGTH: 669
<212> TYPE: DNA
<213> ORGANISM: Artificial Sequence
<220> FEATURE:
<223> OTHER INFORMATION: Description of Artificial Sequence: recombinant
      protein of 25 kDa

<400> SEQUENCE: 33

| | |
|---|---|
| atggatattg aggaagagca aatgattcag tccgttgata ggactgcagt gactggagct | 60 |
| tcttacttca cttctgtgga ccaatcttca gttcatactg ctgaggttgg ctcacatcaa | 120 |
| attgaacctt tgaaaacctc tgttgataaa cctggttcta gaaaactca gggggaaaag | 180 |
| ttttcctga ttcattctgc tgattggctc actacacatg ctctctttca tgaagttgca | 240 |
| aaattggatg tggtgaaact actgtataat gagcagtttg ccgtccaagg tttgttgaga | 300 |
| taccatacat atgcaagatt tggcattgag attcaagttc agataaatcc cacacccttt | 360 |
| cagcaaggag gactaatttg tgccatggtt cctggtgacc aaagtatgg ttcaatagca | 420 |
| tccttgactg tttatcctca tggtctgtta aattgcaata tcaacaatgt agttagaata | 480 |
| aaggttccat ttatttatac tagaggtgct tatcatttta aagatccaca gtacccagtt | 540 |
| tgggaattga caatcagagt ttggtcagag ttgaatattg gaacaggaac ttcagcttac | 600 |
| acttcactca atgttttagc taggtttaca gatttggagt tgcatggatt aactcctctt | 660 |
| tctacacag | 669 |

<210> SEQ ID NO 34
<211> LENGTH: 744
<212> TYPE: DNA
<213> ORGANISM: Artificial Sequence
<220> FEATURE:
<223> OTHER INFORMATION: Description of Artificial Sequence: recombinant
      protein of 28 kDa

<400> SEQUENCE: 34

| | |
|---|---|
| atggctatga tgagaaatga atttagggtc agtactactg aaaatgttgt aaatttgtca | 60 |
| aattatgaag atgcaagggc aaaaatgtct tttgctttgg atcaggaaga ttggaagtct | 120 |
| gatccttccc aagtggtgg aattaaaatt actcatttta ctacctggac atccattcca | 180 |
| accttagctg ctcagtttcc atttaatgct tcagattcag ttggacaaca aattaaagtt | 240 |
| attccagtgg acccatactt tttccaaatg acaaacacta atcctgatca aaaatgtata | 300 |

-continued

```
actgccttgg cctctatttg tcagatgttc tgcttttgga ggggagatct tgttttgat      360 tttcaggttt ttccaaccaa atatcattca ggtagactgt tgttttgttt tgttcctggg    420
aatgagttaa tagatgttac tggaattaca ttaaaacagg caactactgc tccttgtgca    480
gtgatggaca ttacaggagt gcagtcaacc ttgagatttc gtgttccttg gatttctgat    540
acaccttatc gagtgaatag gtacacgaag tcagcacatc aaaaaggtga gtacactgcc    600
attgggaagc ttattgtgta ttgttataac agactgactt ctccttctaa tgttgcctct    660
catgttagag ttaatgttta tctttcagca attaatttgg aatgttttgc tcctctttac    720
catgctatgg atgttactac acag                                            744
```

<210> SEQ ID NO 35
<211> LENGTH: 906
<212> TYPE: DNA
<213> ORGANISM: Artificial Sequence
<220> FEATURE:
<223> OTHER INFORMATION: Description of Artificial Sequence: recombinant
      protein of 33.3 kDa

<400> SEQUENCE: 35

```
atggctgttg agatgattc aggaggtttc tcaacaacag tttctacaga gcagaatgtt      60
cctgatcccc aagttgggat aacaaccatg agggattcaa aaggaaaagc caataggga     120 aagatggatg tttcaggagt gcaagcacct gtgggagcta tcacaacaat tgaagatcca    180
gttttagcaa agaaagtacc tgagacattt cctgaattga agcctggaga gtccagacat    240
acatcagatc acatgtctat ttataaattc atgggaaggt ctcatttttt gtgcactttt    300
actttcaatt caaataataa agagtacaca tttccaataa ccctgtcttc gacttctaat    360
cctcctcatg gtttaccatc aacattaagg tggttcttca atttgtttca gttgtataga    420
ggaccattgg atttaacaat tataatcaca ggagccactg atgtggatgg tatggcctgg    480
tttactccag tgggccttgc tgtcgacacc ccttgggtgg aaaaggagtc agctttgtct    540
attgattata aaactgccct tggagctgtt agatttaata caagaagaac aggaaacatc    600
caaattagat tgccgtggta ttcttatttg tatgccgtgt ctggagcact ggatggcttg    660
gggggtaaga cagattctac atttggattg gtttctattc agattgcaaa ttacaatcat    720
tctgatgaat atttgtcctt cagttgttat tgtctgtca cagagcaatc agagttctat    780
tttcctagag ctccattaaa ttcaaatgct atgttgtcca ctgaatccat gatgagtaga    840
attgcagctg gagacttgga gtcatcagtg gatgatccca gatcagagga ggatagaaga    900
tttgag                                                                906
```

<210> SEQ ID NO 36
<211> LENGTH: 1056
<212> TYPE: DNA
<213> ORGANISM: Artificial Sequence
<220> FEATURE:
<223> OTHER INFORMATION: Description of Artificial Sequence: recombinant
      protein of 38.8 kDa

<400> SEQUENCE: 36

```
atggctacaa aggctgtttg tgttttgaag ggtgacggcc cagttcaagg tattattaac     60
ttcgagcaga aggaaagtaa tggaccagtg aaggtgtggg aagcattaa aggactgact    120 gaaggcctgc atggattcca tgttcatgag tttggagata tacagcagg ctgtaccagt    180 gcaggtcctc acttttaatcc tctatccaga aaacacggtg ggccaaagga tgaagagagg    240
```

```
catgttggag acttgggcaa tgtgactgct gacaaagatg gtgtggccga tgtgtctatt    300
gaagattctg tgatctcact ctcaggagac cattgcatca ttggccgcac actggtggtc    360
catgaaaaag cagatgactt gggcaaaggt ggaaatgaag aaagtacaaa gacaggaaac    420
gctggaagtc gtttggcttg tggtgtaatt gggatcgccc agaatttggg aattcagatc    480
tctcgagcta gtcatataga atgtaggaaa ccatacaaag aattgagact ggaggttggg    540
aaacaaagac tcaaatatgc tcaggaagag ttatcaaatg aagtgcttcc acctcctagg    600
aaaatgaagg ggttattttc acaagctaaa atttctcttt tttatactga ggagcatgaa    660
ataatgaagt tttcttggag aggagtgact gctgatacta gggctttgag aagatttgga    720
ttctctctgg ctgctggtag aagtgtgtgg actcttgaaa tggatgctgg agttcttact    780
ggaggattga tcagattgaa tgatgagaaa tggacagaaa tgaaggatga taagattgtt    840
tcattaattg aaaagttcac aagcaataaa tattggtcta agtgaatttt ccgcatgca     900 atgttggatc ttgaagaaat tgctgccaat tcgaaggatt ttccaaatat gtctgagaca    960
gatttgtgtt tcctgttaca ttggctaaat ccaaagaaaa tcaatttagc agatagaatg   1020
cttggattgt ctggagtgca ggaaattaag gaacag                            1056
```

<210> SEQ ID NO 37
<211> LENGTH: 708
<212> TYPE: DNA
<213> ORGANISM: Artificial Sequence
<220> FEATURE:
<223> OTHER INFORMATION: Description of Artificial Sequence: recombinant
     protein of 24.9 kDa

<400> SEQUENCE: 37

```
atggctacaa aggctgtttg tgttttgaag ggtgacggcc cagttcaagg tattattaac     60
ttcgagcaga aggaaagtaa tggaccagtg aaggtgtggg aagcattaa aggactgact    120 gaaggcctgc atggattcca tgttcatgag tttggagata tacagcagg ctgtaccagt    180 gcaggtcctc actttaatcc tctatccaga aaacacggtg ggccaaagga tgaagagagg    240
catgttggag acttgggcaa tgtgactgct gacaaagatg gtgtggccga tgtgtctatt    300
gaagattctg tgatctcact ctcaggagac cattgcatca ttggccgcac actggtggtc    360
catgaaaaag cagatgactt gggcaaaggt ggaaatgaag aaagtacaaa gacaggaaac    420
gctggaagtc gtttggcttg tggtgtaatt gggatcgccc agaatttggg aattcagatc    480
tctcgaggaa tttcagatga tgacaatgat agtgcaatgg ctgagttttt ccagtctttt    540
ccatctggtg aaccatcaaa ttccaagtta tctagttttt tccaatctgt cactaatcac    600
aagtgggttg ctgtgggagc tgcagttggc attcttggag tgcttgtggg aggatggttt    660
gtgtataagc attttcccg caaagaggaa gaaccaattc cagctgaa                 708
```

<210> SEQ ID NO 38
<211> LENGTH: 1148
<212> TYPE: DNA
<213> ORGANISM: Artificial Sequence
<220> FEATURE:
<223> OTHER INFORMATION: Description of Artificial Sequence: recombinant
     protein of 41 kDa

<400> SEQUENCE: 38

```
ccatggctac aaaggctgtt tgtgttttga gggtgacgg cccagttcaa ggtattatta     60
acttcgagca gaaggaaagt aatggaccag tgaaggtgtg gggaagcatt aaaggactga   120
ctgaaggcct gcatggattc catgttcatg agtttggaga taatacagca ggctgtacca   180
```

```
gtgcaggtcc tcactttaat cctctatcca gaaaacacgg tgggccaaag gatgaagaga    240
ggcatgttgg agacttgggc aatgtgactg ctgacaaaga tggtgtggcc gatgtgtcta    300
ttgaagattc tgtgatctca ctctcaggag accattgcat cattggccgc acactggtgg    360
tccatgaaaa agcagatgac ttgggcaaag gtggaaatga agaaagtaca agacaggaa     420
acgctggaag tcgtttggct tgtggtgtaa ttgggatcgc ccagaatttg ggaattcaga    480
tctctcgagc atcaactcta gaaatagcag gattagttag gaaaaatctg gttcagtttg    540
gagttggtga gaaaaatgga tgtgtgagat gggtcatgaa tgccttagga gtgaaggatg    600
attggttgtt agtaccttct catgcttata aatttgaaaa ggattatgaa atgatggagt    660
tttacttcaa tagaggtgga acttactatt caatttcagc tggtaatgtt gttattcaat    720
ctttagatgt gggatttcaa gatgttgttt taatgaaggt tcctacaatt cccaagttta    780
gagatattac tcaacacttt attaagaaag gagatgtgcc tagagcctta aatcgcttgg    840
caacattagt gacaaccgtt aatggaactc ctatgttaat ttctgaggga ccattaaaga    900
tggaagaaaa agccacttat gttcataaga agaatgatgg tactacagtt gatttgactg    960
tagatcaggc atggagagga aaaggtgaag gtcttcctgg aatgtgtggt ggggccctag   1020
tgtcatcaaa tcagtccata cagaatgcaa ttttgggtat tcatgttgct ggaggaaatt   1080
caattcttgt ggcaaagctg gttactcaag aaatgtttca aacattgat aagaaaattg    1140
aaagtcag                                                            1148

<210> SEQ ID NO 39
<211> LENGTH: 1956
<212> TYPE: DNA
<213> ORGANISM: Artificial Sequence
<220> FEATURE:
<223> OTHER INFORMATION: Description of Artificial Sequence: recombinant
      protein of human superoxide dismutase fused with the HAV
      nonstructural protein 3D

<400> SEQUENCE: 39
atggctacaa aggctgtttg tgttttgaag ggtgacggcc cagttcaagg tattattaac     60
ttcgagcaga aggaaagtaa tggaccagtg aaggtgtggg gaagcattaa aggactgact    120
gaaggcctgc atggattcca tgttcatgag tttggagata tacagcagg ctgtaccagt     180
gcaggtcctc actttaatcc tctatccaga aaacacggtg ggccaaagga tgaagagagg    240
catgttggag acttgggcaa tgtgactgct gacaaagatg tgtggccga tgtgtctatt     300
gaagattctg tgatctcact ctcaggagac cattgcatca ttggccgcac actggtggtc    360
catgaaaaag cagatgactt gggcaaaggt ggaaatgaag aaagtacaaa gacaggaaac    420
gctggaagtc gtttggcttg tggtgtaatt gggatcgccc agaatttggg aattcagatc    480
tctcgagcaa gaataatgaa agtggaattt actcaatgtt caatgaatgt agtctccaaa    540
acgcttttta gaaagagtcc cattcatcac cacattgata aaaccatgat taattttcct    600
gcagctatgc cttttctcta aagctgaaatt gatccaatgg ctatgacgtt gtccaaatat    660
tcattaccta ttgtggagga accagaggat tacaaggaag cttcagtttt ttatcaaaac    720
aaaatagtag gcaagactca gctagttgat gactttttag atcttgatat ggctattaca    780
ggggctccag gcattgatgc tatcaatatg gattcatctc ctgggttttcc ttatgttcaa    840
gaaaaattga ccaaaagaga tttaatttgg ttggatgaaa atggtttgct gttaggagtt    900
cacccaagat tggcccagag aatttttatt aatactgtca tgatggaaaa ttgttctgac    960
```

-continued

```
ttagatgttg tttttacaac ttgtccaaaa gatgaattga gaccattaga gaaagttttg    1020
gaatcaaaaa caagagccat tgatgcttgt cctttggatt atacaattct atgtcgaatg    1080
tattggggtc cagctatcag ttatttccat ttgaatccag ggtttcacac aggtgttgct    1140
attggcatag atcctgataa acagtgggat gaattattta aaacaatgat aagatttgga    1200
gatgttggtc ttgatttaga tttctctgct tttgatgcca gtcttagtcc atttatgatt    1260
agggaagcag gtagaatcat gagtgaatta tctggaacac catctcattt tggaacagct    1320
cttatcaata ctatcattta ttctaaacat ctgctgtaca actgttgtta tcatgtttgt    1380
ggttcaatgc cttctgggtc tccttgcaca gctttgttga attcaattat taataatatt    1440
aatctgtatt atgtgttttc taaaatattt ggaaagtctc cagttttctt ttgtcaagct    1500
ttgaggatcc tttgttacgg agatgatgtt ttgatagttt tttccagaga tgttcaaatt    1560
gacaatcttg acttgattgg acagaaaatt gtagatgagt tcaaaaaact tggcatgaca    1620
gccacctcag ctgataaaaa tgtgcctcaa ctgaagccag tttcagaatt gacttttctc    1680
aaaagatctt tcaatttggt ggaggataga attagacctg caatttcaga aaagacaatt    1740
tggtctttga tggcttggca gagaagtaac gctgagtttg agcagaattt agaaaatgct    1800
cagtggtttg ctttatgca tggctatgag ttctatcaga aattttatta ttttgttcag    1860
tcctgtttgg agaaagagat gatagaatat agacttaaat cttatgattg gtggagaatg    1920
agattttatg accagtgttt catttgtgac ctttca                              1956
```

<210> SEQ ID NO 40
<211> LENGTH: 836
<212> TYPE: PRT
<213> ORGANISM: Artificial Sequence
<220> FEATURE:
<223> OTHER INFORMATION: Description of Artificial Sequence: recombinant protein of 94 kDa

<400> SEQUENCE: 40

```
Met Asn Met Ser Lys Gln Gly Ile Phe Arg Thr Val Gly Ser Gly Leu
 1               5                  10                  15

Asp His Ile Leu Ser Leu Ala Asp Ile Glu Glu Glu Gln Met Ile Gln
            20                  25                  30

Ser Val Asp Arg Thr Ala Val Thr Gly Ala Ser Tyr Phe Thr Ser Val
        35                  40                  45

Asp Gln Ser Ser Val His Thr Ala Glu Val Gly Ser His Gln Ile Glu
    50                  55                  60

Pro Leu Lys Thr Ser Val Asp Lys Pro Gly Ser Lys Lys Thr Gln Gly
65                  70                  75                  80

Glu Lys Phe Phe Leu Ile His Ser Ala Asp Trp Leu Thr Thr His Ala
                85                  90                  95

Leu Phe His Glu Val Ala Lys Leu Asp Val Val Lys Leu Leu Tyr Asn
            100                 105                 110

Glu Gln Phe Ala Val Gln Gly Leu Leu Arg Tyr His Thr Tyr Ala Arg
        115                 120                 125

Phe Gly Ile Glu Ile Gln Val Gln Ile Asn Pro Thr Pro Phe Gln Gln
    130                 135                 140

Gly Gly Leu Ile Cys Ala Met Val Pro Gly Asp Gln Ser Tyr Gly Ser
145                 150                 155                 160

Ile Ala Ser Leu Thr Val Tyr Pro His Gly Leu Leu Asn Cys Asn Ile
                165                 170                 175

Asn Asn Val Val Arg Ile Lys Val Pro Phe Ile Tyr Thr Arg Gly Ala
```

-continued

```
                180             185             190
Tyr His Phe Lys Asp Pro Gln Tyr Pro Val Trp Glu Leu Thr Ile Arg
            195                 200                 205
Val Trp Ser Glu Leu Asn Ile Gly Thr Gly Thr Ser Ala Tyr Thr Ser
    210                 215                 220
Leu Asn Val Leu Ala Arg Phe Thr Asp Leu Glu Leu His Gly Leu Thr
225                 230                 235                 240
Pro Leu Ser Thr Gln Met Met Arg Asn Glu Phe Arg Val Ser Thr Thr
                245                 250                 255
Glu Asn Val Val Asn Leu Ser Asn Tyr Glu Asp Ala Arg Ala Lys Met
            260                 265                 270
Ser Phe Ala Leu Asp Gln Glu Asp Trp Lys Ser Asp Pro Ser Gln Gly
        275                 280                 285
Gly Gly Ile Lys Ile Thr His Phe Thr Trp Thr Ser Ile Pro Thr
    290                 295                 300
Leu Ala Ala Gln Phe Pro Phe Asn Ala Ser Asp Ser Val Gly Gln Gln
305                 310                 315                 320
Ile Lys Val Ile Pro Val Asp Pro Tyr Phe Phe Gln Met Thr Asn Thr
                325                 330                 335
Asn Pro Asp Gln Lys Cys Ile Thr Ala Leu Ala Ser Ile Cys Gln Met
                340                 345                 350
Phe Cys Phe Trp Arg Gly Asp Leu Val Phe Asp Phe Gln Val Phe Pro
        355                 360                 365
Thr Lys Tyr His Ser Gly Arg Leu Leu Phe Cys Phe Val Pro Gly Asn
    370                 375                 380
Glu Leu Ile Asp Val Thr Gly Ile Thr Leu Lys Gln Ala Thr Ala
385                 390                 395                 400
Pro Cys Ala Val Met Asp Ile Thr Gly Val Gln Ser Thr Leu Arg Phe
                405                 410                 415
Arg Val Pro Trp Ile Ser Asp Thr Pro Tyr Arg Val Asn Arg Tyr Thr
            420                 425                 430
Lys Ser Ala His Gln Lys Gly Glu Tyr Thr Ala Ile Gly Lys Leu Ile
        435                 440                 445
Val Tyr Cys Tyr Asn Arg Leu Thr Ser Pro Ser Asn Val Ala Ser His
    450                 455                 460
Val Arg Val Asn Val Tyr Leu Ser Ala Ile Asn Leu Glu Cys Phe Ala
465                 470                 475                 480
Pro Leu Tyr His Ala Met Asp Val Thr Thr Gln Val Gly Asp Asp Ser
                485                 490                 495
Gly Gly Phe Ser Thr Thr Val Ser Thr Glu Gln Asn Val Pro Asp Pro
            500                 505                 510
Gln Val Gly Ile Thr Thr Met Arg Asp Ser Lys Gly Lys Ala Asn Arg
        515                 520                 525
Gly Lys Met Asp Val Ser Gly Val Gln Ala Pro Val Gly Ala Ile Thr
    530                 535                 540
Thr Ile Glu Asp Pro Val Leu Ala Lys Lys Val Pro Glu Thr Phe Pro
545                 550                 555                 560
Glu Leu Lys Pro Gly Glu Ser Arg His Thr Ser Asp His Met Ser Ile
                565                 570                 575
Tyr Lys Phe Met Gly Arg Ser His Phe Leu Cys Thr Phe Thr Phe Asn
            580                 585                 590
Ser Asn Asn Lys Glu Tyr Thr Phe Pro Ile Thr Leu Ser Ser Thr Ser
        595                 600                 605
```

-continued

```
Asn Pro Pro His Gly Leu Pro Ser Thr Leu Arg Trp Phe Phe Asn Leu
    610                 615                 620

Phe Gln Leu Tyr Arg Gly Pro Leu Asp Leu Thr Ile Ile Thr Gly
625                 630                 635                 640

Ala Thr Asp Val Asp Gly Met Ala Trp Phe Thr Pro Val Gly Leu Ala
                645                 650                 655

Val Asp Thr Pro Trp Val Glu Lys Glu Ser Ala Leu Ser Ile Asp Tyr
                660                 665                 670

Lys Thr Ala Leu Gly Ala Val Arg Phe Asn Thr Arg Arg Thr Gly Ile
                675                 680                 685

Ile Gln Ile Arg Leu Pro Trp Tyr Ser Tyr Leu Tyr Ala Val Ser Gly
    690                 695                 700

Ala Leu Asp Gly Leu Gly Asp Lys Thr Asp Ser Thr Phe Gly Leu Val
705                 710                 715                 720

Ser Ile Gln Ile Ala Asn Tyr Asn His Ser Asp Glu Tyr Leu Ser Phe
                725                 730                 735

Ser Cys Tyr Leu Ser Val Thr Glu Gln Ser Glu Phe Tyr Phe Pro Arg
                740                 745                 750

Ala Pro Leu Asn Ser Asn Ala Met Leu Ser Thr Glu Ser Met Met Ser
                755                 760                 765

Arg Ile Ala Ala Gly Asp Leu Glu Ser Ser Val Asp Asp Pro Arg Ser
770                 775                 780

Glu Glu Asp Arg Arg Phe Glu Ser His Ile Glu Cys Arg Lys Pro Tyr
785                 790                 795                 800

Lys Glu Leu Arg Leu Glu Val Gly Lys Gln Arg Leu Lys Tyr Ala Gln
                805                 810                 815

Glu Glu Leu Ser Asn Glu Val Leu Pro Pro Arg Lys Ile Lys Gly
                820                 825                 830

Leu Phe Ser Gln
        835
```

<210> SEQ ID NO 41
<211> LENGTH: 980
<212> TYPE: PRT
<213> ORGANISM: Artificial Sequence
<220> FEATURE:
<223> OTHER INFORMATION: Description of Artificial Sequence: recombinant protein of 115.5 kDa

<400> SEQUENCE: 41

```
Met Asn Met Ser Lys Gln Gly Ile Phe Gln Thr Val Gly Ser Gly Leu
 1               5                  10                  15

Asp His Ile Leu Ser Leu Ala Asp Ile Glu Glu Glu Gln Met Ile Gln
            20                  25                  30

Ser Val Asp Arg Thr Ala Val Thr Gly Ala Ser Tyr Phe Thr Ser Val
        35                  40                  45

Asp Gln Ser Ser Val His Thr Ala Glu Val Gly Ser His Gln Ile Glu
    50                  55                  60

Pro Leu Lys Thr Ser Val Asp Lys Pro Gly Lys Lys Thr Gln Gly
65                  70                  75                  80

Glu Lys Phe Phe Leu Ile His Ser Ala Asp Trp Leu Thr Thr His Ala
                85                  90                  95

Leu Phe His Glu Val Ala Lys Leu Asp Val Val Lys Leu Leu Tyr Asn
            100                 105                 110

Glu Gln Phe Ala Val Gln Gly Leu Leu Arg Tyr His Thr Tyr Ala Arg
```

-continued

```
            115                 120                 125
Phe Gly Ile Glu Ile Gln Val Gln Ile Asn Pro Thr Pro Phe Gln Gln
    130                 135                 140

Gly Gly Leu Ile Cys Ala Met Val Pro Gly Asp Gln Ser Tyr Gly Ser
145                 150                 155                 160

Ile Ala Ser Leu Thr Val Tyr Pro His Gly Leu Leu Asn Cys Asn Ile
                165                 170                 175

Asn Asn Val Val Arg Ile Lys Val Pro Phe Ile Tyr Thr Arg Gly Ala
            180                 185                 190

Tyr His Phe Lys Asp Pro Gln Tyr Pro Val Trp Glu Leu Thr Ile Arg
        195                 200                 205

Val Trp Ser Glu Leu Asn Ile Gly Thr Gly Thr Ser Ala Tyr Thr Ser
    210                 215                 220

Leu Asn Val Leu Ala Arg Phe Thr Asp Leu Glu Leu His Gly Leu Thr
225                 230                 235                 240

Pro Leu Ser Thr Gln Met Met Arg Asn Glu Phe Arg Val Ser Thr Thr
                245                 250                 255

Glu Asn Val Val Asn Leu Ser Asn Tyr Glu Asp Ala Arg Ala Lys Met
            260                 265                 270

Ser Phe Ala Leu Asp Gln Glu Asp Trp Lys Ser Asp Pro Ser Gln Gly
        275                 280                 285

Gly Gly Ile Lys Ile Thr His Phe Thr Thr Trp Thr Ser Ile Pro Thr
    290                 295                 300

Leu Ala Ala Gln Phe Pro Phe Asn Ala Ser Asp Ser Val Gly Gln Gln
305                 310                 315                 320

Ile Lys Val Ile Pro Val Asp Pro Tyr Phe Phe Gln Met Thr Asn Thr
                325                 330                 335

Asn Pro Asp Gln Lys Cys Ile Thr Ala Leu Ala Ser Ile Cys Gln Met
            340                 345                 350

Phe Cys Phe Trp Arg Gly Asp Leu Val Phe Asp Phe Gln Val Phe Pro
        355                 360                 365

Thr Lys Tyr His Ser Gly Arg Leu Leu Phe Cys Phe Val Pro Gly Asn
    370                 375                 380

Glu Leu Ile Asp Val Thr Gly Ile Thr Leu Lys Gln Ala Thr Thr Ala
385                 390                 395                 400

Pro Cys Ala Val Met Asp Ile Thr Gly Val Gln Ser Thr Leu Arg Phe
                405                 410                 415

Arg Val Pro Trp Ile Ser Asp Thr Pro Tyr Arg Val Asn Arg Tyr Thr
            420                 425                 430

Lys Ser Ala His Gln Lys Gly Glu Tyr Thr Ala Ile Gly Lys Leu Ile
        435                 440                 445

Val Tyr Cys Tyr Asn Arg Leu Thr Ser Pro Ser Asn Val Ala Ser His
    450                 455                 460

Val Arg Val Asn Val Tyr Leu Ser Ala Ile Asn Leu Glu Cys Phe Ala
465                 470                 475                 480

Pro Leu Tyr His Ala Met Asp Val Thr Thr Gln Val Gly Asp Asp Ser
                485                 490                 495

Gly Gly Phe Ser Thr Thr Val Ser Thr Glu Gln Asn Val Pro Asp Pro
            500                 505                 510

Gln Val Gly Ile Thr Thr Met Arg Asp Leu Lys Gly Lys Ala Asn Arg
        515                 520                 525

Gly Lys Met Asp Val Ser Gly Val Gln Ala Pro Val Gly Ala Ile Thr
    530                 535                 540
```

-continued

```
Thr Ile Glu Asp Pro Val Leu Ala Lys Lys Val Pro Glu Thr Phe Pro
545                 550                 555                 560

Glu Leu Lys Pro Gly Glu Ser Arg His Thr Ser Asp His Met Ser Ile
                565                 570                 575

Tyr Lys Phe Met Gly Arg Ser His Phe Leu Cys Thr Phe Thr Phe Asn
                580                 585                 590

Ser Asn Asn Lys Glu Tyr Thr Phe Pro Ile Thr Leu Ser Ser Thr Ser
                595                 600                 605

Asn Pro Pro His Gly Leu Pro Ser Thr Leu Arg Trp Phe Phe Asn Leu
            610                 615                 620

Phe Gln Leu Tyr Arg Gly Pro Leu Asp Leu Thr Ile Ile Thr Gly
625                 630                 635                 640

Ala Thr Asp Val Asp Gly Met Ala Trp Phe Thr Pro Val Gly Leu Ala
                645                 650                 655

Val Asp Thr Pro Trp Val Glu Lys Glu Ser Ala Leu Ser Ile Asp Tyr
                660                 665                 670

Lys Thr Ala Leu Gly Ala Val Arg Phe Asn Thr Arg Arg Thr Gly Asn
            675                 680                 685

Ile Gln Ile Arg Leu Pro Trp Tyr Ser Tyr Leu Tyr Ala Val Ser Gly
            690                 695                 700

Ala Leu Asp Gly Leu Gly Asp Lys Thr Asp Ser Thr Phe Gly Leu Val
705                 710                 715                 720

Ser Ile Gln Ile Ala Asn Tyr Asn His Ser Asp Glu Tyr Leu Ser Phe
                725                 730                 735

Ser Cys Tyr Leu Ser Val Thr Glu Gln Ser Glu Phe Tyr Phe Pro Arg
                740                 745                 750

Ala Pro Leu Asn Ser Asn Ala Met Leu Ser Thr Glu Ser Met Met Ser
                755                 760                 765

Arg Ile Ala Ala Gly Asp Leu Glu Ser Ser Val Asp Asp Pro Arg Ser
770                 775                 780

Glu Glu Asp Arg Arg Phe Glu Ser His Ile Glu Cys Arg Lys Pro Tyr
785                 790                 795                 800

Lys Glu Leu Arg Leu Glu Val Gly Lys Gln Arg Leu Lys Tyr Ala Gln
                805                 810                 815

Glu Glu Leu Ser Asn Glu Val Leu Pro Pro Arg Lys Met Lys Gly
                820                 825                 830

Leu Phe Ser Gln Ala Lys Ile Ser Leu Phe Tyr Thr Glu Glu His Glu
                835                 840                 845

Ile Met Lys Phe Ser Trp Arg Gly Val Thr Ala Asp Thr Arg Ala Leu
850                 855                 860

Arg Arg Phe Gly Phe Ser Leu Ala Ala Gly Arg Ser Val Trp Thr Leu
865                 870                 875                 880

Glu Met Asp Ala Gly Val Leu Thr Gly Gly Leu Ile Arg Leu Asn Asp
                885                 890                 895

Glu Lys Trp Thr Glu Met Lys Asp Asp Lys Ile Val Ser Leu Ile Glu
            900                 905                 910

Lys Phe Thr Ser Asn Lys Tyr Trp Ser Lys Val Asn Phe Pro His Ala
            915                 920                 925

Met Leu Asp Leu Glu Glu Ile Ala Ala Asn Ser Lys Asp Phe Pro Asn
            930                 935                 940

Met Ser Glu Thr Asp Leu Cys Phe Leu Leu His Trp Leu Asn Pro Lys
945                 950                 955                 960
```

```
Lys Ile Asn Leu Ala Asp Arg Met Leu Gly Leu Ser Gly Val Gln Glu
                965                 970                 975
Ile Lys Glu Gln
            980

<210> SEQ ID NO 42
<211> LENGTH: 223
<212> TYPE: PRT
<213> ORGANISM: Artificial Sequence
<220> FEATURE:
<223> OTHER INFORMATION: Description of Artificial Sequence: recombinant
      protein of 25 kDa

<400> SEQUENCE: 42

Met Asp Ile Glu Glu Gln Met Ile Gln Ser Val Asp Arg Thr Ala
  1               5                  10                  15

Val Thr Gly Ala Ser Tyr Phe Thr Ser Val Asp Gln Ser Ser Val His
                 20                  25                  30

Thr Ala Glu Val Gly Ser His Gln Ile Glu Pro Leu Lys Thr Ser Val
             35                  40                  45

Asp Lys Pro Gly Ser Lys Lys Thr Gln Gly Glu Lys Phe Phe Leu Ile
 50                  55                  60

His Ser Ala Asp Trp Leu Thr Thr His Ala Leu Phe His Glu Val Ala
 65                  70                  75                  80

Lys Leu Asp Val Lys Leu Leu Tyr Asn Glu Gln Phe Ala Val Gln
                 85                  90                  95

Gly Leu Leu Arg Tyr His Thr Tyr Ala Arg Phe Gly Ile Glu Ile Gln
                100                 105                 110

Val Gln Ile Asn Pro Thr Pro Phe Gln Gln Gly Gly Leu Ile Cys Ala
            115                 120                 125

Met Val Pro Gly Asp Gln Ser Tyr Gly Ser Ile Ala Ser Leu Thr Val
        130                 135                 140

Tyr Pro His Gly Leu Leu Asn Cys Asn Ile Asn Asn Val Val Arg Ile
145                 150                 155                 160

Lys Val Pro Phe Ile Tyr Thr Arg Gly Ala Tyr His Phe Lys Asp Pro
                165                 170                 175

Gln Tyr Pro Val Trp Glu Leu Thr Ile Arg Val Trp Ser Glu Leu Asn
            180                 185                 190

Ile Gly Thr Gly Thr Ser Ala Tyr Thr Ser Leu Asn Val Leu Ala Arg
        195                 200                 205

Phe Thr Asp Leu Glu Leu His Gly Leu Thr Pro Leu Ser Thr Gln
    210                 215                 220

<210> SEQ ID NO 43
<211> LENGTH: 248
<212> TYPE: PRT
<213> ORGANISM: Artificial Sequence
<220> FEATURE:
<223> OTHER INFORMATION: Description of Artificial Sequence: recombinant
      protein of 28 kDa

<400> SEQUENCE: 43

Met Ala Met Met Arg Asn Glu Phe Arg Val Ser Thr Thr Glu Asn Val
  1               5                  10                  15

Val Asn Leu Ser Asn Tyr Glu Asp Ala Arg Ala Lys Met Ser Phe Ala
                 20                  25                  30

Leu Asp Gln Glu Asp Trp Lys Ser Asp Pro Ser Gln Gly Gly Gly Ile
             35                  40                  45
```

-continued

```
Lys Ile Thr His Phe Thr Thr Trp Thr Ser Ile Pro Thr Leu Ala Ala
 50                  55                  60

Gln Phe Pro Phe Asn Ala Ser Asp Ser Val Gly Gln Gln Ile Lys Val
 65                  70                  75                  80

Ile Pro Val Asp Pro Tyr Phe Phe Gln Met Thr Asn Thr Asn Pro Asp
                 85                  90                  95

Gln Lys Cys Ile Thr Ala Leu Ala Ser Ile Cys Gln Met Phe Cys Phe
            100                 105                 110

Trp Arg Gly Asp Leu Val Phe Asp Phe Gln Val Phe Pro Thr Lys Tyr
            115                 120                 125

His Ser Gly Arg Leu Leu Phe Cys Phe Val Pro Gly Asn Glu Leu Ile
        130                 135                 140

Asp Val Thr Gly Ile Thr Leu Lys Gln Ala Thr Thr Ala Pro Cys Ala
145                 150                 155                 160

Val Met Asp Ile Thr Gly Val Gln Ser Thr Leu Arg Phe Arg Val Pro
                165                 170                 175

Trp Ile Ser Asp Thr Pro Tyr Arg Val Asn Arg Tyr Thr Lys Ser Ala
            180                 185                 190

His Gln Lys Gly Glu Tyr Thr Ala Ile Gly Lys Leu Ile Val Tyr Cys
        195                 200                 205

Tyr Asn Arg Leu Thr Ser Pro Ser Asn Val Ala Ser His Val Arg Val
210                 215                 220

Asn Val Tyr Leu Ser Ala Ile Asn Leu Glu Cys Phe Ala Pro Leu Tyr
225                 230                 235                 240

His Ala Met Asp Val Thr Thr Gln
                245
```

<210> SEQ ID NO 44
<211> LENGTH: 302
<212> TYPE: PRT
<213> ORGANISM: Artificial Sequence
<220> FEATURE:
<223> OTHER INFORMATION: Description of Artificial Sequence: recombinant
      protein of 33.3 kDa

<400> SEQUENCE: 44

```
Met Ala Val Gly Asp Asp Ser Gly Gly Phe Ser Thr Thr Val Ser Thr
 1               5                  10                  15

Glu Gln Asn Val Pro Asp Pro Gln Val Gly Ile Thr Thr Met Arg Asp
                 20                  25                  30

Ser Lys Gly Lys Ala Asn Arg Gly Lys Met Asp Val Ser Gly Val Gln
            35                  40                  45

Ala Pro Val Gly Ala Ile Thr Thr Ile Glu Asp Pro Val Leu Ala Lys
 50                  55                  60

Lys Val Pro Glu Thr Phe Pro Glu Leu Lys Pro Gly Glu Ser Arg His
 65                  70                  75                  80

Thr Ser Asp His Met Ser Ile Tyr Lys Phe Met Gly Arg Ser His Phe
                 85                  90                  95

Leu Cys Thr Phe Thr Phe Asn Ser Asn Asn Lys Glu Tyr Thr Phe Pro
            100                 105                 110

Ile Thr Leu Ser Ser Thr Ser Asn Pro Pro His Gly Leu Pro Ser Thr
            115                 120                 125

Leu Arg Trp Phe Phe Asn Leu Phe Gln Leu Tyr Arg Gly Pro Leu Asp
        130                 135                 140

Leu Thr Ile Ile Ile Thr Gly Ala Thr Asp Val Asp Gly Met Ala Trp
145                 150                 155                 160
```

```
Phe Thr Pro Val Gly Leu Ala Val Asp Thr Pro Trp Val Glu Lys Glu
                165                 170                 175

Ser Ala Leu Ser Ile Asp Tyr Lys Thr Ala Leu Gly Ala Val Arg Phe
            180                 185                 190

Asn Thr Arg Arg Thr Gly Asn Ile Gln Ile Arg Leu Pro Trp Tyr Ser
        195                 200                 205

Tyr Leu Tyr Ala Val Ser Gly Ala Leu Asp Gly Leu Gly Gly Lys Thr
    210                 215                 220

Asp Ser Thr Phe Gly Leu Val Ser Ile Gln Ile Ala Asn Tyr Asn His
225                 230                 235                 240

Ser Asp Glu Tyr Leu Ser Phe Ser Cys Tyr Leu Ser Val Thr Glu Gln
                245                 250                 255

Ser Glu Phe Tyr Phe Pro Arg Ala Pro Leu Asn Ser Asn Ala Met Leu
            260                 265                 270

Ser Thr Glu Ser Met Met Ser Arg Ile Ala Ala Gly Asp Leu Glu Ser
        275                 280                 285

Ser Val Asp Asp Pro Arg Ser Glu Glu Asp Arg Arg Phe Glu
    290                 295                 300

<210> SEQ ID NO 45
<211> LENGTH: 352
<212> TYPE: PRT
<213> ORGANISM: Artificial Sequence
<220> FEATURE:
<223> OTHER INFORMATION: Description of Artificial Sequence: recombinant
      protein of 38.8 kDa

<400> SEQUENCE: 45

Met Ala Thr Lys Ala Val Cys Val Leu Lys Gly Asp Gly Pro Val Gln
 1               5                  10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
        50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Asn Leu Gly Ile Gln Ile
145                 150                 155                 160

Ser Arg Ala Ser His Ile Glu Cys Arg Lys Pro Tyr Lys Glu Leu Arg
                165                 170                 175

Leu Glu Val Gly Lys Gln Arg Leu Lys Tyr Ala Gln Glu Glu Leu Ser
            180                 185                 190

Asn Glu Val Leu Pro Pro Pro Arg Lys Met Lys Gly Leu Phe Ser Gln
        195                 200                 205

Ala Lys Ile Ser Leu Phe Tyr Thr Glu Glu His Glu Ile Met Lys Phe
```

```
              210                 215                 220
Ser Trp Arg Gly Val Thr Ala Asp Thr Arg Ala Leu Arg Arg Phe Gly
225                 230                 235                 240

Phe Ser Leu Ala Ala Gly Arg Ser Val Trp Thr Leu Glu Met Asp Ala
                245                 250                 255

Gly Val Leu Thr Gly Gly Leu Ile Arg Leu Asn Asp Glu Lys Trp Thr
                260                 265                 270

Glu Met Lys Asp Asp Lys Ile Val Ser Leu Ile Glu Lys Phe Thr Ser
                275                 280                 285

Asn Lys Tyr Trp Ser Lys Val Asn Phe Pro His Ala Met Leu Asp Leu
                290                 295                 300

Glu Glu Ile Ala Ala Asn Ser Lys Asp Phe Pro Asn Met Ser Glu Thr
305                 310                 315                 320

Asp Leu Cys Phe Leu Leu His Trp Leu Asn Pro Lys Lys Ile Asn Leu
                325                 330                 335

Ala Asp Arg Met Leu Gly Leu Ser Gly Val Gln Glu Ile Lys Glu Gln
                340                 345                 350

<210> SEQ ID NO 46
<211> LENGTH: 236
<212> TYPE: PRT
<213> ORGANISM: Artificial Sequence
<220> FEATURE:
<223> OTHER INFORMATION: Description of Artificial Sequence: recombinant
      protein of 24.9 kDa

<400> SEQUENCE: 46

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
        50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
                100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
130                 135                 140

Leu Ala Cys Gly Val Ile Gly Ile Ala Gln Asn Leu Gly Ile Gln Ile
145                 150                 155                 160

Ser Arg Gly Ile Ser Asp Asp Asn Asp Ser Ala Met Ala Glu Phe
                165                 170                 175

Phe Gln Ser Phe Pro Ser Gly Glu Pro Ser Asn Ser Lys Leu Ser Ser
                180                 185                 190

Phe Phe Gln Ser Val Thr Asn His Lys Trp Val Ala Val Gly Ala Ala
            195                 200                 205

Val Gly Ile Leu Gly Val Leu Val Gly Gly Trp Phe Val Tyr Lys His
210                 215                 220
```

```
Phe Ser Arg Lys Glu Glu Glu Pro Ile Pro Ala Glu
225                 230                 235
```

<210> SEQ ID NO 47
<211> LENGTH: 382
<212> TYPE: PRT
<213> ORGANISM: Artificial Sequence
<220> FEATURE:
<223> OTHER INFORMATION: Description of Artificial Sequence: recombinant
      protein of 41 kDa

<400> SEQUENCE: 47

```
Met Ala Thr Lys Ala Val Cys Val Leu Lys Gly Asp Gly Pro Val Gln
  1               5                  10                  15

Gly Ile Ile Asn Phe Glu Gln Lys Glu Ser Asn Gly Pro Val Lys Val
                 20                  25                  30

Trp Gly Ser Ile Lys Gly Leu Thr Glu Gly Leu His Gly Phe His Val
             35                  40                  45

His Glu Phe Gly Asp Asn Thr Ala Gly Cys Thr Ser Ala Gly Pro His
 50                  55                  60

Phe Asn Pro Leu Ser Arg Lys His Gly Pro Lys Asp Glu Glu Arg
 65                  70                  75                  80

His Val Gly Asp Leu Gly Asn Val Thr Ala Asp Lys Asp Gly Val Ala
                 85                  90                  95

Asp Val Ser Ile Glu Asp Ser Val Ile Ser Leu Ser Gly Asp His Cys
                100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
130                 135                 140

Leu Ala Cys Gly Val Ile Gly Ile Ala Gln Asn Leu Gly Ile Gln Ile
145                 150                 155                 160

Ser Arg Ala Ser Thr Leu Glu Ile Ala Gly Leu Val Arg Lys Asn Leu
                165                 170                 175

Val Gln Phe Gly Val Gly Glu Lys Asn Gly Cys Val Arg Trp Val Met
            180                 185                 190

Asn Ala Leu Gly Val Lys Asp Asp Trp Leu Leu Val Pro Ser His Ala
        195                 200                 205

Tyr Lys Phe Glu Lys Asp Tyr Glu Met Met Glu Phe Tyr Phe Asn Arg
210                 215                 220

Gly Gly Thr Tyr Tyr Ser Ile Ser Ala Gly Asn Val Val Ile Gln Ser
225                 230                 235                 240

Leu Asp Val Gly Phe Gln Asp Val Leu Met Lys Val Pro Thr Ile
                245                 250                 255

Pro Lys Phe Arg Asp Ile Thr Gln His Phe Ile Lys Lys Gly Asp Val
            260                 265                 270

Pro Arg Ala Leu Asn Arg Leu Ala Thr Leu Val Thr Thr Val Asn Gly
        275                 280                 285

Thr Pro Met Leu Ile Ser Glu Gly Pro Leu Lys Met Glu Glu Lys Ala
    290                 295                 300

Thr Tyr Val His Lys Lys Asn Asp Gly Thr Thr Val Asp Leu Thr Val
305                 310                 315                 320

Asp Gln Ala Trp Arg Gly Lys Gly Glu Gly Leu Pro Gly Met Cys Gly
                325                 330                 335

Gly Ala Leu Val Ser Ser Asn Gln Ser Ile Gln Asn Ala Ile Leu Gly
            340                 345                 350
```

```
Ile His Val Ala Gly Gly Asn Ser Ile Leu Val Ala Lys Leu Val Thr
            355                 360                 365

Gln Glu Met Phe Gln Asn Ile Asp Lys Lys Ile Glu Ser Gln
    370                 375                 380

<210> SEQ ID NO 48
<211> LENGTH: 652
<212> TYPE: PRT
<213> ORGANISM: Artificial Sequence
<220> FEATURE:
<223> OTHER INFORMATION: Description of Artificial Sequence: recombinant
      protein of human superoxide dismutase fused with the HAV
      nonstructural protein

<400> SEQUENCE: 48

Met Ala Thr Lys Ala Val Cys Val Leu Lys Gly Asp Gly Pro Val Gln
  1               5                  10                  15

Gly Ile Ile Asn Phe Glu Gln Lys Glu Ser Asn Gly Pro Val Lys Val
             20                  25                  30

Trp Gly Ser Ile Lys Gly Leu Thr Glu Gly Leu His Gly Phe His Val
         35                  40                  45

His Glu Phe Gly Asp Asn Thr Ala Gly Cys Thr Ser Ala Gly Pro His
     50                  55                  60

Phe Asn Pro Leu Ser Arg Lys His Gly Gly Pro Lys Asp Glu Glu Arg
 65                  70                  75                  80

His Val Gly Asp Leu Gly Asn Val Thr Ala Asp Lys Asp Gly Val Ala
                 85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Asn Leu Gly Ile Gln Ile
145                 150                 155                 160

Ser Arg Ala Arg Ile Met Lys Val Glu Phe Thr Gln Cys Ser Met Asn
                165                 170                 175

Val Val Ser Lys Thr Leu Phe Arg Lys Ser Pro Ile His His His Ile
            180                 185                 190

Asp Lys Thr Met Ile Asn Phe Pro Ala Ala Met Pro Phe Ser Lys Ala
        195                 200                 205

Glu Ile Asp Pro Met Ala Met Thr Leu Ser Lys Tyr Ser Leu Pro Ile
    210                 215                 220

Val Glu Glu Pro Glu Asp Tyr Lys Glu Ala Ser Val Phe Tyr Gln Asn
225                 230                 235                 240

Lys Ile Val Gly Lys Thr Gln Leu Val Asp Asp Phe Leu Asp Leu Asp
                245                 250                 255

Met Ala Ile Thr Gly Ala Pro Gly Ile Asp Ala Ile Asn Met Asp Ser
            260                 265                 270

Ser Pro Gly Phe Pro Tyr Val Gln Glu Lys Leu Thr Lys Arg Asp Leu
        275                 280                 285

Ile Trp Leu Asp Glu Asn Gly Leu Leu Leu Gly Val His Pro Arg Leu
    290                 295                 300

Ala Gln Arg Ile Leu Phe Asn Thr Val Met Met Glu Asn Cys Ser Asp
305                 310                 315                 320
```

-continued

```
Leu Asp Val Val Phe Thr Thr Cys Pro Lys Asp Glu Leu Arg Pro Leu
                325                 330                 335

Glu Lys Val Leu Glu Ser Lys Thr Arg Ala Ile Asp Ala Cys Pro Leu
            340                 345                 350

Asp Tyr Thr Ile Leu Cys Arg Met Tyr Trp Gly Pro Ala Ile Ser Tyr
        355                 360                 365

Phe His Leu Asn Pro Gly Phe His Thr Gly Val Ala Ile Gly Ile Asp
    370                 375                 380

Pro Asp Lys Gln Trp Asp Glu Leu Phe Lys Thr Met Ile Arg Phe Gly
385                 390                 395                 400

Asp Val Gly Leu Asp Leu Asp Phe Ser Ala Phe Asp Ala Ser Leu Ser
                405                 410                 415

Pro Phe Met Ile Arg Glu Ala Gly Arg Ile Met Ser Glu Leu Ser Gly
            420                 425                 430

Thr Pro Ser His Phe Gly Thr Ala Leu Ile Asn Thr Ile Ile Tyr Ser
        435                 440                 445

Lys His Leu Leu Tyr Asn Cys Cys Tyr His Val Cys Gly Ser Met Pro
    450                 455                 460

Ser Gly Ser Pro Cys Thr Ala Leu Leu Asn Ser Ile Ile Asn Asn Ile
465                 470                 475                 480

Asn Leu Tyr Tyr Val Phe Ser Lys Ile Phe Gly Lys Ser Pro Val Phe
                485                 490                 495

Phe Cys Gln Ala Leu Arg Ile Leu Cys Tyr Gly Asp Asp Val Leu Ile
            500                 505                 510

Val Phe Ser Arg Asp Val Gln Ile Asp Asn Leu Asp Leu Ile Gly Gln
        515                 520                 525

Lys Ile Val Asp Glu Phe Lys Lys Leu Gly Met Thr Ala Thr Ser Ala
    530                 535                 540

Asp Lys Asn Val Pro Gln Leu Lys Pro Val Ser Glu Leu Thr Phe Leu
545                 550                 555                 560

Lys Arg Ser Phe Asn Leu Val Glu Asp Arg Ile Arg Pro Ala Ile Ser
                565                 570                 575

Glu Lys Thr Ile Trp Ser Leu Met Ala Trp Gln Arg Ser Asn Ala Glu
            580                 585                 590

Phe Glu Gln Asn Leu Glu Asn Ala Gln Trp Phe Ala Phe Met His Gly
        595                 600                 605

Tyr Glu Phe Tyr Gln Lys Phe Tyr Tyr Phe Val Gln Ser Cys Leu Glu
    610                 615                 620

Lys Glu Met Ile Glu Tyr Arg Leu Lys Ser Tyr Asp Trp Trp Arg Met
625                 630                 635                 640

Arg Phe Tyr Asp Gln Cys Phe Ile Cys Asp Leu Ser
                645                 650
```

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: primer
      SN2172

<400> SEQUENCE: 49
gctcctcttt atcatgctat ggat                                          24

<210> SEQ ID NO 50
<211> LENGTH: 24

```
-continued
<212> TYPE: DNA
<213> ORGANISM: Artificial Sequence
<220> FEATURE:
<223> OTHER INFORMATION: Description of Artificial Sequence: primer
      SN2415

<400> SEQUENCE: 50
caggaaatgt ctcaggtact ttct                                           24
```